US006627405B1

(12) United States Patent
Nandabalan et al.

(10) Patent No.: US 6,627,405 B1
(45) Date of Patent: Sep. 30, 2003

(54) 53BP2 COMPLEXES

(75) Inventors: Krishnan Nandabalan, Guilford, CT (US); Meijia Yang, East Lyme, CT (US); Vincent Peter Schulz, Madison, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/338,123

(22) Filed: Jun. 22, 1999

Related U.S. Application Data

(62) Division of application No. 08/935,450, filed on Sep. 23, 1997, now Pat. No. 5,977,311.

(51) Int. Cl.$^7$ .............................................. G01N 33/53

(52) U.S. Cl. .......................... 435/7.1; 435/4; 435/69.4; 435/69.7; 530/350; 536/23.1

(58) Field of Search ............................ 435/4, 7.1, 69.4, 435/69.7, 71.1; 530/350, 358, 388.1, 388.8, 388.15, 389.1, 389.7; 536/23.1, 23.5

(56) References Cited

U.S. PATENT DOCUMENTS 6,184,205 B1    2/2001   Sparks et al.

FOREIGN PATENT DOCUMENTS

WO    WO 97/30074    8/1997

OTHER PUBLICATIONS

Burgess et al., Possible Dissociation of the Heparin–binding and Mitogenic Activities of Heaprin–binding (Acidic Fibroblast) Growth Factor–1 from Its Receptor–binding Activities by Site–directed Mutagenesis of a Single Lysine Residue, J of Cell Bio. 111:2, 1990.*
Lazar et al., Transforming Growth Factor alpha: Mutation of Aspartic Acid 47 and Leucine 48 Results in Different Biological Activites, Molecular and Cellular Biology 8:1247–1252, Mar. 1988.*
Tao et al., Studies of Aglycolsylated Chimeric Mouse–Human IgG, The Journal of Immunology, 143:2595–2601, 1989.*
Bowie et al, Deciperhing the Message in Protein Sequences: Tolerance to Amino Acid Substitutions, Science 247:1306–1310, Mar. 1990.*
Naumovski et al, The p53–Binding Protein 53BP2 Also Interacts with Bcl2 and Impedes Cell Cycle Progression at G2/M, Molecular and Cell Biology 16(7): 3884–3892, Jul. 11, 1996.*
Wilson et al, 2.2 Mb of contiguous nucleotide sequence from chromosome III of C. elegans, Nature 368(6466): 32–38, Mar. 03, 1994.*
Herzog et al, Accession Q61869 in J. Inves. Dermatol 102:165–170, Mar. 10, 1994.*

Giannakakou et al., The Journal of Biological Chemistry, 272(27):17118–17125, Jul. 1997.*
Ko et al., Genes & Development 10:1054–1072, 1996.*
Naumovdki et al., Molecular and Cellular Biology:16(7):3884–3892, Jul. 1996.*
Wall, Theriogenology 45:57–68, 1996.*
PCT International Search Report.
Banerjee, 1997. "Differential effects of colchicine and its B–ring modified analog MTPT on the assembly–independent GTPase activity of purified beta–tubulin isoforms from bovine brain." Biochem Biophys Res Commun. 231: 698–700.
Chien, et al., "The two–hybrid system: a method to identify and clone genes for proteins that interact with a protein of interest." *Proc Natl Acad Sci USA*. 88: 9578–9581, 1991.
Clark, et al., 1995. "Increased detection of specific tyosine phosphoproteins correlates with tumor progression of Abelson virus–infected lymphocytes." Leukemia. 9: 165–174.
Farine. 1997. "Animal models in autoimmune disease in immunotoxicity assessment." Toxicol., 119: 29–35.
Goldspiel, et al. 1993. "Human gene therapy." Clinical Pharmacy, 12: 488–505.
Good, et al. 1997. "Expression of small, therapeutic RNAs in human cell nuclei." Gene Therapy, 4: 45–54.
Gorina, et al., 1996. "Structure of the p53 tumor suppressor bound to the ankyrin and SH3 domains of 53BP2." Science. 274: 1001–1005.
Grassi, et al. 1996. "Ribozymes: structure, function, and potential therapy for dominant genetic disorders." Annals of Med., 28: 499–510.
Hecker, et al., 1996. "Complex regulation of the DNA–binding activity of p53 by phosphorylation: differential effects of individual phosphorylation sites on the interaction with different binding motifs." Oncogene. 12: 953–961.

(List continued on next page.)

*Primary Examiner*—Sheela Huff
(74) *Attorney, Agent, or Firm*—Ivor R. Elrifi; Naomi S. Biswas; Mintz, Levin, Cohn, Ferris, Glovsky and Popeo, P.C.

(57) ABSTRACT

The present invention relates to complexes of the 53BP2 protein with proteins identified as interacting with 53BP2 by a yeast two hybrid assay system. The proteins identified to interact with 53BP2 are β-tubulin, p62, hnRNP G, and three gene products, 53BP2-IP1, 53BP2-IP2, and 53BP2-IP3 encoded, in part, by the EST R72810 sequence. Thus, the invention provides complexes of 53BP2 and β-tubulin, p62, hnRNP G, 53BP2-IP1, 53BP2-IP2, and 53BP2-IP3 and derivatives, fragments and analogs thereof. The invention also provides the 53BP2-IP1, 53BP2-IP2 and 53BP2-IP3 genes and proteins and derivatives, fragments and analogs thereof. Methods of screening the complexes for efficacy in treating and/or preventing certain diseases and disorders, particularly cancer, autoimmune disease and neurodegenerative disease are also provided.

16 Claims, 21 Drawing Sheets

OTHER PUBLICATIONS

Helps, et al., 1995. "Protein phosphatase 1 interacts with p53BP2, a protein which binds to the tumour suppressor p53." FEBS Letts. 377: 295–300.

Itoh, et al., 1996. "Beta–tubulin binds Src homology 2 domains through a region different from the tyrosine–phosphorylated protein–recognizing site," J Biol Chem. 217: 27931–27935.

Iwabuchi, et al., 1994. "Two cellular proteins that bind to wild–type but not mutant p53." Proc Natl Acad Sci USA. 91: 6098–6102.

Kunkel, et al., 1996. "The role of chemokines in inflammatory joint disease," J Leukocyte Biol. 59: 6–12.

Martin, et al., "Stimulation of E2F1/DP1 transcriptional activity by MDM2 oncoprotein," Nature. 375: 691–694, 1995.

Milne, 1994. "Phosphorylation of the tumor suppressor protein p53 by mitogen–activated protein kinase." J Biol Chem. 269: 9253–9260.

Naumovski, et al., 1996. "The p53–binding protein 53BP2 also interacts with Bcl2 and impedes cell cycle progression at G2/M." Mol Cell Biol. 16: 3884–3892.

Neet, et al., 1995. "The nonreceptor protein–tyrosine kinase CSK complexes directly with the GTPase–activating protein–associated p62 protein in cells expressing v–Src or activated c–Src." Mol Cell Biol. 15: 4908–4920.

Popovic, "Behavioral and adaptive status in an experimental model of Alzheimer's disease in rats." *Int J Neurosci. 86*: 281–299, 1996.

Ranganathan, et al., 1997. "Immunohistochemical analysis of beta–tubulin isotypes in human prostate carcinoma and benign prostatic hypertrophy." Prostate. 30:263–268.

Richard, et al., 1995. "Association of p62, a multifunctional SH2–and SH3–domain–binding protein, with src family tyrosine kinases, Grb2, and phospholipase C gamma–1." Mol Cell Biol. 15: 186–197.

Soulard, et al., 1993. "hnRNP G: sequence and characterization of a glycosylated RNA–binding protein." Nuc Acids Res. 21: 4210–4217.

Tucker, et al., 1997. "Probing the kinesin–microtubule interaction." J Biol Chem. 272: 9481–9488.

Vadlamudi, et al., 1996. "p62, a phosphotyrosine–independent ligand of the SH2 domain of p56lck, belongs to a new class of ubiquitin–binding proteins." J Biol Chem. 271: 20235–0237.

Wang, et al., 1995. "P62 association with RNA is regulated by tyrosine phosphorylation." J. Biol Chem. 270: 2010–2013.

Wong, et al., 1992. "Molecular cloning and nucleic acid binding properties of the GAP–associated tyosine phosphoprotein p62." Cell. 69: 551–558.

* cited by examiner

```
GTCACGAGCG TCGAAGAGAC AAAGCCGCGT CAGGGGGCCC GGCCGGGGCG GGGGAGCCCG    60
GGGCTTGTTG GTGCCCCAGC CCGCGCGGAG GGCCCTTCGG ACCCGCGCGC CGCCGCTGCC   120
GCCGCCGCCG CCTCGCAACA GGTCCGGGCG GCCTCGCTCT CCGCTCCCCT CCCCCGCATC   180
CGCGACCCTC CGGGGCACCT CAGCTCGGCC GGGGCCGCAG TCTGGCCACC CGCTTCCATG   240
CGGTTCGGGT CCAAGATGAT GCCGATGTTT CTTACCGTGT ATCTCAGTAA CAATGAGCAG   300
CACTTCACAG AAGTTCCAGT TACTCCAGAA ACAATATGCA GAGACGTGGT GGATCTGTGC   360
AAAGAACCCG GCGAGAGTGA TTGCCATTTG GCTGAAGTGT GGTGTGGCTC TGTAGAGATA   420
GAGTTTCATC ATGTTGGCCA GGATGGTCTC GATCTCCTGA CCTTGTGATC CGCCTGCCTC   480
GGCCTCCCAA AGTGCTGGAT TACAGGTGTG AGCCACCACG ATCAGCCTCT AGTGTTTAAA   540
AAAGAACGTC CAGTTGCGGA TAATGAGCGA ATGTTTGATG TTCTTCAACG ATTTGGAAGT   600
CAGAGGAACG AAGTTCGCTT CTTCCTTCGT CATGAACGCC CCCCTGGCAG GGACATTGTG   660
AGTGGACCAA GATCTCAGGA TCCAAGTTTA AAAGAAATG GTGTAAAAGT TCCTGGTGAA    720
TATCGAAGAA AGGAGAACGG TGTTAATAGT CCTAGG ATG GAT CTG ACT CTT GCT    774
                                        Met Asp Leu Thr Leu Ala
                                        1                 5
```

| | | | | | | | | | | | | | | | | |
|---|---|---|---|---|---|---|---|---|---|---|---|---|---|---|---|---|
| GAA | CTT | CAG | GAA | ATG | GCA | TCT | CGC | CAG | CAG | CAA | CAG | ATT | GAA | GCC | CAG | 822 |
| Glu | Leu | Gln | Glu | Met | Ala | Ser | Arg | Gln | Gln | Gln | Gln | Ile | Glu | Ala | Gln | |
| | | 10 | | | | | 15 | | | | | | 20 | | | |

| | | | | | | | | | | | | | | | | |
|---|---|---|---|---|---|---|---|---|---|---|---|---|---|---|---|---|
| CAA | CAA | TTG | CTG | GCA | ACT | AAG | GAA | CAG | CGC | TTA | AAG | TTT | TTG | AAA | CAA | 870 |
| Gln | Gln | Leu | Leu | Ala | Thr | Lys | Glu | Gln | Arg | Leu | Lys | Phe | Leu | Lys | Gln | |
| | | 25 | | | | | 30 | | | | | 35 | | | | |

| | | | | | | | | | | | | | | | | |
|---|---|---|---|---|---|---|---|---|---|---|---|---|---|---|---|---|
| CAA | GAT | CAG | CGA | CAA | CAG | CAA | CAA | GTT | GCT | GAG | CAG | GAG | AAA | CTT | AAA | 918 |
| Gln | Asp | Gln | Arg | Gln | Gln | Gln | Gln | Val | Ala | Glu | Gln | Glu | Lys | Leu | Lys | |
| | 40 | | | | 45 | | | | | 50 | | | | | | |

| | | | | | | | | | | | | | | | | |
|---|---|---|---|---|---|---|---|---|---|---|---|---|---|---|---|---|
| AGG | CTA | AAA | GAA | ATA | GCT | GAG | AAT | CAG | GAA | GCT | AAG | CTA | AAA | AAA | GTG | 966 |
| Arg | Leu | Lys | Glu | Ile | Ala | Glu | Asn | Gln | Glu | Ala | Lys | Leu | Lys | Lys | Val | |
| 55 | | | | | 60 | | | | | 65 | | | | | 70 | |

| | | | | | | | | | | | | | | | | |
|---|---|---|---|---|---|---|---|---|---|---|---|---|---|---|---|---|
| AGA | GCA | CTT | AAA | GGC | CAC | GTG | GAA | CAG | AAG | AGA | CTA | AGC | AAT | GGG | AAA | 1014 |
| Arg | Ala | Leu | Lys | Gly | His | Val | Glu | Gln | Lys | Arg | Leu | Ser | Asn | Gly | Lys | |
| | | | | 75 | | | | 80 | | | | | 85 | | | |

| | | | | | | | | | | | | | | | | |
|---|---|---|---|---|---|---|---|---|---|---|---|---|---|---|---|---|
| CTT | GTG | GAG | GAA | ATT | GAA | CAG | ATG | AAT | AAT | TTG | TTC | CAG | CAA | AAA | CAG | 1062 |
| Leu | Val | Glu | Glu | Ile | Glu | Gln | Met | Asn | Asn | Leu | Phe | Gln | Gln | Lys | Gln | |
| | | | | 90 | | | | 95 | | | | 100 | | | | |

| | | | | | | | | | | | | | | | | |
|---|---|---|---|---|---|---|---|---|---|---|---|---|---|---|---|---|
| AGG | GAG | CTC | GTC | CTG | GCT | GTG | TCA | AAA | GTA | GAA | GAA | CTG | ACC | AGG | CAG | 1110 |
| Arg | Glu | Leu | Val | Leu | Ala | Val | Ser | Lys | Val | Glu | Glu | Leu | Thr | Arg | Gln | |
| | | 105 | | | | | 110 | | | | | 115 | | | | |

Fig. 1-1

```
CTA GAG ATG CTC AAG AAC GGC AGG ATC GAC AGC CAC CAT GAC AAT CAG      1158
Leu Glu Met Leu Lys Asn Gly Arg Ile Asp Ser His His Asp Asn Gln
120                 125                 130

TCT GCA GTG GCT GAG CTT GAT CGC CTC TAT AAG GAG CTG CAG CTA AGA      1206
Ser Ala Val Ala Glu Leu Asp Arg Leu Tyr Lys Glu Leu Gln Leu Arg
135                 140                 145                 150

AAC AAA TTG AAT CAA GAG CAG AAT GCC AAG CTA CAA CAA CAG AGG GAG      1254
Asn Lys Leu Asn Gln Glu Gln Asn Ala Lys Leu Gln Gln Gln Arg Glu
            155                 160                 165

TGT TTG AAT AAG CGT AAT TCA GAA GTG GCA GTC ATG GAT AAG CGT GTT      1302
Cys Leu Asn Lys Arg Asn Ser Glu Val Ala Val Met Asp Lys Arg Val
        170                 175                 180

AAT GAG CTG AGG GAC CGG CTG TGG AAG AAG AAG GCA GCT CTA CAG CAA      1350
Asn Glu Leu Arg Asp Arg Leu Trp Lys Lys Lys Ala Ala Leu Gln Gln
    185                 190                 195

AAA GAA AAT CTA CCA GTT TCA TCT GAT GGA AAT CTT CCC CAG CAA GCC      1398
Lys Glu Asn Leu Pro Val Ser Ser Asp Gly Asn Leu Pro Gln Gln Ala
200                 205                 210

GCG TCA GCC CCA AGC CGT GTG GCT GCA GTA GGT CCC TAT ATC CAG TCA      1446
Ala Ser Ala Pro Ser Arg Val Ala Ala Val Gly Pro Tyr Ile Gln Ser
215                 220                 225                 230

TCT ACT ATG CCT CGG ATG CCC TCA AGG CCT GAA TTG CTG GTG AAG CCA      1494
Ser Thr Met Pro Arg Met Pro Ser Arg Pro Glu Leu Leu Val Lys Pro
            235                 240                 245

GCC CTG CCG GAT GGT TCC TTG GTC ATT CAG GCT TCA GAG GGG CCG ATG      1542
Ala Leu Pro Asp Gly Ser Leu Val Ile Gln Ala Ser Glu Gly Pro Met
        250                 255                 260

AAA ATA CAG ACA CTG CCC AAC ATG AGA TCT GGG GCT GCT TCA CAA ACT      1590
Lys Ile Gln Thr Leu Pro Asn Met Arg Ser Gly Ala Ala Ser Gln Thr
    265                 270                 275

AAA GGC TCT AAA ATC CAT CCA GTT GGC CCT GAT TGG AGT CCT TCA AAT      1638
Lys Gly Ser Lys Ile His Pro Val Gly Pro Asp Trp Ser Pro Ser Asn
280                 285                 290

GCA GAT CTT TTC CCA AGC CAA GGC TCT GCT TCT GTA CCT CAA AGC ACT      1686
Ala Asp Leu Phe Pro Ser Gln Gly Ser Ala Ser Val Pro Gln Ser Thr
295                 300                 305                 310

GGG AAT GCT CTG GAT CAA GTT GAT GAT GGA GAG GTT CCG CTG AGG GAG      1734
Gly Asn Ala Leu Asp Gln Val Asp Asp Gly Glu VAl Pro Leu Arg Glu
            315                 320                 325
```

Fig. 1-2

```
AAA GAG AAG AAA GTG CGT CCG TTC TCA ATG TTT GAT GCA GTA GAC CAG    1782
Lys Glu Lys Lys Val Arg Pro Phe Ser Met Phe Asp Ala Val Asp Gln
            330             335             340

TCC AAT GCC CCA CCT TCC TTT GGT ACT CTG AGG AAG AAC CAG AGC AGT    1830
Ser Asn Ala Pro Pro Ser Phe Gly Thr Leu Arg Lys Asn Gln Ser Ser
            345             350             355

GAA GAT ATC TTG CGG GAT GCT CAG GTT GCA AAT AAA AAT GTG GCT AAA    1878
Glu Asp Ile Leu Arg Asp Ala Gln Val Ala Asn Lys Asn Val Ala Lys
    360             365             370

GTA CCA CCT CCT GTT CCT ACA AAA CCA AAA CAG ATT AAT TTG CCT TAT    1926
Val Pro Pro Pro Val Pro Thr Lys Pro Lys Gln Ile Asn Leu Pro Tyr
375             380             385             390

TTT GGA CAA ACT AAT CAG CCA CCT TCA GAC ATT AAG CCA GAC GGA AGT    1974
Phe Gly Gln Thr Asn Gln Pro Pro Ser Asp Ile Lys Pro Asp Gly Ser
                395             400             405

TCT CAG CAG TTG TCA ACA GTT GTT CCG TCC ATG GGA ACT AAA CCA AAA    2022
Ser Gln Gln Leu Ser Thr Val Val Pro Ser Met Gly Thr Lys Pro Lys
            410             415             420

CCA GCA GGG CAG CAG CCG AGA GTG CTG CTA TCT CCC AGC ATA CCT TCG    2070
Pro Ala Gly Gln Gln Pro Arg Val Leu Leu Ser Pro Ser Ile Pro Ser
            425             430             435

GTT GGC CAA GAC CAG ACC CTT TCT CCA GGT TCT AAG CAA GAA AGT CCA    2118
Val Gly Gln Asp Gln Thr Leu Ser Pro Gly Ser Lys Gln Glu Ser Pro
    440             445             450

CCT GCT GCT GCC GTC CGG CCC TTT ACT CCC CAG CCT TCC AAA GAC ACC    2166
Pro Ala Ala Ala Val Arg Pro Phe Thr Pro Gln Pro Ser Lys Asp Thr
455             460             465             470

TTA CTT CCA CCC TTC AGA AAA CCC CAG ACC GTG GCA GCA AGT TCA ATA    2214
Leu Leu Pro Pro Phe Arg Lys Pro Gln Thr Val Ala Ala Ser Ser Ile
                475             480             485

TAT TCC ATG TAT ACG CAA CAG CAG GCG CCA GGA AAA AAC TTC CAG CAG    2262
Tyr Ser Met Tyr Thr Gln Gln Gln Ala Pro Gly Lys Asn Phe Gln Gln
            490             495             500

GCT GTG CAG AGC GCG TTG ACC AAG ACT CAT ACC AGA GGG CCA CAC TTT    2310
Ala Val Gln Ser Ala Leu Thr Lys Thr His Thr Arg Gly Pro His Phe
            505             510             515

TCA AGT GTA TAT GGT AAG CCT GTA ATT GCT GCT GCC CAG AAT CAA CAG    2358
Ser Ser Val Tyr Gly Lys Pro Val Ile Ala Ala Ala Gln Asn Gln Gln
520             525             530
```

Fig. 1-3

```
CAG CAC CCA GAG AAC ATT TAT TCC AAT AGC CAG GGC AAG CCT GGC AGT    2406
Gln His Pro Glu Asn Ile Tyr Ser Asn Ser Gln Gly Lys Pro Gly Ser
535             540             545             550

CCA GAA CCT GAA ACA GAG CCT GTT TCT TCA GTT CAG GAG AAC CAT GAA    2454
Pro Glu Pro Glu Thr Glu Pro Val Ser Ser Val Gln Glu Asn His Glu
            555             560             565

AAC GAA AGA ATT CCT CGG CCA CTC AGC CCA ACT AAA TTA CTG CCT TTC    2502
Asn Glu Arg Ile Pro Arg Pro Leu Ser Pro Thr Lys Leu Leu Pro Phe
570             575             580

TTA TCT AAT CCT TAC CGA AAC CAG AGT GAT GCT GAC CTA GAA GCC TTA    2550
Leu Ser Asn Pro Tyr Arg Asn Gln Ser Asp Ala Asp Leu Glu Ala Leu
        585             590             595

CGA AAG AAA CTG TCT AAC GCA CCA AGG CCT CTA AAG AAA CGT AGT TCT    2598
Arg Lys Lys Leu Ser Asn Ala Pro Arg Pro Leu Lys Lys Arg Ser Ser
600             605             610

ATT ACA GAG CCA GAG GGT CCT AAT GGG CCA AAT ATT CAG AAG CTT TTA    2646
Ile Thr Glu Pro Glu Gly Pro Asn Gly Pro Asn Ile Gln Lys Leu Leu
615             620             625             630

TAT CAG AGG ACC ACC ATA GCG GCC ATG GAG ACC ATC TCT GTC CCA TCA    2694
Tyr Gln Arg Thr Thr Ile Ala Ala Met Glu Thr Ile Ser Val Pro Ser
            635             640             645

TAC CCA TCC AAG TCA GCT TCT GTG ACT GCC AGC TCA GAA AGC CCA GTA    2742
Tyr Pro Ser Lys Ser Ala Ser Val Thr Ala Ser Ser Glu Ser Pro Val
        650             655             660

GAA ATC CAG AAT CCA TAT TTA CAT GTG GAG CCC GAA AAG GAG GTG GTC    2790
Glu Ile Gln Asn Pro Tyr Leu His Val Glu Pro Glu Lys Glu Val Val
            665             670             675

TCT CTG GTT CCT GAA TCA TTG TCC CCA GAG GAT GTG GGG AAT GCC AGT    2838
Ser Leu Val Pro Glu Ser Leu Ser Pro Glu Asp Val Gly Asn Ala Ser
680             685         Ⓐ↓      690

ACA GAG AAC AGT GAC ATG CCA GCT CCT TCT CCA GGC CTT GAT TAT GAG    2886
Thr Glu Asn Ser Asp Met Pro Ala Pro Ser Pro Gly Leu Asp Tyr Glu
695             700             705             710

CCT GAG GGA GTC CCA GAC AAC AGC CCA AAT CTC CAG AAT AAC CCA GAA    2934
Pro Glu Gly Val Pro Asp Asn Ser Pro Asn Leu Gln Asn Asn Pro Glu
            715             720             725

GAA CCA AAT CCA GAG GCT CCA CAT GTG CTT GAT GTG TAC CTG GAG GAG    2982
Glu Pro Asn Pro Glu Ala Pro His Val Leu Asp Val Tyr Leu Glu Glu
            730             735             740
```

Fig. 1-4

| | | |
|---|---|---|
| TAC CCT CCA TAC CCA CCC CCA CCA TAC CCA TCT GGG GAG CCT GAA GGG<br>Tyr Pro Pro Tyr Pro Pro Pro Pro Tyr Pro Ser Gly Glu Pro Glu Gly<br>           745                           750                         755 | 3030 |

```
TAC CCT CCA TAC CCA CCC CCA CCA TAC CCA TCT GGG GAG CCT GAA GGG      3030
Tyr Pro Pro Tyr Pro Pro Pro Tyr Pro Ser Gly Glu Pro Glu Gly
    745             750             755

CCC GGA GAA GAC TCG GTG AGC ATG CGC CCG CCT GAA ATC ACC GGG CAG      3078
Pro Gly Glu Asp Ser Val Ser Met Arg Pro Pro Glu Ile Thr Gly Gln
    760             765             770

GTC TCT CTG CCT CCT GGT AAA AGG ACA AAC TTG CGT AAA ACT GGC TCA      3126
Val Ser Leu Pro Pro Gly Lys Arg Thr Asn Leu Arg Lys Thr Gly Ser
775             780             785             790

GAG CGT ATC GCT CAT GGA ATG AGG GTG AAA TTC AAC CCC CTT GCT TTA      3174
Glu Arg Ile Ala His Gly Met Arg Val Lys Phe Asn Pro Leu Ala Leu
                795             800             805

CTG CTA GAT TCG TCT TTG GAG GGA GAA TTT GAC CTT GTA CAG AGA ATT      3222
Leu Leu Asp Ser Ser Leu Glu Gly Glu Phe Asp Leu Val Gln Arg Ile
            810             815             820

ATT TAT GAG GTT GAT GAC CCA AGC CTG CCC AAT GAT GAA GGC ATC ACG      3270
Ile Tyr Glu Val Asp Asp Pro Ser Leu Pro Asn Asp Glu Gly Ile Thr
        825             830             835

GCT CTT CAC AAT GCT GTG TGT GCA GGC CAC ACA GAA ATC GTT AAG TTC      3318
Ala Leu His Asn Ala Val Cys Ala Gly His Thr Glu Ile Val Lys Phe
840             845             850

CTG GTA CAG TTT GGT GTA AAT GTA AAT GCT GCT GAT AGT GAT GGA TGG      3366
Leu Val Gln Phe Gly Val Asn Val Asn Ala Ala Asp Ser Asp Gly Trp
855             860             865             870

ACT CCA TTA CAT TGT GCT GCC TCA TGT AAC AAC GTC CAA GTG TGT AAG      3414
Thr Pro Leu His Cys Ala Ala Ser Cys Asn Asn Val Gln Val Cys Lys
            875             880             885

TTT TTG GTG GAG TCA GGA GCC GCT GTG TTT GCC ATG ACC TAC AGT GAC      3462
Phe Leu Val Glu Ser Gly Ala Ala Val Phe Ala Met Thr Tyr Ser Asp
        890             895             900

ATG CAG ACT GCT GCA GAT AAG TGC GAG GAA ATG GAG GAA GGC TAC ACT      3510
Met Gln Thr Ala Ala Asp Lys Cys Glu Glu Met Glu Glu Gly Tyr Thr
            905             910             915

CAG TGC TCC CAA TTT CTT TAT GGA GTT CAG GAG AAG ATG GGC ATA ATG      3558
Gln Cys Ser Gln Phe Leu Tyr Gly Val Gln Glu Lys Met Gly Ile Met
    920             925             930

AAT AAA GGA GTC ATT TAT GCG CTT TGG GAT TAT GAA CCT CAG AAT GAT      3606
Asn Lys Gly Val Ile Tyr Ala Leu Trp Asp Tyr Glu Pro Gln Asn Asp
935             940             945             950
```

Fig. 1-5

```
GAT GAG CTG CCC ATG AAA GAA GGA GAC TGC ATG ACA ATC ATC CAC AGG      3654
Asp Glu Leu Pro Met Lys Glu Gly Asp Cys Met Thr Ile Ile His Arg
            955                 960                 965

GAA GAC GAA GAT GAA ATC GAA TGG TGG TGG GCG CGC CTT AAT GAT AAG      3702
Glu Asp Glu Asp Glu Ile Glu Trp Trp Trp Ala Arg Leu Asn Asp Lys
            970                 975                 980

GAG GGA TAT GTT CCA CGT AAC TTG CTG GGA CTG TAC CCA AGA ATT AAA      3750
Glu Gly Tyr VAl Pro Arg Asn Leu Leu Gly Leu Tyr Pro Arg Ile Lys
            985                 990                 995

CCA AGA CAA AGG AGC TTG GCC TGAAACTTCC ACACAGAATT TTAGTCAATG AAGA    3805
Pro Arg Gln Arg Ser Leu Ala
    1000                1005

ATTAATCTCT GTTAAGAAGA AGTAATACGA TTATTTTTGG CAAAAATTTC ACAAGACTTA    3865

TTTTAATGAC AATGTAGCTT GAAAGCGATG AAGAATGTCT CTAGAAGAGA ATGAAGGATT    3925

GAAGAATTCA CCATTAGAGG ACATTTAGCG TGATGAAATA AAGCATCTAC GTCAGCAGGC    3985

CATACTGTGT TGGGGCAAAG GTGTCCCGTG TAGCACTCAG ATAAGTATAC AGCGACAATC    4045

CTGTTTTCTA CAAGAATCCT GTCTAGTAAA TAGGATCATT TATTGGGCAG TTGGGAAATG    4105

AGCTCTCTGT CCTGTTGAGT GTTTTCAGCA GCTGCTCCTA AACCAGTCCT CCTGCCAGAA    4165

AGGACCAGTG CCGTCACATC GCTGTCTCTG ATTGTCCCCG GCACCAGCAG GCCTTGGGGC    4225

TCACTGAAGG CTCGAAGGCA CTGCACACCT TGTATATTGT CAGTGAAGAA CGTTAGTTGG    4285

TTGTCAGTGA ACAATAACTT TATTATATGA GTTTTTGTAG CATCTTAAGA ATTATACATA    4345

TGTTTGAAAT ATTGAAACTA AGCTACAGTA CCAGTAATTA GATGTAGAAT CTTGTTTGTA    4405

GGCTGAATTT TAATCTGTAT TTATTGTCTT TTGTATCTCA GAAATTAGAA ACTTGCTACA    4465

GACTTACCCG TAATATTTGT CAAGATCATA GCTGACTTTA AAACAGTTG TAATAAACTT     4525

TTTGATGCT                                                           4534
```

Fig. 1-6

```
GCCCGCCGGT CCACGCCGCG CACCGCTCCG AGGGCCAGCG CCACCCGCTC CGCAGCCGGC    60

ACC ATG CGC GAG ATC GTG CAC ATC CAG GCG GGC CAG TGC GGC AAC CAG   108
    Met Arg Glu Ile Val His Ile Gln Ala Gly Gln Cys Gly Asn Gln
    1           5                   10                  15

ATC GGC GCC AAG TTT TGG GAG GTC ATC AGC GAT GAG CAT GGG ATC GAC   156
Ile Gly Ala Lys Phe Trp Glu Val Ile Ser Asp Glu His Gly Ile Asp
                20                  25                  30

CCC ACA GGC AGT TAC CAT GGA GAC AGT GAC TTG CAG CTG GAG AGA ATC   204
Pro Thr Gly Ser Tyr His Gly Asp Ser Asp Leu Gln Leu Glu Arg Ile
            35                  40                  45

AAC GTG TAC TAC AAT GAG GCT GCT GGT AAC AAA TAT GTA CCT CGG GCC   252
Asn Val Tyr Tyr Asn Glu Ala Ala Gly Asn Lys Tyr Val Pro Arg Ala
        50                  55                  60

ATC CTG GTG GAT CTG GAG CCT GGC ACC ATG GAC TCT GTC AGG TCT GGA   300
Ile Leu Val Asp Leu Glu Pro Gly Thr Met Asp Ser Val Arg Ser Gly
    65                  70                  75

CCC TTC GGC CAG ATC TTC AGA CCA GAC AAC TTC GTG TTC GGC CAG AGT   348
Pro Phe Gly Gln Ile Phe Arg Pro Asp Asn Phe Val Phe Gly Gln Ser
80                  85                  90                  95

GGA GCC GGG AAT AAC TGG GCC AAG GGC CAC TAC ACA GAG GGA GCC GAG   396
Gly Ala Gly Asn Asn Trp Ala Lys Gly His Tyr Thr Glu Gly Ala Glu
                100                 105                 110

CTG GTC GAC TCG GTC CTG GAT GTG GTG AGG AAG GAG TCA GAG AGC TGT   444
Leu Val Asp Ser Val Leu Asp Val Val Arg Lys Glu Ser Glu Ser Cys
            115                 120                 125

GAC TGT CTC CAG GGC TTC CAG CTG ACC CAC TCT CTG GGG GGC GGC ACG   492
Asp Cys Leu Gln Gly Phe Gln Leu Thr His Ser Leu Gly Gly Gly Thr
        130                 135                 140

GGG TCC GGG ATG GGC ACC CTG CTC ATC AGC AAG ATC CGG GAA GAG TAC   540
Gly Ser Gly Met Gly Thr Leu Leu Ile Ser Lys Ile Arg Glu Glu Tyr
    145                 150                 155

CCA GAC CGC ATC ATG AAC ACC TTC AGC GTC ATG CCC TCA CCC AAG GTG   588
Pro Asp Arg Ile Met Asn Thr Phe Ser Val Met Pro Ser Pro Lys Val
160                 165                 170                 175

TCA GAC ACG GTG GTG GAG CCC TAC AAC GCC ACC CTC TCG GTC CAC CAG   636
Ser Asp Thr Val Val Glu Pro Tyr Asn Ala Thr Leu Ser Val His Gln
                180                 185                 190

CTG GTG GAA AAC ACA GAT GAA ACC TAC TCC ATT GAT AAC GAG GCC CTG   684
Leu Val Glu Asn Thr Asp Glu Thr Tyr Ser Ile Asp Asn Glu Ala Leu
            195                 200                 205
```

Fig. 2-1

```
TAT GAC ATC TGC TTC CGC ACC CTG AAG CTG ACC ACC CCC ACC TAC GGG         732
Tyr Asp Ile Cys Phe Arg Thr Leu Lys Leu Thr Thr Pro Thr Tyr Gly
        210                 215                 220

GAC CTC AAC CAC CTG GTG TCG GCC ACC ATG AGC GGG GTC ACC ACC TGC         780
Asp Leu Asn His Leu Val Ser Ala Thr Met Ser Gly Val Thr Thr Cys
        225                 230                 235 Ⓐ↓

CTG CGC TTC CCG GGC CAG CTG AAC GCA GAC CTG CGC AAG CTG GCG GTG         828
Leu Arg Phe Pro Gly Gln Leu Asn Ala Asp Leu Arg Lys Leu Ala Val
240                 245                 250                 255

AAC ATG GTG CCC TTC CCT CGC CTG CAC TTC TTC ATG CCC GGC TTC GCG         876
Asn Met Val Pro Phe Pro Arg Leu His Phe Phe Met Pro Gly Phe Ala
                260 Ⓑ↓             265                 270

CCC CTG ACC AGC CGG GGC AGC CAG CAG TAC CGG GCG CTC ACG GTG CCC         924
Pro Leu Thr Ser Arg Gly Ser Gln Gln Tyr Arg Ala Leu Thr Val Pro
                275                 280                 285

GAG CTC ACC CAG CAG ATG TTC GAC TCC AAG AAC ATG ATG GCC GCC TGC         972
Glu Leu Thr Gln Gln Met Phe Asp Ser Lys Asn Met Met Ala Ala Cys
        290                 295                 300

GAC CCG CGC CAC GGC CGC TAC CTG ACG GTG GCT GCC ATC TTC CGG GGC        1020
Asp Pro Arg His Gly Arg Tyr Leu Thr Val Ala Ala Ile Phe Arg Gly
        305                 310                 315

CGC ATG TCC ATG AAG GAG GTG GAC GAG CAG ATG CTC AAC GTG CAG AAC        1068
Arg Met Ser Met Lys Glu Val Asp Glu Gln Met Leu Asn Val Gln Asn
320                 325                 330                 335

AAG AAC AGC AGC TAC TTC GTG GAG TGG ATC CCC AAC AAC GTG AAG ACG        1116
Lys Asn Ser Ser Tyr Phe Val Glu Trp Ile Pro Asn Asn Val Lys Thr
                340                 345                 350

GCC GTG TGC GAC ATC CCG CCC CGC GGC CTG AAG ATG TCG GCC ACC TTC        1164
Ala Val Cys Asp Ile Pro Pro Arg Gly Leu Lys Met Ser Ala Thr Phe
                355                 360                 365

ATC GGC AAC AGC ACG GCC ATC CAG GAG CTG TTC AAG CGC ATC TCC GAG        1212
Ile Gly Asn Ser Thr Ala Ile Gln Glu Leu Phe Lys Arg Ile Ser Glu
        370                 375                 380

CAG TTC ACG GCC ATG TTC CGG CGC AAG GCC TTC CTG CAC TGG TAC ACG        1260
Gln Phe Thr Ala Met Phe Arg Arg Lys Ala Phe Leu His Trp Tyr Thr
        385                 390                 395

GGC GAG GGC ATG GAC GAG ATG GAG TTC ACC GAG GCC GAG AGC AAC ATG        1308
Gly Glu Gly Met Asp Glu Met Glu Phe Thr Glu Ala Glu Ser Asn Met
400                 405                 410                 415
```

Fig. 2-2

```
AAC GAC CTG GTG TCC GAG TAC CAG CAG TAC CAG GAC GCC ACG GCC GAC    1356
Asn Asp Leu Val Ser Glu Tyr Gln Gln Tyr Gln Asp Ala Thr Ala Asp
                420                 425                 430

GAA CAA GGG GAG TTC GAG GAG GAG GAG GGC GAG GAC GAG G CTTAAAAACT   1406
Glu Gln Gly Glu Phe Glu Glu Glu Glu Gly Glu Asp Glu Ala
            435                 440                 445

TCTCAGATCA ATCGTGCATC CTTAGTGAAC TTCTGTTGTC CTCAAGCATG GTCTTTCTAC  1466

TTGTAAACTA TGGTGCTCAG TTTTGCCTCT GTTAGAAATT CACACTGTTG ATGTAATGAT  1526

GTGGAACTCC TCTAAAAATT ACAGTATTGT CTGTGAAGGT ATCTATACTA ATAAAAAAGC  1586

ATGTGTAG                                                          1594
```

Fig. 2-3

```
GGCTTCGGTC GCTACCGCTC CCGCTCTGCC ACCCCCGCCA ACCGCCGCTC GGGCCTCCGT      60

CGCTGCCGCG TCGCTTTCTC GCTCCTTGGA TCGCACATCC TCCCAG ATG CAG CGC        115
                                                 Met Gln Arg
                                                  1

CGG GAC GAC CCC GCC GCG CGC ATG AGC CGG TCT TCG GGC CGT AGC GGC       163
Arg Asp Asp Pro Ala Ala Arg Met Ser Arg Ser Ser Gly Arg Ser Gly
     5              10                  15

TCC ATG GAC CCC TCC GGT GCC CAC CCC TCG GTG CGT CAG ACG CCG TCT       211
Ser Met Asp Pro Ser Gly Ala His Pro Ser Val Arg Gln Thr Pro Ser
20              25                  30                  35

CGG CAG CCG CCG CTG CCT CAC CGG TCC CGG GGA GGC GGA GGG GGA TCC       259
Arg Gln Pro Pro Leu Pro His Arg Ser Arg Gly Gly Gly Gly Gly Ser
40                  45                  50

CGC GGG GGC CGG CGG GCC TCG CCC GCC ACG CAG CCG CCA CCG CTG CTG       307
Arg Gly Gly Ala Arg Ala Ser Pro Ala Thr Gln Pro Pro Pro Leu Leu
55                  60                  65

CCG CCC TCG GCC ACG GGT CCC GAC GCG ACA GTG GGC GGG CCA GCG CCG       355
Pro Pro Ser Ala Thr Gly Pro Asp Ala Thr Val Gly Gly Pro Ala Pro
70                  75                  80

ACC CCG CTG CTG CCC CCC TCG GCC ACA GCC TCG GTC AAG ATG GAG CCA       403
Thr Pro Leu Leu Pro Pro Ser Ala Thr Ala Ser Val Lys Met Glu Pro
85                  90                  95

GAG AAC AAG TAC CTG CCC GAA CTC ATG GCC GAG AAG GAC TCG CTC GAC       451
Glu Asn Lys Tyr Leu Pro Glu Leu Met Ala Glu Lys Asp Ser Leu Asp
100                 105                 110                 115

CCG TCC TTC ACT CAC GCC ATG CAG CTG CTG ACG GCA GAA ATT GAG AAG       499
Pro Ser Phe Thr His Ala Met Gln Leu Leu Thr Ala Glu Ile Glu Lys
120                 125                 130

ATT CAG AAA GGA GAC TCA AAA AAG GAT GAT GAG GAG AAT TAC TTG GAT       547
Ile Gln Lys Gly Asp Ser Lys Lys Asp Asp Glu Glu Asn Tyr Leu Asp
135                 140                 145

TTA TTT TCT CAT AAG AAC ATG AAA CTG AAA GAG CGA GTG CTG ATA CCT       595
Leu Phe Ser His Lys Asn Met Lys Leu Lys Glu Arg Val Leu Ile Pro
150                 155                 160

GTC AAG CAG TAT CCC AAG TTC AAT TTT GTG GGG AAG ATT CTT GGA CCA       643
Val Lys Gln Tyr Pro Lys Phe Asn Phe Val Gly Lys Ile Leu Gly Pro
165                 170                 175
```

Fig. 3-1

```
CAA GGG AAT ACA ATC AAA AGA CTG CAG GAA GAG ACT GGT GCA AAG ATC        691
Gln Gly Asn Thr Ile Lys Arg Leu Gln Glu Glu Thr Gly Ala Lys Ile
180             185                 190                 195

TCT GTA TTG GGA AAG GGC TCA ATG AGA GAC AAA GCC AAG GAG GAA GAG        739
Ser Val Leu Gly Lys Gly Ser Met Arg Asp Lys Ala Lys Glu Glu Glu
200             205                 210

CTG CGC AAA GGT GGA GAC CCC AAA TAT GCC CAC TTG AAT ATG GAT CTG        787
Leu Arg Lys Gly Gly Asp Pro Lys Tyr Ala His Leu Asn Met Asp Leu
215             220                 225

CAT GTC TTC ATT GAA GTC TTT GGA CCC CCA TGT GAG GCT TAT GCT CTT        835
His Val Phe Ile Glu Val Phe Gly Pro Pro Cys Glu Ala Tyr Ala Leu
230             235                 240

ATG GCC CAT GCC ATG GAG GAA GTC AAG AAA TTT CTA GTA CCG GAT ATG        883
Met Ala His Ala Met Glu Glu Val Lys Lys Phe Leu Val Pro Asp Met
245             250                 255                 Ⓐ↓

ATG GAT GAT ATC TGT CAG GAG CAA TTT CTA GAG CTG TCC TAC TTG AAT        931
Met Asp Asp Ile Cys Gln Glu Gln Phe Leu Glu Leu Ser Tyr Leu Asn
260             265                 270                 275

GGA GTA CCT GAA CCC TCT CGT GGA CGT GGG GTG CCA GTG AGA GGC CGG        979
Gly Val Pro Glu Pro Ser Arg Gly Arg Gly Val Pro Val Arg Gly Arg
280             285                 290

GGA GCT GCA CCT CCT CCA CCA CCT GTT CCC AGG GGC CGT GGT GTT GGA       1027
Gly Ala Ala Pro Pro Pro Pro Pro Val Pro Arg Gly Arg Gly Val Gly
295             300                 305

CCA CCT CGG GGG GCT TTG GTA CGT GGT ACA CCA GTA AGG GGA GCC ATC       1075
Pro Pro Arg Gly Ala Leu Val Arg Gly Thr Pro Val Arg Gly Ala Ile
310             315                 320

ACC AGA GGT GCC ACT GTG ACT CGA GGC GTG CCA CCC CCA CCT ACT GTG       1123
Thr Arg Gly Ala Thr Val Thr Arg Gly Val Pro Pro Pro Pro Thr Val
325             330                 335

AGG GGT GCT CCA GCA CCA AGA GCA CGG ACA GCG GGC ATC CAG AGG ATA       1171
Arg Gly Ala Pro Ala Pro Arg Ala Arg Thr Ala Gly Ile Gln Arg Ile
340             345                 350                 355

CCT TTG CCT CCA CCT CCT GCA CCA GAA ACA TAT GAA GAA TAT GGA TAT       1219
Pro Leu Pro Pro Pro Pro Ala Pro Glu Thr Tyr Glu Glu Tyr Gly Tyr
360             365                 370

GAT GAT ACA TAC GCA GAA CAA AGT TAC GAA GGC TAC GAA GGC TAT TAC       1267
Asp Asp Thr Tyr Ala Glu Gln Ser Tyr Glu Gly Tyr Glu Gly Tyr Tyr
375             380                 385

AGC CAG AGT CAA GGG GAC TCA GAA TAT TAT GAC TAT GGA CAT GGG GAG       1315
Ser Gln Ser Gln Gly Asp Ser Glu Tyr Tyr Asp Tyr Gly His Gly Glu
390             395                 400
```

Fig. 3-2

```
GTT CAA GAT TCT TAT GAA GCT TAT GGC CAG GAC GAC TGG AAT GGG ACC    1363
Val Gln Asp Ser Tyr Glu Ala Tyr Gly Gln Asp Asp Trp Asn Gly Thr
405                 410                 415

AGG CCG TCG CTG AAG GCC CCT CCT GCT AGG CCA GTG AAG GGA GCA TAC    1411
Arg Pro Ser Leu Lys Ala Pro Pro Ala Arg Pro Val Lys Gly Ala Tyr
420                 425                 430                 435

AGA GAG CAC CCA TAT GGA CGT TAT TAAAAACAAA CATGAGGGGA AAATATCAGT   1465
Arg Glu His Pro Tyr Gly Arg Tyr
                440         443
```

TATGAGCAAA GTTGTTACTG ATTTCTTGTA TCTCCCAGGA TTCCTGTTGC TTTACCCACA    1525

ACAGACAAGT AATTGTCTAA GTGTTTTTCT TCGTGGTCCC CTTCTTCTCC CCACCTTATT    1585

CCATTCTTAA CTCTGCATTC TGGCTTCTGT ATGTAGTATT TTAAAATGAG TTAAATAGA    1645

TTTAGGAATA TTGAATTAAT TTTTTAAGTG TGTAGATGCT TTTTTCTTTG TTGTTTAAAT   1705

ATAAACAGAA GTGTACCTTT TATAATAAAA AAAGAAGTT GAGTAAAAAA AAAAAACACA    1765

CAAACCTGTT AGTTTCAAAA ATGACATTGC TTGCTTAAAG GTTCTGAAGT AAAGGCTTGT   1825

TAAGTTTCTC TTAGTTTTGA TTTGAGGCAT CCCGTAAAGT TGTAGTTGCA GAATCCCAAA   1885

CTAGGCTACA TTTCAAAATT CAGGGCTGTT TAAGATTTAA AATCACAAAC ATTAACGGCA   1945

GTAGGCACCA CCATGTAAAA GTGAGCTCAG ACGTCTCTAA AAAATGTTTC CTTTATAAAA   2005

GCACATGGCG GTTGAATCTT AAGGTTAAAT TTTAATATGA AGATCCTCA TGAATTAAAT    2065

AGTTGATGCA ATTTTTAACG TTAATTGATA TAAAAAAAAA AACAACAAAA TTAGGCTTGT   2125

AAAACTGACT TTTTCATTAC GTGGGTTTTG AAATCTAGCC CCAGACATAC TGTGTTGAGA   2185

GATACTTAGA GGGAGGGAGT AGGTTTTGAA GAGGTTGATG GTGGTGGGGA GGGAAGGCCT   2245

CCTGAATTGA GTTTGATGCA GAGCTTTTTA GCCATGAAGA ATCTTTCAGT CATAGTACTA   2305

ATAATTAAAT TTTCAGTATT TAAAAAGACA AAGTATTTTG TCCATTTGAG ATTCTGCACT   2365

CCATGAAAAG TTCACTTGGA CGCTGGGGCC AAAAGCTGTT GATTTTCTTA AGTTGACGGT   2425

TGTCAATATA TCGAACTGTT CCCAAGTTAG TCAAGTATGT CTCAACACTA GCATGATATA   2485

AAAAGGGACA CTGCAGCTGA ATGAAAAAGG AATCAAAATC CACTTTGTAC ATAAGTTAAA   2545

GTCCTAATTG GATTTGTACC GTCCTCCCAT TTTGTTCTCG GAAGATTAAA TGCTACATGT   2605

GTAAGTCTGC CTAAATAGGT AGCTTAAACT TATGTCAAAA TGTCTGCAGC AGTTTGTCAA   2665

TAAAGTTTAG TCCTTTTTTA                                              2685

Fig. 3-3

```
CGGAAAAAAA A ATG GTT GAA GCA GAT CGC CCA GGA AAG CTC TTC ATT GGT      50
             Met Val Glu Ala Asp Arg Pro Gly Lys Leu Phe Ile Gly
              1           5                  10

GGG CTT AAT ACG GAA ACA AAT GAG AAA GCT CTT GAA GCA GTA TTT GGC       98
Gly Leu Asn Thr Glu Thr Asn Glu Lys Ala Leu Glu Ala Val Phe Gly
     15              20              25

AAA TAT GGA CGA ATA GTG GAA GTA CTC TTG ATG AAA GAC CGT GAA ACC      146
Lys Tyr Gly Arg Ile Val Glu Val Leu Leu Met Lys Asp Arg Glu Thr
 30              35              40              45

AAC AAA TCA AGA GGA TTT GCT TTT GTC ACC TTT GAA AGC CCA GCA GAC      194
Asn Lys Ser Arg Gly Phe Ala Phe Val Thr Phe Glu Ser Pro Ala Asp
             50              55              60

GCT AAG GAT GCA GCC AGA GAC ATG AAT GGA AAG TCA TTA GAT GGA AAA      242
Ala Lys Asp Ala Ala Arg Asp Met Asn Gly Lys Ser Leu Asp Gly Lys
             85              70              75

GCC ATC AAG GTG GAA CAA GCC ACC AAA CCA TCA TTT GAA AGT GGT AGA      290
Ala Ile Lys Val Glu Gln Ala Thr Lys Pro Ser Phe Glu Ser Gly Arg
         80              85              90

CGT GGA CCG CCT CCA CCT CCA AGA AGT AGA GGC CCT CCA AGA GGT CTT      338
Arg Gly Pro Pro Pro Pro Pro Arg Ser Arg Gly Pro Pro Arg Gly Leu
         95              100             105

AGA GGT GGA AGA GGA GGA AGT GGA GGA ACC AGG GGA CCT CCC TCA CGG      386
Arg Gly Gly Arg Gly Gly Ser Gly Gly Thr Arg Gly Pro Pro Ser Arg
110             115             120             125

GGA GGA CAC ATG GAT GAC GGT GGA TAT TCC ATG AAT TTT AAC ATG AGT      434
Gly Gly His Met Asp Asp Gly Gly Tyr Ser Met Asn Phe Asn Met Ser
             130             135             140

TCT TCC AGG GGA CCA CTC CCA GTA AAA AGA GGA CCA CCA CCA AGA AGT      482
Ser Ser Arg Gly Pro Leu Pro Val Lys Arg Gly Pro Pro Pro Arg Ser
             145             150             155

GGG GGT CCT CCT CCT AAG AGA TCT GCA CCT TCA GGA CCA GTT CGC AGT      530
Gly Gly Pro Pro Pro Lys Arg Ser Ala Pro Ser Gly Pro Val Arg Ser
             160             165             170

AGC AGT GGA ATG GGA GGA AGA GCT CCT GTA TCA CGT GGA AGA GAT AGT      578
Ser Ser Gly Met Gly Gly Arg Ala Pro Val Ser Arg Gly Arg Asp Ser
     175             180             185

TAT GGA GGT CCA CCT CGA AGG GAA CCG CTG CCC TCT CGT AGA GAT GTT      626
Tyr Gly Gly Pro Pro Arg Arg Glu Pro Leu Pro Ser Arg Arg Asp Val
190             195             200             205
```

Fig. 4-1

```
TAT TTG TCT CCA AGA GAT GAT GGG TAT TCT ACT AAA GAC AGC TAT TCA      674
Tyr Leu Ser Pro Arg Asp Asp Gly Tyr Ser Thr Lys Asp Ser Tyr Ser
                210                 215                 220

AGC AGA GAT TAC CCA AGT TCT CGT GAT ACT AGA GAT TAT GCA CCA CCA      722
Ser Arg Asp Tyr Pro Ser Ser Arg Asp Thr Arg Asp Tyr Ala Pro Pro
                225                 230                 235

CCA CGA GAT TAT ACT TAC CGT GAT TAT GGT CAT TCC AGT TCA CGT GAT      770
Pro Arg Asp Tyr Thr Tyr Arg Asp Tyr Gly His Ser Ser Ser Arg Asp
                240                 245                 250

GAC TAT CCA TCA AGA GAA TAT AGC GAT AGA GAT GGA TAT GGT CGT GAT      818
Asp Tyr Pro Ser Arg Glu Tyr Ser Asp Arg Asp Gly Tyr Gly Arg Asp
255             260                 265

CGT GAC TAT TCA GAT CAT CCA AGT GGA GGT TCC TAC AGA GAT TCA TAT      866
Arg Asp Tyr Ser Asp His Pro Ser Gly Gly Ser Tyr Arg Asp Ser Tyr
270                 275                 280                 285

GAG AGT TAT GGT AAC TCA CGT AGT GCT CCA CCT ACA CGA GGG CCC CCG      914
Glu Ser Tyr Gly Asn Ser Arg Ser Ala Pro Pro Thr Arg Gly Pro Pro
                290                 295                 300

CCA TCT TAT GGT GGA AGC AGT CGC TAT GAT GAT TAC AGC AGC TCA CGT      962
Pro Ser Tyr Gly Gly Ser Ser Arg Tyr Asp Asp Tyr Ser Ser Ser Arg
                305                 310                 315

GAC GGA TAT GGT GGA AGT CGA GAC AGT TAC TCA AGC AGC CGA AGT GAT     1010
Asp Gly Tyr Gly Gly Ser Arg Asp Ser Tyr Ser Ser Ser Arg Ser Asp
                320                 325                 330

CTC TAC TCA AGT GGT CGT GAT CGG GTT GGC AGA CAA GAA AGA GGG CTT     1058
Leu Tyr Ser Ser Gly Arg Asp Arg Val Gly Arg Gln Glu Arg Gly Leu
                335                 340                 345

CCC CCT TCT ATG GAA AGG GGG TAC CTC CTC CAC GTG ATT CCT ACA GCA     1106
Pro Pro Ser Met Glu Arg Gly Tyr Leu Leu His Val Ile Pro Thr Ala
350                 355                 360                 365

GTT CAA GCC GCG GAC GAC CAA GAG GTG GTG GCC GTG GAG GAA GCC GAT     1154
Val Gln Ala Ala Asp Asp Gln Glu Val Val Ala Val Glu Glu Ala Asp
                370                 375                 380

CTG ATA GAG GGG GAG GCA GAA GCA GAT ACT AGA AAC AAA CAA AAC TTT     1202
Leu Ile Glu Gly Glu Ala Glu Ala Asp Thr Arg Asn Lys Gln Asn Phe
                385                 390                 395

GGA CCA AAA TCC CAG TTC AAA GAA ACA AAA AGT GGA AAC TAT TCT ATC     1250
Gly Pro Lys Ser Gln Phe Lys Glu Thr Lys Ser Gly Asn Tyr Ser Ile
        400                 405                 410
```

Fig. 4-2

```
ATA ACT ACC CAA GGA CTA CTA AAA GGA AAA ATT GTG TTA CTT TTT TTA    1298
Ile Thr Thr Gln Gly Leu Leu Lys Gly Lys Ile Val Leu Leu Phe Leu
    415                 420                 425

AAT TCC CTG TTA AGT TCC CCT CCA TAATTTTTAT GTTCTTGTGA GGAAAAAAGT   1352
Asn Ser Leu Leu Ser Ser Pro Pro
430                 435

AAAACATGTT TAATTTTATT TGACTTCTGC ATTGCTTTTC AACAAGCAAA TGTTAAATGT  1412

GTTAAGACTT GTACTAGTGT TGTAACTTTC CAAGTAAAAG TATCCCCTAA AGGCCACTTC  1472

CTATCTGATT TTTCCCAGCA AATGAGGCAG GCAATTCTAG TCTTCCACAA AACATCTAGC  1532

CATCTAAAAT GGAGAGATGA ATCATTCTAC CTATACAAAC AAGCTAGCTA TTAGAGGGTG  1592

GTTGGGGTAT GCTACTCATA AGATTTCAGG GTGTCTTCCA ACTGAAATCT CAATGTTCTC  1652

AGTACGAAAA ACCTGAAATC ACATGCCTAT GTAAGGAAAG TGCTATTCAC CCAGTAAACC  1712

CAAAAAAGCA AATGGATAAT GCTGGCCATT TTGCCTTTCT GACATTTCCT TGGGAATCTG  1772

CAAGAACCTC CCCTTTCCCT TCCCCAATA AGACCATTTA AGTGTGTGTT AAACAACTAC   1832

AGAATACTAA GTAAAAAGTT TGGCCAAAAC CAAAAAAAAA AAAAAAAAAA AAAAAAAAA   1892

Ⓐ↓
```
GCTATAGCAG AACCGCTGGG GTAACAACAA CCGGGATAAC AACAACTCCA ACAACAGAGG      60
CAGCTACAAC CGGGCTCCCC AGCAACAGCC GCCACCACAG CAGCCTCCGC CACCACAGCC     120
ACCACCCCAG CAGCCACCGC CACCACCCAG CTACAGCCCT GCTCGGAACC CCCCAGGGGC     180
CAGCACCTAC AATAAGAACA GCAACATCCC TGGCTCAAGC GCCAATACCA GCACCCCCAC     240
CGTCAGCAGC TACAGCCCTT CCACAGCCGA GTTACAGCCA GCCACCCTAC ANCCAGGGGA     300
GGTTACAGCC AGGGTTACAC AGG                                            323
```

Fig. 5

BAIT PROTEINS

|  | B1 | MDM2 | 53BP2 |
|---|---|---|---|
| P1 | | | |
| P2 | | | |
| PP1α | A + | | B + |
| p62 | | | C + |
| β-tub. | | | D + |

PREY PROTEINS

> Ⓐ↓
GGCGGCTTCC AGAAAAAAGG GGAGGCAGCG GTGGAGGAGG CAACTACCGA GGAGGTTTCA 60
ACCGCAGCGG AGGTGGTGGC TATAGCAGAA CCGCTGGGGT AACAACAACC GGGATAACAA 120
CAACTCCAAC AACAGAGGCA GCTACAACCG GGCTCCCCAG CAACAGCCGC CACCACAGCA 180
GCCTCCGCCA CCACAGCCAC CACCCCAGCA GCCACCGCCA CCACCCAGCT ACAGCCCTGC 240
TCGGAACCCC CCAGGGGCCA GCACCTACAA TAAGAACAGC AACATCCCTG GCTCAAGCGC 300
CAATACCAGC ACCCCCACCG TCAGCAGCTA CAGCCCTTCC ACAG CCGAGT TACAGCCAGC 360
★ CACCCTACAA CCAGGGGAGG TTACAGCCAG GGTTACACAG GCCCACCGCC TCCACCTCCA 420
CCACCACCTG CCTACAACTA TGGGAGCTAC GGCGGTTACA ACCCGGCCCC CTATACCCCA 480
CCGCCACCCC CCACCGCACA GACCTACCCT CAGCCCAACT ATAACCAGTA TCAGCAGTAT 540
*GCCAGCAGTG GAACCAGTAC TATCAGAACC AGGGCCAGTG GCGCCATACT ACGGGAACTA* 600
*CGACTACGGG AGCTACTCCG GGAACACACA GGGTGGCACA AGTACACAGT AGCCAGTGTG* 660
*ACCCAGAGGC TCCCGGAGGC CCCTGCCGGC TTCCTCCACC AGCGCCTGCCT CGGCCCCTC* 720
*CTCTGCCCCC GCCAGATCCC GTGGTGCTGG GGATGGGGTC ATCCAGGGC TGCCTCCCTC* 780
*CAGCCCACTG CCTCCCCTCT GAGGGGCTTC CTTCCCCTCC ATAGGGCCAG GCATTTTTTT* 840
*CTGGATTCAA ACAGGCAACA ATGACCTTTT ATTTTCTGTT TGTCCCCACC TCCCAGCCT* 900
*TCCACCTCCT GTTC* 915

EST C17385-DERIVED SEQUENCE    bold underline
EST R72810-DERIVED SEQUENCE    bold lettering
EST AA464793-DERIVED SEQUENCE    boxed lettering
EST AA479761-DERIVED SEQUENCE    bold italic lettering

Fig. 9

A.  53BP2-IP3
    [▓▓▓▓░░░░░░░░░░░░░░░░░░░░░░░░] Translation Frame +1 1-102

```
  1 GGC GGC TTC CAG AAA AAA GGG GAG GCA GCG GTG GAG GAG GCA ACT
    Gly Gly Phe Gln Lys Lys Gly Glu Ala Ala Val Glu Glu Ala Thr
```

B.
```
 46 ACC GAG GAG GTT TCA ACC GCA GCG GAG GTG GTG GCT ATA GCA GAA
    Thr Glu Glu Val Ser Thr Ala Ala Glu Val Val Ala Ile Ala Glu

91 CCG CTG GGG TAA 102
    Pro Leu Gly *
```

C.  53BP2-IP2
    [░░░░░░░░░░░░▓▓▓▓▓▓░░░░░░░░░░] Translation Frame +2 440-652

```
440 ATG GGA GCT ACG GCG GTT ACA ACC CGG CCC CCT ATA CCC CAC CGC
    Met Gly Ala Thr Ala Val Thr Thr Arg Pro Pro Ile Pro His Arg

485 CAC CCC CCA CCG CAC AGA CCT ACC CTC AGC CCA ACT ATA ACC AGT
    His Pro Pro Pro His Arg Pro Thr Leu Ser Pro Thr Ile Thr Ser
```

D.
```
530 ATC AGC AGT ATG CCA GCA GTG GAA CCA GTA CTA TCA GAA CCA GGG
    Ile Ser Ser Met Pro Ala Val Glu Pro Val Leu Ser Glu Pro Gly

575 CCA GTG GCG CCA TAC TAC GGG AAC TAC GAC TAC GGG AGC TAC TCC
    Pro Val Ala Pro Tyr Tyr Gly Asn Tyr Asp Tyr Gly Ser Tyr Ser

620 GGG AAC ACA CAG GGT GGC ACA AGT ACA CAG TAG 652
    Gly Asn Thr Gln Gly Gly Thr Ser Thr Gln *
```

E.  53BP2-IP1
    [▓▓▓▓▓▓▓▓▓▓▓▓░░░░░░░░░░░░░░░░] Translation Frame +3 3-524

```
  3 CGG CTT CCA GAA AAA AGG GGA GGC AGC GGT GGA GGA GGC AAC TAC
    Arg Leu Pro Glu Lys Arg Gly Gly Ser Gly Gly Gly Gly Asn Tyr
```

F.
```
 48 CGA GGA GGT TTC AAC CGC AGC GGA GGT GGT GGC TAT AGC AGA ACC
    Arg Gly Gly Phe Asn Arg Ser Gly Gly Gly Gly Tyr Ser Arg Thr

93 GCT GGG GTA ACA ACA ACC GGG ATA ACA ACA ACT CCA ACA ACA GAG
    Ala Gly Val Thr Thr Thr Gly Ile Thr Thr Thr Pro Thr Thr Glu
```

Fig. 10-1

```
138  GCA GCT ACA ACC GGG CTC CCC AGC AAC AGC CGC CAC CAC AGC AGC
     Ala Ala Thr Thr Gly Leu Pro Ser Asn Ser Arg His His Ser Ser

183  CTC CGC CAC CAC AGC CAC CAC CCC AGC AGC CAC CGC CAC CAC CCA
     Leu Arg His His Ser His His Pro Ser Ser His Arg His His Pro

228  GCT ACA GCC CTG CTC GGA ACC CCC CAG GGG CCA GCA CCT ACA ATA
     Ala Thr Ala Leu Leu Gly Thr Pro Gln Gly Pro Ala Pro Thr Ile

273  AGA ACA GCA ACA TCC CTG GCT CAA GCG CCA ATA CCA GCA CCC CCA
     Arg Thr Ala Thr Ser Leu Ala Gln Ala Pro Ile Pro Ala Pro Pro

318  CCG TCA GCA GCT ACA GCC CTT CCA CAG CCG AGT TAC AGC CAG CCA
     Pro Ser Ala Ala Ser Ala Leu Pro Gln Pro Ser Tyr Ser Gln Pro

363  CCC TAC AAC CAG GGG AGG TTA CAG CCA GGG TTA CAC AGG CCC ACC
     Pro Tyr Asn Gln Gly Arg Leu Gln Pro Gly Leu His Arg Pro Thr

408  GCC TCC ACC TCC ACC ACC ACC TGC CTA CAA CTA TGG GAG CTA CGG
     Ala Ser Thr Ser Thr Thr Thr Cys Leu Gln Leu Trp Glu Leu Arg

453  CGG TTA CAA CCC GGC CCC CTA TAC CCC ACC GCC ACC CCC CAC CGC
     Arg Leu Gln Pro Gly Pro Leu Tyr Pro Thr Ala Thr Pro His Arg

498  ACA GAC CTA CCC TCA GCC CAA CTA TAA 524
     Thr Asp Leu Pro Ser Ala Gln Leu *
```

Fig. 10-2

53BP2 COMPLEXES

RELATED APPLICATIONS

This application is a divisional application under 37 C.F.R. §1.53(b) of U.S. Ser. No. 08/935,450, filed on Sep. 23, 1997, now U.S. Pat. No. 5,977,311, incorporated herein by reference in its entirety.

This invention was made with United States Government support under award number 70NANB5H1066 awarded by the National Institute of Standards and Technology. The United States Government has certain rights in the invention.

FIELD OF THE INVENTION

The field of this invention is the complexes of 53BP2 protein with other proteins, in particular, complexes of 53BP2 with β-tubulin, 53BP2 with p62, 53BP2 with hnRNP G, 53BP2 with 53BP2-IP1, 53BP2 with 53BP2-IP2, and 53BP2 with 53BP2-IP3 proteins. The invention includes antibodies to 53BP2 complexes, and their use in, inter alia, screening, diagnosis, prognosis and therapy. The invention further relates to 53BP2-IP1, 53BP2-IP2, and 53BP2-IP3 genes and proteins and derivatives, fragments and analogs, thereof.

BACKGROUND OF THE INVENTION

53BP2

The human Bcl2/p53 binding protein, known as 53BP2, or BBP (GenBank Accession Number U58334, Naumovski and Cleary, 1996, Mol. Cell. Biol. 16: 3884–3892) impedes cell cycle progression from G2 to M phase. 53BP2 competes with Bcl2 for binding to p53, and thus is critical for modulation of p53 function (Naumovski and Cleary, 1996, Mol. Cell. Biol. 16: 3884–3892). In turn, p53 is a critical tumor suppressor protein that can activate or repress transcription, and thus mediate cell cycle progression (Murray and Hunt, 1993, *The Cell Cycle: An Introduction*, W. H. Freeman and Co., New York). 53BP2 binds to the central DNA binding domain of p53 via two adjacent ankryin repeats and an SH3 domain, thus supporting its ability to modulate, inter alia, p53 DNA binding and stability, and thus, its tumor suppression (Iwabuchi et al., 1994, Proc. Natl. Acad. Sci. USA 91: 6098–6102). Importantly, the most frequent p53 mutations observed in human cancers map to the region of 53BP2 binding (Gorina and Pavletich, 1996, Science 274: 1001–1005). 53BP2 also modulates the dephosphorylation status, and thus the function of p53, via its binding to protein phosphatase 1 (PP1), thus inhibiting the latter protein's ability to dephosphorylate p53 (Helps et al., 1995, FEBS Letts. 377: 295–300). Phosphorylation at multiple p53 sites affects its transcriptional activation/inhibition, but in a complicated fashion that is not easy to predict (Fuchs et al., 1995, Eur J Biochem 228: 625–639; Hecker et al., 1996, Oncogene 12: 953–961). The above data indicate that proteins that interact with 53BP2 have a fairly direct means to modulate p53 function. It has been previously shown that one such protein, PP1, binds to the C-terminal region of 53BP2 containing the critical ankyrin and SH3 binding domains (Helps et al., 1995, FEBS Letts. 377: 295–300). In sum, 53BP2 has likely roles in the control of cell cycle progression, transcriptional regulation, cellular apoptosis and differentiation, intracellular signal transduction, and tumorigenesis.

β-Tubulin

Human β-tubulin (GenBank Accession No. X79535, Leffers et al., 1994, GenBank direct submission Jun. 1, 1994) exists in at least six different isoforms that are expressed from separate genes in a tissue specific distribution (Ranganathan et al., 1997, Prostate 30: 263–268). Tubulins are critical to the enzymic-mechanical conversion of ATP hydrolysis to molecular movement along microtubules. The C-terminus of β-tubulin, in particular the last 12 amino acid residues, interacts with kinesin motors to modulate microtubule polymerization, dynamics, and drug sensitivity (Ranganathan et al., 1997, Prostate 30: 263–268; Tucker and Goldstein, 1997, J. Biol. Chem. 272: 9481–9488). This function may have pathophysiological significance; type IV β-tubulin is highly expressed in adenocarcinomas of the prostate, and type II β-tubulin expression is up-regulated in adenocarcinomas that become malignant (Ranganathan et al., 1997, Prostate 30: 263–268). Colchicine, which specifically interacts with β-tubulins to arrest cellular outgrowth, is an effective antitumor agent (Banerjee, 1997, Biochem. Biophys. Res. Commun. 231: 698–700). Further, microtubules, possibly through beta-tubulin binding to proteins that contain Src homology 2 (SH2) domains, play important roles in the assembly of signaling molecular complexes involved in cellular transformation (Itoh et al., 1996, J. Biol. Chem. 217: 27931–27935). In summary, β-tubulin has roles in tumorigenesis and tumor progression, cell structure and intracellular protein transport, cell differentiation, and intracellular signalling.

p62

Human p62 (GenBank Accession No. M88108, Wong et al., 1992, Cell 69: 551–558) is a 62 kD tyrosine phosphoprotein that displays significant homology to the hnRNP protein GRP33. p62 associates with the $p21^{waf}$GTPase-activating protein (GAP). The binding depends on the phosphorylation state of p62 and occurs via SH2 domains in GAP (Wong et al., 1992, Cell 69: 551–558). The protein p62 further associates with Src family tyrosine kinase SH3 domains in signalling proteins. Since p62 can interact with multiple proteins at once via its several SH3 binding domains, p62 serves to physically link Src kinase activity with downstream effectors such as GRB2 and phospholipase C gamma-1 (Richard et al., 1995, Mol. Cell. Biol. 15: 186–197). In its dephosphorylated state, p62 actively binds RNA via a "KH domain" (Wang et al., 1995, J. Biol. Chem. 270: 2010–2013). Phosphorylation severely impairs p62 binding to RNA, suggesting that p62 RNA binding is regulated in vivo. p62 is known to specifically interact with ubiquitin via its C-terminal 80 residues (Vadlamudi et al., 1996, J. Biol. Chem. 271: 20235–20237), thus implicating p62 in ubiquitin-mediated proteolysis. It also specifically interacts with CSK, a cytosolic protein tyrosine kinase that negatively regulates Src family protein tyrosine kinases, and it is hypothesized that this binding mediates docking of proteins, including GAP and CSK, to cytoskeletal and membrane regions upon c-Src activation (Neet and Hunter, 1995, Mol. Cell. Biol. 15: 4908–4920). Levels of phospho-p62, detected by Western blotting, increase markedly in v-abl transformed lymphoblasts (a cell model of leukemia) that reach advanced stages of feeder-layer independent agar growth (Clark and Liang, 1995, Leukemia 9: 165–174). In summary, p62 is implicated in cell transformation and tumor progression, intracellular signalling and cellular activation by c-Src, ubiquitin-mediated proteolysis, and mRNA binding and metabolism.

hnRNP G

Human hnRNP G protein (GenBank Accession No. Z23064; Soulard et al., 1993, Nucleic Acids Res. 21:

4210–4217) is an RNA binding protein whose homolog (p43) was originally identified as an autoantigenic nuclear protein in dogs with a lupus-like syndrome. It is a glycosylated component of heterogenous nuclear ribonucleoprotein complexes that contains an RNA binding domain at its amino terminus and a carboxyl domain rich in serines, arginines, and glycines (Soulard et al., 1993, Nucleic Acids Res. 21: 4210–4217). Likely roles for hnRNP G include regulation of cell division, translational, and transcription. It may also function in various autoimmune diseases, such as systemic lupus erythematosus and rheumatoid arthritis.

The newly identified 53BP2-IP1, 53BP2-IP2 and 53BP2-IP3 proteins are encoded in part by a nucleotide sequence identified as EST R72810 in the GenBank Database (Hillier et al., 1995, GenBank Direct Submission Jun. 2, 1995, Accession No. 157775) obtained from the Soares (human) breast library 2NbHBst. Over a span of 54 nucleotides, the EST R72810 sequence displays 74% identity to the Simian immunodeficiency virus SIVpt5 gene (GenBank Accession No. U05129), but otherwise displays no significant homology to known proteins.

53BP2 complexes with any of β-tubulin, p62, hnRNP G, 53BP2-IP1, 53BP2-IP2, or 53BP2-IP3 have not been previously described.

Citation of a reference herein shall not be construed as an admission that such is prior art to the present invention.

SUMMARY OF THE INVENTION

The present invention provides certain compositions and methods of production of protein complexes of 53BP2 with proteins that interact with (i.e., bind to) 53BP2 (the proteins shown to bind with 53BP2 are designated "53BP2-IP" for 53BP2 interacting protein, and the complexes of 53BP2 and a 53BP2-IP are designated as 53BP2:53BP2-IP herein). Specifically, the invention relates to complexes of 53BP2, and derivatives, fragments and analogs of 53BP2 with β-tubulin, with p62, with hnRNP G, with 53BP2-IP1, with 53BP2-IP2 and with 53BP2-IP3, and their derivatives, analogs and fragments. The present invention further provides methods of screening for proteins that interact with 53BP2, or derivatives, fragments or analogs, thereof; preferably the method of screening is a yeast two hybrid assay system or a variation thereof.

The invention further relates to nucleotide sequences of 53BP2-IP1, 53BP2-IP2 and 53BP2-IP3 genes (human 53BP2-IP1, 53BP2-IP2, and 53BP2-IP3 genes and homologs of other species), as well as derivatives (e.g., fragments) and analogs thereof. Nucleic acids hybridizable to or complementary to the foregoing nucleotide sequence, such as the inverse complement (i.e. has the complementary sequence running in reverse orientation to the strand so that the inverse complement would hybridize without mismatches to the nucleic acid strand; thus, for example, where the coding strand is hybridizable to a nucleic acid with no mismatches between the coding strand and the hybridizable strand, then the inverse complement of the hybridizable strand is identical to the coding strand) of the foregoing sequences, are provided. The invention also relates to 53BP2-IP1, 53BP2-IP2 and 53BP2-IP3 derivatives and analogs of the invention that are functionally active, i.e., they are capable of displaying one or more known functional activities of a wild-type 53BP2-IP1, 53BP2-IP2, or 53BP2-IP3 protein. Such functional activities include, but are not limited to ability to bind with [or compete for binding with] 53BP2, antigenicity [ability to bind (or compete with 53BP2-IP1, 53BP2-IP2 or 53BP2-IP3 for binding) to an anti-53BP2-IP1, anti-53BP2-IP2 or anti-53BP2-IP3 antibody, respectively], and immunogenicity (ability to generate antibody which binds 53BP2-IP1, 53BP2-IP2, or 53BP2-IP3, respectively).

Methods of production of the 53BP2:53BP2-IP complexes and of 53BP2-IP1, 53BP2-IP2, and 53BP2-IP3 proteins, and derivatives and analogs of the complexes and proteins, e.g., by recombinant means, are also provided. Pharmaceutical compositions are also provided.

The invention further provides methods of modulating (i.e., inhibiting or enhancing) the activity of 53BP2:53BP2-IP complexes, particularly 53BP2:β-tubulin, 53BP2:p62, 53BP2:hnRNP G, 53BP2:53BP2-IP1, 53BP2:53BP2-IP2, or 53BP2:53BP2-IP3 complexes. The protein components of the complexes have been implicated in cellular functions, including but not limited to: control of cell cycle progression, cellular differentiation and apoptosis, tumorigenesis and tumor progression; regulation of transcription and translation; control of intracellular signal transduction, including c-Src signalling; control of ubiquitin-mediated protein degradation, and processing involving mRNA binding and stability. Accordingly, the invention provides methods of screening 53BP2:53BP2-IP complexes, particularly complexes of 53BP2 with β-tubulin, p62, hnRNP G, 53BP2-IP1, 53BP2-IP2, or 53BP2-IP3 and the 53BP2-IP1, 53BP2-IP2 and 53BP2-IP3 proteins, as well as derivatives and analogs of the 53BP2:53BP2-IP complexes and 53BP2-IP1, 53BP2-IP2 and 53BP2-IP3 proteins for the ability to alter cell functions, particularly those cell functions in which 53BP2 and/or a 53BP2-IP has been implicated, such as but not limited to, cell proliferation, differentiation and apoptosis, tumorigenesis and cell transformation, intracellular signal transduction, gene expression, ubiquitin-mediated protein degradation, and mRNA stability.

The present invention also relates to therapeutic and prophylactic as well as diagnostic, prognostic, and screening methods and compositions based upon 53BP2:53BP2-IP complexes (and the nucleic acids encoding the individual proteins that participate in the complexes) as well as 53BP2-IP1 and 53BP2-IP2 and 53BP2-IP3 proteins and nucleic acids. Therapeutic compounds of the invention include, but are not limited to, 53BP2:53BP2-IP complexes and complexes where one or both members of the complex is a derivative or analog of 53BP2 or 53BP2-IP; 53BP2-IP1, 53BP2-IP2 and 53BP2-IP3 proteins and derivatives, fragments and analogs thereof; antibodies to and nucleic acids encoding the foregoing; and antisense nucleic acids to the nucleotide sequences encoding the complex components and 53BP2-IP1, 53BP2-IP2, and 53BP2-IP3 antisense nucleic acids. Diagnostic, prognostic and screening kits are also provided.

Animal models and methods of screening for modulators (i.e. agonists, antagonists and inhibitors) of the activity of 53BP2:53BP2-IP complexes and 53BP2-IP1, 53BP2-IP2 and 53BP2-IP3 proteins are also provided.

Methods of identifying molecules that inhibit, or alternatively, that increase formation of 53BP2:53BP2-IP complexes are also provided.

BRIEF DESCRIPTION OF THE DRAWINGS

FIG. 1. The nucleotide sequence of 53BP2 (GenBank Accession No. U58334 (SEQ ID NO: 1)) and deduced amino acid sequence (SEQ ID NO:2). The amino-terminal start site of the sequence used as bait in the assays described in Section 6, infra, is indicated by the arrow labeled "A".

FIG. 2. The nucleotide sequence (SEQ ID NO:3) and amino acid sequence (SEQ ID NO:4) of β-tubulin (GenBank Accession No. X79535). Prey sequence A begins at base 820 (and amino acid 253) at the arrow labeled "A". Prey sequence B begins at base 895 (and amino acid 278) at the arrow labeled "B".

FIG. 3. The nucleotide sequence and corresponding amino acid sequence of the p62 protein (GenBank Accession No. M88108 (SEQ ID NOS:5 and 6, respectively)). The amino-terminal start site of the prey sequence identified in the assay described in Section 6, infra, is indicated by the arrow labeled "A".

FIG. 4. The hnRNP G nucleotide acid sequence (SEQ ID NO:7) and amino acid sequence (SEQ ID NO:8). The amino-terminal start site of the prey sequence identified in the experiments described in Section 6, infra, is indicated by the arrow labeled "A".

FIG. 5. The nucleotide sequence of EST R72810 (SEQ ID NO:9). The entire sequence is the prey sequence identified in Section 6 infra.

FIG. 9. The nucleotide sequence of EST R72810 and contiguous EST sequences (SEQ ID NO:10) is depicted. The original EST R72810 sequence is shown in bold lettering; a 5' extension was achieved with EST C17385 marked with underline; and 3' extensions were made, first from EST AA464793 indicated by boxed lettering, and second with EST AA479761 indicated by bold, italic lettering. The 5' of the prey interacting sequence denoted as "A"; the 3' end of the sequence is indicated by a starred arrow.

FIGS. 10A–F. The predicted open reading frames and translation of the open reading frames, in all three frames, of the nucleotide sequence of SEQ ID NO:10. (A and B). The C-terminus of 53BP2-IP3 (SEQ ID NO:13) is encoded in Translation Frame +1 at the 5' end of the assembled nucleotide sequence as depicted graphically in panel A. Panel B presents the nucleotide and predicted amino acid sequence of the C-terminus of 53BP2-IP3. (C and D). 53BP2-IP2 (SEQ ID NO:12) is encoded in translation Frame +2 from nucleotides 44–652, as depicted in panel C. Panel D presents the nucleotide and predicted amino acid sequence of 53BP2-IP2. (E and F). 53BP2-IP1 (SEQ ID NO:11) is encoded in translation Frame +2 from nucleotides 44–652, as depicted in panel E. Panel F presents the nucleotide and predicted amino acid sequence of 53BP2-IP1.

DETAILED DESCRIPTION OF THE INVENTION

Figure 6:
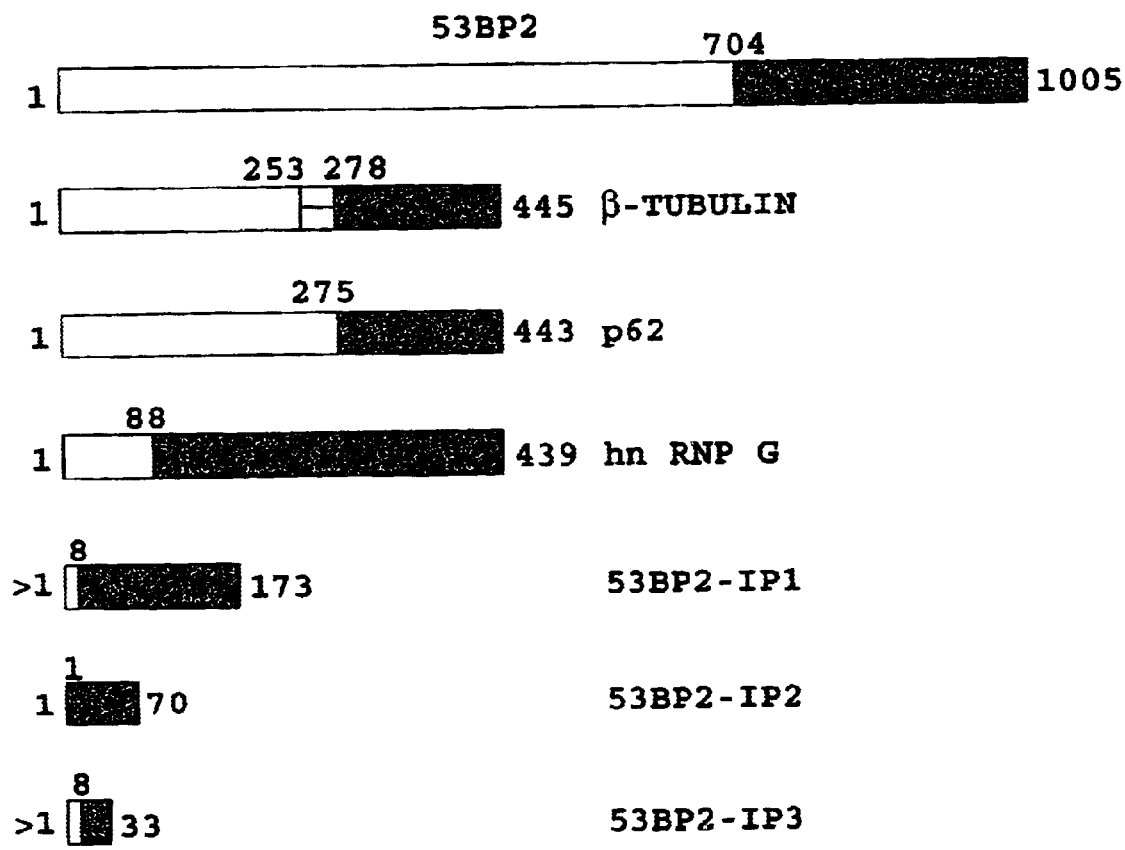
FIG. 6. Schematic of the portions of 53BP2, β-tubulin, p62, hnRNP G, and 53BP2-IP1/IP2/IP3 (i.e., the proteins potentially encoded, at least in part, by the extended EST R72810 sequence) that interact in a 53BP2:IP complex in the yeast two hybrid assay system. The sequences of 53BP2, β-tubulin, p62, hnRNP G and EST R78210 proteins are depicted as bars, with the starting and ending amino acid numbers (as depicted for each protein in FIGS. 1–4, 9 and 10A–F (SEQ ID NOS: 2, 4, 6, 8, 11, 12 and 13, respectively). The portions of each sequence either used as bait (in the case of 53BP2) or identified in the assay ("prey sequence") (in the case of β-tubulin, p62, hnRNP G and EST R78210 encoded proteins are blackened and the first amino acid number of the bait or prey sequence, as the case may be, is indicated above each bar. For β-tubulin, the N-terminal portion of a second, longer interacting sequence is indicated by a horizontal line (with the first amino acid of this extension indicated above the bar). For 53BP2-IP1 and 53BP2-IP3, the first amino acid is denoted by ">1", since the actual amino terminus is predicted to extend beyond the 5' end of the assembled nucleotide sequence.

The present invention is based upon the identification of proteins that interact with 53BP2 (termed herein "53BP2-IPs") using an improved, modified form of the yeast two hybrid system. β-tubulin, p62, hnRNP G, and 53BP2-IP1, 53BP2-IP2, and 53BP2-IP3 were found to form complexes under physiological conditions with 53BP2 (the complexes of 53BP2 with a 53BP2-IP are indicated as "53BP2:53BP2-IP" complexes herein). These 53BP2:53BP2-IP complexes, by virtue of the interaction, are implicated in modulating the functional activities of 53BP2 and its binding partners. Such functional activities include, but are not limited to, cell cycle control, transcriptional regulation, cellular apoptosis and differentiation, intracellular signal transduction, tumorigenesis and tumor progression, protein transport and cell structure, cell differentiation, cellular activation by c-Src, ubiquitin-mediated proteolysis, mRNA binding and metabolism, translational regulation, and autoimmune disease.

The present invention relates to methods of screening for proteins that interact with (e.g. bind to) 53BP2. The invention further relates to 53BP2 complexes, in particular 53BP2 complexes with one of the following proteins: β-tubulin, p62, hnRNP G, 53BP2-IP1, 53BP2-IP2 or 53BP2-IP3. The invention further relates to complexes of 53BP2 or derivatives, analogs and fragments of 53BP2 with β-tubulin, p62, hnRNP G, 53BP2-IP1, 53BP2-IP2, or 53BP2-IP3 derivatives, analogs and fragments thereof. In a preferred embodiment such complexes bind an anti-53BP2:53BP2-IP complex antibody. In a specific embodiment, complexes of 53BP2 with a protein that is not protein phosphatase I alpha (PPI alpha) or p53 are provided.

The invention also provides methods of producing and/or isolating the 53BP2:53BP2-IP complexes. In a specific embodiment, the invention provides methods of recombinantly expressing both 53BP2 and its binding partner (or fragments, derivatives or homologs of one or both members of the complex) either where both binding partners are under the control of one heterologous promoter (i.e. a promoter not naturally associated with the native gene encoding the particular complex component) or where each is under the control of a separate heterologous promoter.

In another aspect, the invention provides the nucleotide sequences of 53BP2-IP1, 53BP2-IP2, and 53BP2-IP3 and their encoded proteins. The invention further relates to 53BP2-IP1, 53BP2-IP2, and 53BP2-IP3 proteins, derivatives, fragments and homologs thereof, as well as nucleic acids encoding the 53BP2-IP1, 53BP2-IP2, and 53BP2-IP3 proteins, derivatives, fragments and homologs. The invention provides 53BP2-IP1, 53BP2-IP2, and 53BP2-IP3 proteins and genes encoding these proteins of many different species, particularly vertebrates, and more particularly mammals. In a preferred embodiment, the 53BP2-IP1, 53BP2-IP2 and 53BP2-IP3 proteins and genes are of human origin. Production of the foregoing proteins and derivatives, e.g., by recombinant methods, is provided.

The invention further relates to 53BP2-IP1, 53BP2-IP2, and 53BP2-IP3 derivatives and analogs which are functionally active, i.e., capable of displaying one or more known functional activities associated with a full length (wild-type) 53BP2-1P1, 53BP2-IP2, and 53BP2-IP3. Such functional activities include, but are not limited to, ability to form a complex with 53BP2, antigenicity [ability to bind (or compete with 53BP2-IP1, 53BP2-IP2, or 53BP2-IP3 for binding) to an anti-53BP2-IP1, anti-53BP2-IP2, or anti-53BP2-IP3 antibody, respectively], immunogenicity (ability to generate an antibody that binds to 53BP2-IP1, 53BP2-IP2, or 53BP2-IP3, respectively), etc.

Methods of diagnosis, prognosis, and screening for disease and disorders associated with aberrant levels of 53BP2:53BP2-IP complexes or of 53BP2-IP1, 53BP2-IP2 or 53BP2-IP3 are provided. The invention also provides methods of treating or preventing diseases or disorders associated with aberrant levels of 53BP2:53BP2-IP complexes or 53BP2-IP1, 53BP2-IP2, or 53BP2-IP3 or aberrant levels of the activity of one or more of the components of the complex by administration of the 53BP2:53BP2-IP complexes, 53BP2-IP1, 53BP2-IP2, 53BP2-IP3 or modulators of 53BP2:53BP2-IP complex formation or activity (e.g., antibodies that bind the 53BP2:53BP2-IP complex, uncomplexed 53BP2 or its binding partner or a fragment thereof—preferably the fragment containing the portion of 53BP2 or the 53BP2-IP that is directly involved in complex formation), mutants of 53BP2 or the 53BP2-IP that increase or decrease binding affinity, small molecule inhibitors/enhancers of complex formation, antibodies that either stabilize or neutralize the complex, etc.

Methods of assaying 53BP2:53BP2-IP complexes, 53BP2-IP1, 53BP2-IP2, or 53BP2-IP3 for activity as therapeutics or diagnostics as well as methods of screening for 53BP2:53BP2-IP complex, 53BP2-IP1, 53BP2-IP2 or 53BP2-IP3 modulators (i.e., inhibitors, agonists and antagonists) are also provided.

For clarity of disclosure, and not by way of limitation, the detailed description of the invention is divided into the subsections which follow.

BP2:1P Complexes and 53BP2-IP1, 53BP2-IP2 and 53BP2-IP3 Proteins and Derivatives and Anologs The invention provides 53BP2:53BP2-IP complexes, and, in particular aspects, complexes of 53BP2 and β-tubulin, 53BP2 and p62, 53BP2 and hnRNP G, 53BP2 and 53BP2-IP1, 53BP2 and 53BP2-IP2, and 53BP2 and 53BP2-IP3. In a preferred embodiment, 53BP2 is complexed with a protein that is not a PP1 alpha protein or a p53 protein. In another preferred embodiment, the 53BP2:53BP2-IP complexes are complexes of human proteins. The invention also relates to complexes of derivatives (including fragments) and analogs of 53BP2 with a 53BP2-IP, complexes of 53BP2 with derivatives (including fragments) and analogs of a 53BP2-IP, and complexes of derivatives (including fragments) and analogs of 53BP2 and a 53BP2-IP (as used herein, fragment, derivative or analog of a 53BP2:53BP2-IP complex includes complexes where one or both members of the complex are fragments, derivatives or analogs of the wild-type 53BP2 or 53BP2-IP protein). Preferably, the 53BP2:53BP2-IP complexes in which one or both members of the complex are a fragment, derivative or analog of the wild type protein are functionally active 53BP2:53BP2-IP complexes. In particular aspects, the native proteins, derivatives or analogs of 53BP2 and/or the 53BP2-IP are of animals, e.g. mouse, rat, pig, cow, dog, monkey, human, fly, frog, or of plants. "Functionally active 53BP2:53BP2-IP complex" as used herein refers to that material displaying one or more known functional attributes of a complex of full length 53BP2 with a full length 53BP2-IP (e.g., β-tubulin, p62, hnRNP G, 53BP2-IP1, 53BP2-IP2, or 53BP2-IP3) including but not exclusive to cell cycle control, modulation of cell apoptosis and differentiation, control of transcriptional and translational regulation, effects on intracellular signal transduction, protein transport, and c-Src activation, effects on tumorigenesis and tumor progression, ubiquitin-mediated proteolysis, effects on mRNA binding and metabolism, binding to an anti-53BP2:53BP2-IP complex antibody, etc., and other activities as they are described in the art. For example, such derivatives or analogs which have the desired immunogenicity or antigenicity can be used in immunoassays, for immunization, for inhibition of 53BP2:53BP2-IP complex activity, etc. Derivatives or analogs that retain, or alternatively lack or inhibit, a property of interest (e.g., participation in a 53BP2:53BP2-IP complex) can be used as inducers, or inhibitors, respectively, of such a property and its physiological correlates. A specific embodiment relates to a 53BP2:53BP2-IP complex of a fragment of 53BP2 and/or a fragment of 53BP2-IP that can be bound by an anti-53BP2 and/or 53BP2-IP antibody or antibody specific for a 53BP2:53BP2-IP complex when such a fragment is included within a 53BP2:53BP2-IP complex.

Fragments and other derivatives or analogs of 53BP2:53BP2-IP complexes can be tested for the desired activity by procedures known in the art, including but not limited to the assays described in Section 5.6.

In specific embodiments, the invention provides 53BP2:53BP2-IP complexes comprising fragments of one or both members of the complex. In a preferred embodiment, these fragments consist of, but are not exclusive to, the C-terminal domain of 53BP2 of amino acid 704–1005 (as depicted in FIG. 1 (SEQ ID NO:2)), and fragments of β-tubulin, p62, hnRNP G, 53BP2-IP1, 53BP2-IP2, or 53BP2-P3, of those regions identified as interacting with 53BP2 in the yeast two hybrid assay (e.g., amino acids 253–445 or 278–445 of β-tubulin as depicted in FIG. 2 (SEQ ID NO:4), amino acids 275–443 of p62 as depicted in FIG. 3 (SEQ ID NO:6), amino acids 88–439 of hnRNP G as depicted in FIG. 4 (SEQ ID NO:8), amino acids 8–173 of 53BP2-IP1 as depicted in FIG. 10F (SEQ ID NO:11), amino acids 1–70 of 53BP2-IP2 as depicted in FIG. 10D (SEQ ID NO:12), and amino acids 8–33 of 53BP2-IP3 as depicted in FIG. 10B (SEQ ID NO:13)). Fragments, or proteins comprising fragments, lacking some or all of the foregoing regions of either member of the complex assay, are also provided. Nucleic acids encoding the foregoing are provided.

The invention further relates to 53BP2-IP1, 53BP2-IP2, and 53BP2-IP3 proteins as well as derivatives (including but not limited to fragments) and homologs and paralogs of 53BP2-IP1, 53BP2-IP2, and 53BP2-IP3 proteins. In one embodiment human 53BP2-IP1, 53BP2-IP2, and 53BP2-IP3 genes and proteins are provided. In specific aspects, the native proteins, fragments, derivatives or analogs of 53BP2-IP1, 53BP2-IP2, or 53BP2-IP3 are of animals, e.g. mouse, rat, pig, cow, dog, monkey, human, fly, frog, or of plants. In other specific embodiments, the fragment, derivative or analog is functionally active, i.e., capable of exhibiting one or more functional activities associated with full-length, wild-type 53BP2-IP1, 53BP2-IP2, or 53BP2-IP3, e.g., ability to bind 53BP2, immunogenicity or antigenicity.

The nucleotide sequences encoding, and the corresponding amino acid sequences, of human 53BP2, β-tubulin, p62, and hnRNP G are known (GenBank Accession No. U58334; GenBank Accession No. X79535; GenBank Accession No. M88108; and GenBank Accession No. Z23064, respectively), and are provided in FIGS. 1–4, respectively (SEQ ID NOS:1, 3, 5, and 7, respectively). Nucleic acids encoding 53BP2, β-tubulin, p62 or hnRNP G can be obtained by any method known in the art, e.g, by PCR amplification using synthetic primers hybridizable to the 3' and 5' ends of the sequence and/or by cloning from a cDNA or genomic library using an oligonucleotide specific for the gene sequence (e.g., as described in Section 5.2, infra). Homologs (e.g., nucleic acids encoding 53BP2, β-tubulin, p62, and hnRNP G of species other than human) or other related sequences (e.g., paralogs) can be obtained by low, moderate or high stringency hybridization with all or a portion of the particular human sequence as a probe using methods well known in the art for nucleic acid hybridization and cloning (e.g., as described in Section 5.2, infra, for 53BP2-IP1, 53BP2-IP2, and 53BP2-IP3 sequences).

The 53BP2, β-tubulin, p62, hnRNP G, and 53BP2-IP1, 53BP2-IP2, or 53BP2-IP3 proteins, either alone or in a complex, can be obtained by methods well known in the art for protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter for 53BP2 or any 53BP2-IP genes, and/or their flanking regions.

A variety of host-vector systems may be utilized to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, the 53BP2:53BP2-IP complexes are obtained by expressing the entire 53BP2 sequence and a 53BP2-IP coding sequence in the same cell, either under the control of the same promoter or two separate promoters. In yet another embodiment, a derivative, fragment or homolog of 53BP2 and/or a derivative, fragment or homolog of a 53BP2-IP are recombinantly expressed. Preferably the derivative, fragment or homolog of 53BP2 and/or the 53BP2-IP protein forms a complex with a binding partner identified by a binding assay, such as the modified yeast two hybrid system described in Section 5.7.1 infra, more preferably forms a complex that binds to an anti-53BP2:53BP2-IP complex antibody.

Any of the methods described in Section 5.2 infra, for the insertion of DNA fragments into a vector may be used to construct expression vectors containing a chimeric gene consisting of appropriate transcriptional/translational control signals and protein coding sequences. These methods may include in vitro recombinant DNA and synthetic techniques and in vivo recombinants (genetic recombination). Expression of nucleic acid sequences encoding 53BP2 and a 53BP2-IP (e.g., β-tubulin, p62, hnRNP G, 53BP2-IP1, 53BP2-IP2, or 53BP2-IP3), or derivatives, fragments or homologs thereof, may be regulated by a second nucleic acid sequence so that the genes or fragments thereof are expressed in a host transformed with the recombinant DNA molecule(s). For example, expression of the proteins may be controlled by any promoter/enhancer known in the art. In a specific embodiment, the promoter is not native to the genes for 53BP2 or the 53BP2-IP. Promoters which may be used include but are not limited to the SV40 early promoter (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. USA 78: 1441–1445), the regulatory sequences of the metallothionein gene (Brinster et al., 1982, Nature 296: 39–42); prokaryotic expression vectors such as the β-lactamase promoter (Villa-Kamaroff et al., 1978, Proc. Natl. Acad. Sci. USA 75: 3727–3731) or the tac promoter (DeBoer et al., 1983, Proc. Natl. Acad. Sci. USA 80: 21–25; see also "Useful Proteins from Recombinant Bacteria": in Scientific American 1980, 242:79–94); plant expression vectors comprising the nopaline synthetase promoter (Herrar-Estrella et al., 1984, Nature 303: 209–213) or the cauliflower mosaic virus 35S RNA promoter (Garder et al., 1981, Nucleic Acids Res. 9:2871), and the promoter of the photosynthetic enzyme ribulose bisphosphate carboxylase (Herrera-Estrella et al., 1984, Nature 310: 115–120); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been utilized in transgenic animals: elastase I gene control region which is active in pancreatic acinar cells (Swift et al., 1984, Cell 38: 639–646; Ornitz et al., 1986, Cold Spring Harbor Symp. Quant. Biol. 50: 399–409; MacDonald 1987, Hepatology 7: 425–515); insulin gene control region which is active in pancreatic beta cells (Hanahan et al., 1985, Nature 315: 115–122), immunoglobulin gene control region which is active in lymphoid cells (Grosschedl et al., 1984, Cell 38: 647–658; Adams et al., 1985, Nature 318: 533–538; Alexander et al., 1987, Mol. Cell Biol. 7: 1436–1444), mouse mammary tumor virus control region which is active in testicular, breast, lymphoid and mast cells (Leder et al., 1986, Cell 45: 485–495), albumin gene control region which is active in liver (Pinckert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235: 53–58), alpha-1 antitrypsin gene control region which is active in liver (Kelsey et al., 1987, Genes and Devel. 1: 161–171), beta globin gene control region which is active in myeloid cells (Mogram et al., 1985, Nature 315: 338–340; Kollias et al., 1986, Cell 46: 89–94), myelin basic protein gene control region which is active in oligodendrocyte cells of the brain (Readhead et al., 1987, Cell 48: 703–712), myosin light chain-2 gene control region which is active in skeletal muscle (Sani 1985, Nature 314: 283–286), and gonadotrophic releasing hormone gene control region which is active in gonadotrophs of the hypothalamus (Mason et al., 1986, Science 234: 1372–1378).

In a specific embodiment, a vector is used that comprises a promoter operably linked to nucleic acid sequences encoding 53BP2 and/or a 53BP2-IP (e.g. β-tubulin, p62, hnRNP G, 53BP2-IP1, 53BP2-IP2 or 53BP2-IP3), or a fragment, derivative or homolog, thereof, one or more origins of replication, and optionally, one or more selectable markers (e.g., an antibiotic resistance gene). In a preferred embodiment, a vector is used that comprises a promoter operably linked to nucleic acid sequences encoding both 53BP2 and a 53BP2-IP, one or more origins of replication, and optionally, one or more selectable markers.

In another specific embodiment, an expression vector containing the coding sequences, or portions thereof, of 53BP2 and a 53BP2-IP (e.g., β-tubulin, p62, hnRNP G, 53BP2-IP1, 53BP2-IP2, or 53BP2-IP3), either together or separately, is made by subcloning the gene sequences into the EcoRI restriction site of each of the three PGEX vectors (glutathione S-transferase expression vectors; Smith and Johnson, 1988, Gene 7:31–40). This allows for the expression of products in the correct reading frame.

Expression vectors containing the sequences of interest can be identified by three general approaches: (a) nucleic acid hybridization, (b) presence or absence of "marker" gene function, and (c) expression of the inserted sequences. In the first approach, 53BP2, β-tubulin, p62, hnRNP G, 53BP2-IP1, 53BP2-IP2, 53BP2-IP3, or other 53BP2-IP sequences can be detected by nucleic acid hybridization to probes comprising sequences homologous and complementary to the inserted sequences. In the second approach, the recombinant vector/host system can be identified and selected based upon the presence or absence of certain "marker" functions (e.g., binding to an anti-53BP2, anti-53BP2-IP, or anti-53BP2:53BP2-IP complex antibody, resistance to antibiotics, occlusion body formation in baculovirus, etc.) caused by insertion of the sequences of interest in the vector. For example, if 53BP2 or a 53BP2-IP gene, or portion thereof, is inserted within the marker gene sequence of the vector, recombinants containing the 53BP2 or 53BP2-IP fragment will be identified by the absence of the marker gene function. In the third approach, recombinant expression vectors can be identified by assaying for the 53BP2, β-tubulin, p62, hnRNP G, 53BP2-IP1, 53BP2-IP2, 53BP2-IP3, or other 53BP2-IP products expressed by the recombinant vector. Such assays can be based, for example, on the physical or functional properties of the interacting species in in vitro assay systems, e.g., formation of a 53BP2:53BP2-IP complex, immunoreactivity to antibodies specific for the protein.

Once recombinant 53BP2, β-tubulin, p62, hnRNP G, 53BP2-IP1, 53BP2-IP2, or 53BP2-IP3, or other 53BP2-IP molecules are identified and the complexes or individual proteins isolated, several methods known in the art can be used to propagate them. Once a suitable host system and growth conditions have been established, recombinant expression vectors can be propagated and amplified in quantity. As previously described, the expression vectors or derivatives which can be used include, but are not limited to: human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered 53BP2 and/or 53BP2-IP may be controlled. Furthermore, different host cells have characteristic and specific mechanisms for the translational and post-translational processing and modification (e.g. glycosylation, phosphorylation, etc.) of proteins. Appropriate cell lines or host systems can be chosen to ensure the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extents.

In other specific embodiments, the 53BP2 and/or 53BP2-IPs or fragments, homologs or derivatives thereof, may be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes comprising portions of 53BP2 and/or a 53BP2-IP, or 53BP2-IP1, 53BP2-IP2, or 53BP2-IP3 fused to any heterologous protein-encoding sequences may be constructed. A specific embodiment relates to a chimeric protein comprising a fragment of 53BP2 and/or a 53BP2-IP, or 53BP2-IP1, 53BP2-IP2, or 53BP2-IP3 of at least six amino acids.

In a specific embodiment, fusion proteins are provided that contain the interacting domains of the 53BP2 protein and a 53BP2-IP (e.g., β-tubulin, p62, hnRNP G, 53BP2-IP1, 53BP2-IP2 or 53BP2-IP3) and, optionally, a peptide linker between the two domains, where such a linker promotes the interaction of the 53BP2 and 53BP2-IP binding domains. These fusion proteins may be particularly useful where the stability of the interaction is desirable (due to the formation of the complex as an intramolecular reaction), for example in production of antibodies specific to the 53BP2:53BP2-IP complex.

In particular, 53BP2 and/or 53BP2-IP or 53BP2-IP1, 53BP2-IP2, or 53BP2-IP3 derivatives can be made by altering their sequences by substitutions, additions or deletions that provide for functionally equivalent molecules. Due to the degeneracy of nucleotide coding sequences, other DNA sequences which encode substantially the same amino acid sequence as a 53BP2 or 53BP2-IP or 53BP2-IP1, 53BP2-IP2, or 53BP2-IP3 gene can be used in the practice of the present invention. These include but are not limited to nucleotide sequences comprising all or portions of 53BP2, β-tubulin, p62, hnRNP G, 53BP2-IP1, 53BP2-IP2, or 53BP2-IP3, or other 53BP2-IP genes that are altered by the substitution of different codons that encode a functionally equivalent amino acid residue within the sequence, thus producing a silent change. Likewise, the 53BP2, 53BP2-IP, 53BP2-IP1, 53BP2-IP2, and 53BP2-IP3 derivatives of the invention include, but are not limited to, those containing, as a primary amino acid sequence, all or part of the amino acid sequence of 53BP2 or a 53BP2-IP or 53BP2-IP1, 53BP2-IP2, or 53BP2-IP3, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, the nucleic acids encoding proteins and proteins consisting of or comprising a fragment of 53BP2 or a 53BP2-IP or 53BP2-IP1, 53BP2-IP2, or 53BP2-IP3 consisting of at least 6 (continuous) amino acids of 53BP2, a 53BP2-IP, 53BP2-IP1, 53BP2-IP2, or 53BP2-IP3 are provided. In other embodiments, the fragment consists of at least 10, 20, 30, 40, or 50 amino acids of 53BP2, 53BP2-IP, 53BP2-IP1, 53BP2-IP2, or 53BP2-IP3. In specific embodiments, such fragments are not larger than 35, 100 or 200 amino acids. Derivatives or analogs of 53BP2 and 53BP2-IPs or 53BP2-IP1, 53BP2-IP2, or 53BP2-IP3 include but are not limited to molecules comprising regions that are substantially homologous to 53BP2, 53BP2-IPs, 53BP2-IP1, 53BP2-IP2, or 53BP2-IP3 in various embodiments, at least 30%, 40%, 50%, 60%, 70%, 80%, 90% or 95% identity over an amino acid sequence of identical size or when compared to an aligned sequence in which the alignment is done by a computer homology program known in the art or whose encoding nucleic acid is capable of hybridizing to a sequence encoding 53BP2, a 53BP2-IP, 53BP2-IP1, 53BP2-IP2, or 53BP2-IP3 under stringent, moderately stringent, or nonstringent conditions.

The 53BP2, 53BP2-IP, 53BP2-IP1, 53BP2-IP2, and 53BP2-IP3 derivatives and analogs of the invention can be produced by various methods known in the art. The manipulations which result in their production can occur at the gene or protein level. For example, the cloned 53BP2, 53BP2-IP 53BP2-IP1, or 53BP2-IP2 gene sequence can be modified by any of numerous strategies known in the art (Maniatis, T., 1990, *Molecular Cloning, A Laboratory Manual*, 2d ed., Cold Spring Harbor Laboratory, Cold Spring Harbor, N.Y.). The sequences can be cleaved at appropriate sites with restriction endonuclease(s), followed by further enzymatic modification if desired, isolated, and ligated in vitro. In the production of the gene encoding a derivative or analog of 53BP2 or a 53BP2-IP care should be taken to ensure that the modified gene retains the original translational reading frame, uninterrupted by translational stop signals, in the gene region where the desired activity is encoded.

Additionally, the 53BP2 and/or 53BP2-IP-encoding nucleic acid sequence or 53BP2-IP1, 53BP2-IP2 or 53BP2-IP3-encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., 1978, J. Biol. Chem 253:6551–6558), use of TAB® linkers (Pharmacia), etc.

Once a recombinant cell expressing 53BP2 and/or a 53BP2-IP or 53BP2-IP1, 53BP2-IP2, or 53BP2-IP3 protein, or fragment or derivative thereof, is identified, the individual gene product or complex can be isolated and analyzed. This is achieved by assays based on the physical and/or functional properties of the protein or complex, including, but not limited to, radioactive labeling of the product followed by analysis by gel electrophoresis, immunoassay, crosslinking to marker-labeled product, etc.

The 53BP2:53BP2-IP complexes and 53BP2-IP1, 53BP2-IP2, and 53BP2-IP3 proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once a 53BP2-IP or its derivative is identified, the amino acid sequence of the protein can be deduced from the nucleic acid sequence of the chimeric gene from which it was encoded. As a result, the protein or its derivative can be synthesized by standard chemical methods known in the art (e.g. see Hunkapiller et al, 1984, Nature 310: 105–111).

In a specific embodiment of the present invention, such 53BP2:53BP2-IP complexes and 53BP2-IP1, 53BP2-IP2, and 53BP2-IP3 proteins, whether produced by recombinant DNA techniques, chemical synthesis methods, or by purification from native sources, include but are not limited to those containing, as a primary amino acid sequence, all or part of the amino acid sequences substantially as depicted in FIGS. 1–4, and 10B, D, and F (SEQ ID NOS:2, 4, 6, 8, 13, 12 and 11), as well as fragments and other analogs and derivatives thereof, including proteins homologous thereto.

Manipulations of 53BP2 and/or 53BP2-IP sequences or 53BP2-IP1, 53BP2-IP2, or 53BP2-IP3 sequences may be made at the protein level. Included within the scope of the invention are complexes of 53BP2 or 53BP2-IP fragments, derivatives or analogs and 53BP2-IP1, 53BP2-IP2, and 53BP2-IP3 fragments, derivatives and analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In specific embodiments, the 53BP2 and/or 53BP2-IP sequences are modified to include a fluorescent label. In another specific embodiment the 53BP2 and/or the 53BP2-IP are modified to have a heterofunctional reagent, such heterofunctional reagents can be used to crosslink the members of the complex.

In addition, complexes of analogs and derivatives of 53BP2 and/or a 53BP2-IP or analogs and derivatives of 53BP2-IP1, 53BP2-IP2, or 53BP2-IP3 can be chemically synthesized. For example, a peptide corresponding to a portion of 53BP2 and/or a 53BP2-IP or 53BP2-IP1, 53BP2-IP2 or 53BP2-IP3, which comprises the desired domain or which mediates the desired activity in vitro (e.g., 53BP2:53BP2-IP complex formation), can be synthesized by use of a peptide synthesizer. Furthermore, if desired, nonclassical amino acids or chemical amino acid analogs can be introduced as a substitution or addition into the 53BP2 and/or 53BP2-IP or 53BP2-IP1, 53BP2-IP2, or 53BP2-IP3 sequence. Non-classical amino acids include but are not limited to the D-isomers of the common amino acids, a-amino isobutyric acid, 4-aminobutyric acid, Abu, 2-aminobutyric acid, ε-Abu, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

In cases where natural products are suspected of being mutant or are isolated from new species, the amino acid sequence of 53BP2, a 53BP2-IP, 53BP2-IP1, 53BP2-IP2, or 53BP2-IP3 isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

The 53BP2:53BP2-IP complexes and 53BP2-IP1, 53BP2-IP2, or 53BP2-IP3 proteins may also be analyzed by hydrophilicity analysis (Hopp and Woods, 1981, Proc. Natl. Acad. Sci. USA 78: 3824–3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of the 53BP2 and/or a 53BP2-IP or 53BP2-IP1, 53BP2-IP2, or 53BP2-IP3 that assume specific structures (Chou and Fasman, 1974, Biochemistry 13: 222–23). Manipulation, translation, secondary structure prediction, hydrophilicity and hydrophobicity profiles, open reading frame prediction and plotting, and determination of sequence homologies, can be accomplished using computer software programs available in the art.

Other methods of structural analysis including but not limited to X-ray crystallography (Engstrom, 1974 Biochem. Exp. Biol. 11:7–13), mass spectroscopy and gas chromatography (Methods in Protein Science, J. Wiley and Sons, New York, 1997), and computer modeling (Fletterick and Zoller, eds., 1986, Computer Graphics and Molecular Modeling, In: *Current Communications in Molecular Biology*, Cold Spring Harbor Laboratory, Cold Spring Harbor Press, New York) can also be employed.

Identification and Isolation of 53BP2-IP1, 53BP2-IP2 and 53BP2-IP3 Genes

The invention relates to the nucleotide sequences of nucleic acids encoding 53BP2-IP1, 53BP2-IP2 and 53BP2-IP3. In specific embodiments, the 53BP2-IP1, 53BP2-IP2, and 53BP2-IP3 nucleic acids comprise the sequence of SEQ ID NO:10, or the coding regions thereof, or nucleotide sequences encoding, in whole or in part, a 53BP2-IP1, 53BP2-IP2, or 53BP2-IP3 protein (e.g., a protein comprising the sequence of SEQ ID NO:11, 12, or 13, respectively). The invention provides purified nucleic acids consisting of at least 8 nucleotides (i.e., a hybridizable portion) of a 53BP2-IP1, 53BP2-IP2, or 53BP2-IP3 sequence; in other embodiments, the nucleic acids consist of at least 25 (continuous) nucleotides, 50 nucleotides, 100 nucleotides, 150 nucleotides, or 200 nucleotides of a 53BP2-IP1, 53BP2-IP2, or 53BP2-IP3 sequence, or a full-length 53BP2-IP1, 53BP2-IP2, or 53BP2-IP3 coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences, in particular the invention provides the inverse complement to nucleic acids hybridizable to the foregoing sequences (i.e. the inverse complement of a nucleic acid strand has the complementary sequence running in reverse orientation to the strand so that the inverse complement would hybridize without mismatches to the nucleic acid strand; thus, for example, where the coding strand is hybridizable to a nucleic acid with no mismatches between the coding strand and the hybridizable strand, then the inverse complement of the hybridizable strand is identical to the coding strand). In specific aspects, nucleic acids are provided which comprise a sequence complementary to (specifically are the inverse complement of) at least 10, 25, 50, 100, or 200 nucleotides or the entire coding region of a 53BP2-IP1, 53BP2-IP2, or 53BP2-IP3 gene.

In a specific embodiment, a nucleic acid which is hybridizable to a 53BP2-IP1, 53BP2-IP2, or 53BP2-IP3 nucleic acid (e.g., having sequence SEQ ID NO:10), or to a nucleic acid encoding a 53BP2-IP1, 53BP2-IP2, or 53BP2-IP3 derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in-the same solution with the following modifications: 0.02% PVP, 0.02% Ficoll, 0.2% BSA, 100 gg/ml salmon sperm DNA, 10% (wt/vol) dextran sulfate, and 5–20×$10^6$ cpm $^{32}$P-labeled probe is used. Filters are incubated in hybridization mixture for 18–20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to a 53BP2-IP1, 53BP2-IP2, or 53BP2-IP3 nucleic acid under conditions of high stringency is provided. By way of example and not limitation, procedures using such conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 hours at 65° C. in prehybridization mixture containing 100 μg/ml denatured salmon sperm DNA and 5–20×$10^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50°

C. for 45 minutes before autoradiography. Other conditions of high stringency which may be used are well known in the art.

In another specific embodiment, a nucleic acid, which is hybridizable to a 53BP2-IP1, 53BP2-IP2, or 53BP2-IP3 nucleic acid under conditions of moderate stringency is provided. For example, but not limited to, procedures using such conditions of moderate stringency are as follows: Filters containing DNA are pretreated for 6 hours at 55° C. in a solution containing 6×SSC, 5×Denhart's solution, 0.5% SDS and 100 μg/ml denatured salmon sperm DNA. Hybridizations are carried out in the same solution and 5–20×10$^6$ cpm $^{32}$P-labeled probe is used. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS.

Nucleic acids encoding derivatives and analogs of 53BP2-IP1, 53BP2-IP2, or 53BP2-IP3 proteins (see Section 5.2), and 53BP2-IP1, 53BP2-IP2, or 53BP2-IP3 antisense nucleic acids (see Section 5.5.7) are additionally provided. As is readily apparent, as used herein, a "nucleic acid encoding a fragment or portion of a 53BP2-IP1, 53BP2-IP2 or 53BP2-IP3" shall be construed as referring to a nucleic acid encoding only the recited fragment or portion of 53BP2-IP1, 53BP2-IP2, or 53BP2-IP3 protein, and not the other contiguous portions of the 53BP2-IP1, 53BP2-IP2, or 53BP2-IP3 as a continuous sequence.

Fragments of 53BP2-IP1, 53BP2-IP2, or 53BP2-IP3 nucleic acids comprising regions conserved between (with homology to) other 53BP2-IP1, 53BP2-IP2, or 53BP2-IP3 nucleic acids, of the same or different species, are also provided.

Nucleic acids predicted to encode (at least in part) 53BP2-IP1, 53BP2-IP2, and 53BP2-IP3 were identified as encoding a protein or proteins that interact with 53BP2 using the improved version yeast two hybrid system (e.g. as described in Section 5.7.1 and exemplified in Section 6.1 supra). The present inventors found that the 5' end of this identified nucleic acid (illustrated in FIG. 9) has a nucleotide sequence identical to the nucleotide sequence of the EST sequence EST R72810.

EST sequences are part of human DNA databases such as the GenBank database "dbest". These sequences typically represent incomplete fragments of putative genes not yet ascribed to encode a known protein or RNA species. These sequences generally do not encode a full-length protein because they generally (1) lack a methionine codon to act as a site of translational initiation; (2) lack a translational stop codon; or (3) do not contain an open reading frame to code for a protein longer than approximately 60 amino acids (shorter than the smallest known translated protein). The EST databases contain many overlapping sequences. Thus, it is possible to find contiguous sequences to assemble a longer sequence representative of a larger original sequence found in nature. Common in silico procedures known in the art, including use of the "BLAST" family of programs available through the National Center for Biotechnology Information (N.C.B.I.), can be used to detect homologies between nucleic acid sequences in the databases. To account for sequencing errors, silent mutations, etc., present in the database, a significant homology can be defined as 100%, 99%, 98%, 97%, 96%, 95% or some lesser level over a span of 20, 25, 30, 35, 40 or greater span of nucleotide overlap. The homology detection paradigm may allow for a limited number of single or, at most, double nucleotide insertion or deletion mismatches, particularly in regions of sequences known to be difficult to sequence, such as very high GC regions, multiple G residues, etc.

These in silico procedures allow for the "assembly" of two sequences that overlap nonidentical spans of a common sequence. This assembled sequence, in turn, is used to identify further related sequences by the same procedure. The 5' and 3' ends of the assembled sequence are extended until significant homology to sequences within available databases cannot be detected. The assembled EST sequence can be subjected to a final search of available databases to detect homologies to known protein sequences that were not detected over the shorter span of the original EST sequence.

Figures 7, 8:
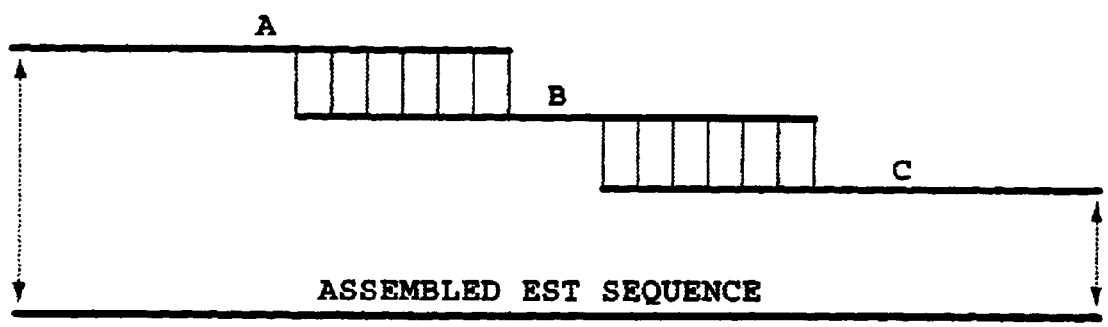
FIG. 7. Matrix of results of yeast two hybrid system assays. The results of assays using yeast expressing hybrids of the bait proteins B1, MDM2 and 53BP2 are indicated in the rows designated B1, MDM2 and 53BP2 mated with yeast cells expressing hybrids of the prey proteins P1, P2, PP1α, p62 and β-tubulin ("β-tub."), as indicated by the rows designated as P1, P2, PP1α, p62 and β-tub, are depicted. A positive interaction for a bait and prey proteins is indicated as "+" in the box forming the intersection between the particular bait and prey proteins; a lack of interaction is designated by an empty box. Boxes labeled A, B, C and D indicate the results of matings of yeast expressing B1 and PP1α, 53BP2 and PP1α, 53BP2 and p62, and 53BP2 and β-tubulin, respectively.
FIG. 8. This figure illustrates the general procedure used to assemble the longest possible contiguous nucleic acid sequence from a particular EST sequence. The starting EST nucleic acid sequence, shown as the line labeled above as B, is run through the N.C.B.I. "BLAST" Program, and compared to all sequences in the "nr" database. Sequences that align with 95% or greater identity at the nucleic acid level over their termini of at least 30 bases are utilized if the alignment will result in 5' extension (Sequence A) or 3' extension (Sequence C) of the starting EST sequence.

The present inventors identified several EST sequences that overlap with EST R72810 at both the 5' and 3' termini. These sequences were assembled as described in Section 6.3 infra and as depicted in FIGS. 8 and 9.

The assembled EST sequence can be analyzed by a number of nucleic acid analysis programs available in the art to define possible protein translation products of the assembled nucleic acid sequence. Translation in all six phases will define possible open reading frames (contiguous spans of codons for amino acids without the presence of a stop codon). In the case where EST sequences are derived from directionally cloned libraries, only the three forward (5' to 3') translations are required because the sense, or coding strand, of the EST is already defined. The presence of ATG codons that define possible sites of initiation of protein translation identify the beginning of such an open reading frame. If an open reading frame extends to the 5' end of the assembled nucleic acid sequence is longer than 60 amino acid residues, the assembled EST sequence encodes a potential C-terminus of a protein within that reading frame, i.e., a protein that is missing one or more N-terminal amino acids.

In silico analysis of the assembled sequence revealed three possible translation products, 53BP2-IP1 (for 53BP2-Interacting Protein 1), 53BP2-IP2 (for 53BP2-Interacting Protein 2), and 53BP2-IP3 (for 53BP2-Interacting Protein 3).

Any method available in the art can be used to obtain a full length (i.e., encompassing the entire coding region) cDNA or genomic DNA clone encoding 53BP2-IP1 and/or 53BP2-IP2 and/or 53BP2-IP3. In particular, the polymerase chain reaction (PCR) can be used to amplify the sequence assembled from the EST sequences in a genomic or cDNA library. Oligonucleotide primers that hybridize to sequences at the 3' and 5' termini of the assembled EST sequences can be used as primers to amplify by PCR sequences from a nucleic acid sample (RNA or DNA), preferably a cDNA library, from an appropriate source (e.g. the sample from which the initial CDNA library for the yeast two hybrid assay fusion population was derived).

PCR can be carried out., e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain 53BP2-IP1, 53BP2-IP2 and 53BP2-IP3 sequences from species other than humans or to obtain human sequences with homology to 53BP2-IP1 and/or 53BP2-IP2 and/or 53BP2-IP3) by allowing for greater or lesser degrees of nucleotide sequence similarity between the known nucleotide sequence and the nucleic acid homolog being isolated. For cross species hybridization, low stringency conditions are preferred. For same species hybridization, moderately stringent conditions are preferred.

After successful amplification of the nucleic acid containing all or a portion of the sequence assembled from the EST sequences or of a nucleic acid encoding all or a portion of a 53BP2-IP1, 53BP2-IP2, or 53BP2-IP3 homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, the nucleotide sequences of the entire 53BP2-IP1, 53BP2-IP2, or 53BP2-IP3 genes as well as additional genes encoding 53BP2-IP1, 53BP2-IP2, or 53BP2-IP3 proteins and analogs may be identified.

Any eukaryotic cell potentially can serve as the nucleic acid source for the molecular cloning of the 53BP2-IP1, 53BP2-IP2, or 53BP2-IP3 gene. The nucleic acids can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a portion of the 53BP2-IP1, 53BP2-IP2, or 53BP2-IP3 (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available or by DNA sequence analysis and comparison to the known nucleotide sequence of 53BP2-IP1/53BP2-IP2/53BP2-IP3. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, or antigenic properties or ability to bind 53BP2, as known for 53BP2-IP1, 53BP2-IP2, or 53BP2-IP3. If an anti-53BP2-IP1, anti-53BP2-IP2 or anti-53BP2-IP3 antibody is available, the protein may be identified by binding of labeled antibody to the putatively 53BP2-IP1, 53BP2-IP2, or 53BP2-IP3 synthesizing clones, in an ELISA (enzyme-linked immunosorbent assay)-type procedure.

Alternatives to isolating the 53BP2-IP1, 53BP2-IP2, or 53BP2-IP3 genomic DNA include, but are not limited to, chemically synthesizing the gene sequence itself from a known sequence or making cDNA to the mRNA that encodes the 53BP2-IP1, 53BP2-IP2, or 53BP2-IP3 protein. For example, RNA for cDNA cloning of the 53BP2-IP1, 53BP2-IP2, or 53BP2-IP3 gene can be isolated from cells expressing the protein. Other methods are possible and within the scope of the invention.

The identified and isolated nucleic acids can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and 53BP2-IP1, 53BP2-IP2, or 53BP2-IP3 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated 53BP2-IP1, 53BP2-IP2, or 53BP2-IP3 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The 53BP2-IP1, 53BP2-IP2, or 53BP2-IP3 sequences provided by the instant invention include those nucleotide sequences encoding substantially the same amino acid sequences as found in native 53BP2-IP1, 53BP2-IP2, or 53BP2-IP3 proteins, and those encoded amino acid sequences with functionally equivalent amino acids, as well as those encoding other 53BP2-IP1, 53BP2-IP2 or 53BP2-IP3 derivatives or analogs, as described in Section 5.1 supra for 53BP2-IP1, 53BP2-IP2, or 53BP2-IP3 derivatives and analogs.

Antibodies to 53BP2:53BP2-IP Complexes, 53BP2-IP1, 53BP2-IP2, and 53BP2-IP3 Protiens According to the invention, the 53BP2:53BP2-IP complexes (e.g. 53BP2-IP complexes with β-tubulin, p62, hnRNP G, 53BP2-IP1, 53BP2-IP2, or 53BP2-IP3), or fragments, derivatives or homologs thereof, or 53BP2-IP1, 53BP2-IP2, or 53BP2-IP3 protein and fragments, homologs and derivatives thereof may be used as immunogens to generate antibodies which immunospecifically bind such immunogens. Such antibodies include but are not limited to polyclonal, monoclonal, chimeric, single chain, Fab fragments, and an Fab expression library. In a specific embodiment, antibodies to complexes of human 53BP2 and human 53BP2-IPs are produced. In another embodiment, complexes formed from fragments of 53BP2 and a 53BP2-IP, which fragments contain the protein domain that interacts with the other member of the complex, are used as immunogens for antibody production. In another specific embodiment, 53BP2-IP1, 53BP2-IP2, or 53BP2-IP3 or fragments, derivatives, or homologs thereof are used as immunogens.

Various procedures known in the art may be used for the production of polyclonal antibodies to a 53BP2:53BP2-IP complex, derivative or analog, or 53BP2-IP1, 53BP2-IP2, or 53BP2-IP3 protein, derivatives, fragments or analogs.

For production of the antibody, various host animals can be immunized by injection with the native 53BP2:53BP2-IP complex, or 53BP2-IP1, 53BP2-IP2, or 53BP2-IP3 protein or a synthetic version, or a derivative of the foregoing, such as a cross-linked 53BP2:53BP2-IP, such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and corynebacterium parvum.

For preparation of monoclonal antibodies directed towards a 53BP2:53BP2-IP complex or 53BP2-IP1, 53BP2-IP2, or 53BP2-IP3 or derivatives, fragments or analogs thereof, any technique that provides for the production of antibody molecules by continuous cell lines in culture may be used. Such techniques include but are not restricted to the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030). Or by transforming human B cells with EBV virus in vitro (Cole et al., 1985, in *Monoclonal Antibodies and Cancer Therapy*, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the 53BP2:53BP2 complex or 53BP2-IP1, or 53BP2-IP2 protein together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce 53BP2:53BP2-IP complex-specific and 53BP2-IP1, 53BP2-IP2, and 53BP2-IP3-specific single chain antibodies. An additional embodiment of the invention utilizes the techniques described for the construction of Fab expression libraries (Huse et al., 1989, Science 246: 1275–1281) to allow rapid and easy identification of monoclonal Fab fragments with the desired specificity for 53BP2: β-tubulin, p62, hnRNP G, 53BP2-IP1, 53BP2-IP2, or 53BP2-IP3 complexes, or 53BP2-IP1, 53BP2-IP2 or 53BP2-IP3 derivatives, or analogs thereof. Non-human antibodies can be "humanized" by known methods (see, e.g., U.S. Pat. No. 5,225,539).

Antibody fragments that contain the idiotypes of 53BP2:53BP2-IP complexes or of 53BP2-IP1, 53BP2-IP2, or 53BP2-IP3 can be generated by techniques known in the art. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the 53BP2:53BP2 complex or 53BP2-IP1, 53BP2-IP2, or 53BP2-IP3 one may assay generated hybridomas for a product that binds to the fragment of the 53BP2:53BP2-IP complex or 53BP2-IP1, 53BP2-IP2, or 53BP2-IP3 that contains such a domain. For selection of an antibody that specifically binds a 53BP2:53BP2-IP complex but which does not specifically bind to the individual proteins of the 53BP2-IP complex, one can select on the basis of positive binding to the 53BP2:53BP2-IP complex and a lack of binding to the individual 53BP2 and 53BP2-IP proteins.

Antibodies specific to a domain of the 53BP2:53BP2-IP complex are also provided, as are antibodies to specific domains of 53BP2-IP1, 53BP2-IP2, and 53BP2-IP3.

The foregoing antibodies can be used in methods known in the art relating to the localization and/or quantitation of 53BP2:53BP2-IP complexes and 53BP2-IP1, 53BP2-IP2, and 53BP2-IP3 proteins of the invention, e.g., for imaging these proteins, measuring levels thereof in appropriate physiological samples, in diagnostic methods, etc.

In another embodiment of the invention (see infra), anti-53BP2:53BP2-IP complex antibodies and fragments thereof, or anti-53BP2-IP1, anti-53BP2-IP2, and anti-53BP2-IP3 or fragments thereof, containing the binding domain, are Therapeutics.

Diagnostic, Prognostic, and Screening Uses of 53BP2:53BP-IP Complexes and 53BP2-IP1, 53BP2-IP2, and 53BP2-IP3 Protiens 53BP2:53BP2-IP complexes (particularly 53BP2 complexed with β-tubulin, p62, hnRNP G, 53BP2-IP1, 53BP2-

IP2, or 53BP2-IP3), or 53BP2-IP1, 53BP2-IP2, or 53BP2-IP3 proteins, may be markers of specific disease states involving disruption of cell cycle progression, cellular apoptosis and/or differentiation, intracellular signal transduction, protein transport, and/or c-Src activation, transcriptional or translational regulation, tumorigenesis and tumor progression, ubiquitin-mediated proteolysis, mRNA binding and metabolism, and effects on autoimmune processes, and thus have diagnostic utility. Further, definition of particular groups of patients with elevations or deficiencies of a 53BP2:53BP-IP complex or 53BP2-IP1, 53BP2-IP2, or 53BP2-IP3 protein can lead to new nosological classifications of diseases, furthering diagnostic ability.

Detecting levels of 53BP2:53BP-IP complexes, or individual proteins that have been shown to form complexes with 53BP2, or the 53BP2-IP1, 53BP2-IP2, or 53BP2-IP3 proteins, or detecting levels of the mRNA encoding the components of the 53BP2-IP:53BP2-IP complexes, or the 53BP2-IP1, 53BP2-IP2, or 53BP2-IP3 proteins may be used in prognosis, to follow the course of disease states, to follow therapeutic response, etc. 53BP2:53BP2-IP complexes and the individual components of the 53BP2:53BP2-IP complexes (e.g., 53BP2, β-tubulin, p62, hnRNP G, 53BP2-IP1, 53BP2-IP2, and 53BP2-IP3), and derivatives, analogs and subsequences thereof, 53BP2 and/or 53BP2-IP, 53BP2-IP1, 53BP2-IP2, and 53BP2-IP3 nucleic acids (and sequences complementary thereto), and anti-53BP2:53BP2-IP complex antibodies and antibodies directed against the individual components that can form 53BP2:53BP2-IP complexes and anti-53BP2-IP1, anti-53BP2-IP2, and anti-53BP2-IP3 antibodies, have uses in diagnostics. Such molecules can be used in assays, such as immunoassays, to detect, prognose, diagnose, or monitor various conditions, diseases, and disorders characterized by aberrant levels of 53BP2:53BP2-IP complexes or 53BP2-IP1, 53BP2-IP2, or 53BP2-IP3 proteins, or monitor the treatment thereof. In a specific embodiment, a 53BP2:53BP2-IP complex is detected that is not a complex of 53BP2 and PP1 or a complex of 53BP2 and p53.

In particular, such an immunoassay is carried out by a method comprising contacting a sample derived from a patient with an anti-53BP2:53BP2-IP complex antibody or anti-53BP2-IP1, anti-53BP2-IP2, or anti-53BP2-IP3 antibody under conditions such that immunospecific binding can occur, and detecting or measuring the amount of any immunospecific binding by the antibody. In a specific aspect, such binding of antibody, in tissue sections, can be used to detect aberrant 53BP2:53BP2-IP complex or 53BP2-IP1, 53BP2-IP2, or 53BP2-IP3 protein localization or aberrant (e.g., high, low or absent) levels of 53BP2:53BP2-IP complex or complexes or 53BP2-IP1, 53BP2-IP2, or 53BP2-IP3. In a specific embodiment, antibody to 53BP2:53BP2-IP complex can be used to assay in a patient tissue or serum sample for the presence of 53BP2:53BP2-IP complex where an aberrant level of 53BP2:53BP2-IP complex is an indication of a diseased condition. In another embodiment, antibody to 53BP2-IP1, 53BP2-IP2, or 53BP2-IP3 can be used to assay in a patient tissue or serum sample for the presence of 53BP2-IP1, 53BP2-IP2, or 53BP2-IP3 where an aberrant level of 53BP2-IP1, 53BP2-IP2, or 53BP2-IP3 is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Nucleic acids encoding the components of the 53BP2:53BP2-IP complexes (e.g., 53BP2, β-tubulin, p62, hnRNP G, 53BP2-IP1, 53BP2-IP2, and 53BP2-IP3) and the 53BP2-IP1, 53BP2-IP2, and 53BP2-IP3 proteins and related nucleic acid sequences and subsequences, including complementary sequences, can also be used in hybridization assays. The 53BP2, 53BP2-IP, 53BP2-IP1, 53BP2-IP2, and 53BP2-IP3 nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant levels of the mRNAs encoding the components of a 53BP2:53BP2-IP complex or 53BP2-IP1, 53BP2-IP2, or 53BP2-IP3 protein as described supra. In particular, such a hybridization assay is carried out by a method comprising contacting a sample containing nucleic acid with a nucleic acid probe capable of hybridizing to 53BP2, a 53BP2-IP, or 53BP2-IP1, 53BP2-IP2, or 53BP2-IP3 DNA or RNA (including cDNA prepared from mRNA from a sample), under conditions such that hybridization can occur, and detecting or measuring any resulting hybridization. In a preferred aspect, the hybridization assay is carried out using nucleic acid probes capable of hybridizing to 53BP2 and to a binding partner of 53BP2 (e.g. β-tubulin, p62, hnRNP G, 53BP2-IP1, 53BP2-IP2, or 53BP2-IP3) to measure concurrently the expression of both members of a 53BP2:53BP2-IP complex.

In specific embodiments, diseases and disorders involving or characterized by aberrant levels of 53BP2:53BP2-IP complexes (e.g., complexes of 53BP2 with β-tubulin, p62, hnRNP G, 53BP2-IP1, 53BP2-IP2, or 53BP2-IP3) can be diagnosed, or their suspected presence can be screened for, or a predisposition to develop such disorders can be detected, by detecting aberrant levels of 53BP2:53BP2-IP complexes, or uncomplexed 53BP2 and/or 53BP2-IP (e.g. β-tubulin, p62, hnRNP G, 53BP2-IP1, 53BP2-IP2, or 53BP2-IP3) proteins or nucleic acids or functional activity including but not restricted to binding to an interacting partner (e.g. 53BP2, β-tubulin, p62, hnRNP G, 53BP2-IP1, 53BP2-IP2, or 53BP2-IP3), or by detecting mutations in 53BP2 and/or a 53BP2-IP RNA, DNA or protein (e.g., translocations, truncations, changes in nucleotide or amino acid sequence relative to wild-type 53BP2 and/or the 53BP2-IP) that cause increased or decreased expression or activity of a 53BP2:53BP2-IP complex and/or 53BP2 and/or a protein that binds to 53BP2. Such diseases and disorders include but are not limited to those described in Section 5.5 and its subsections.

By way of example, levels of 53BP2:53BP2-IP complexes and the individual components of 53BP2:53BP2-IP components can be detected by immunoassay, levels of 53BP2 and/or 53BP2-IP RNA can be detected by hybridization assays (e.g., Northern blots, dot blots), binding of 53BP2 to a 53BP2-IP can be done by binding assays commonly known in the art, translocations and point mutations in 53BP2 and/or in genes encoding 53BP2-IPs can be detected by Southern blotting, RFLP analysis, PCR using primers that preferably generate a fragment spanning at least most of the 53BP2 and/or 53BP2-IP gene, sequencing of the 53BP2 and/or 53BP2-IP genomic DNA or cDNA obtained from the patient, etc.

Assays well known in the art (e.g. assays described above such as immunoassays, nucleic acid hybridization assays, activity assays, etc.) can be used to determine whether one or more particular 53BP2:53BP2-IP complexes are present at either increased or decreased levels or are absent in samples from patients suffering from a particular disease or disorder or having a predisposition to develop such a disease or disorder as compared to the levels in samples from subjects not having such a disease or disorder. Additionally, these assays can be used to determine whether the ratio of the 53BP2:53BP2-IP complex to the uncomplexed components of the 53BP2:53BP2-IP complex, i.e. 53BP2 and/or the specific 53BP2-IP in the complex of interest (e.g., β-tubulin, p62, hnRNP G, 53BP2-IP1, 53BP2-IP2, or 53BP2-IP3) is increased or decreased in samples from patients suffering from a particular disease or disorder or having a predisposition to develop such a disease or disorder as compared to the ratio in samples from subjects not having such a disease or disorder. In the event that levels of one or more particular 53BP2:53BP2-IP complexes are determined to be increased in patients suffering from a particular disease or disorder or having a predisposition to develop such a disease or disorder, then the particular disease or disorder or predisposition for a disease or disorder can be diagnosed, prognosed, screened for, or monitored by detecting increased levels of the one or more 53BP2:53BP2-IP complexes, the mRNA that encodes the members of the one or more particular 53BP2:53BP2-IP complexes (including detecting the corresponding in cDNA prepared from an mRNA sample), or 53BP2:53BP2-IP complex functional activity.

Accordingly, in a specific embodiment of the invention, diseases and disorders involving increased levels of one or more 53BP2:53BP2-IP complexes can be diagnosed, or their suspected presence can be screened for, or a predisposition to develop such disorders can be detected, by detecting increased levels of the one or more 53BP2:53BP2-IP complexes, the mRNA encoding both members of the complex, or complex functional activity, or by detecting mutations in 53BP2 or the 53BP2-IP (e.g., translocations in nucleic acids, truncations in the gene or protein, changes in nucleotide or amino acid sequence relative to wild-type 53BP2 or the 53BP2-IP) that inhibit 53BP2:53BP2-IP complex formation.

In the event that levels of one or more particular 53BP2:53BP2-IP complexes are determined to be decreased in patients suffering from a particular disease or disorder or having a predisposition to develop such a disease or disorder, then the particular disease or disorder or predisposition for a disease or disorder can be diagnosed, prognosed, screened for, or monitored by detecting decreased levels of the one or more 53BP2:53BP2-IP complexes, the mRNA that encodes the members of the particular one or more 53BP2:53BP2-IP complexes, or 53BP2:53BP2-IP complex functional activity.

Accordingly, in a specific embodiment of the invention, diseases and disorders involving decreased levels of one or more 53BP2:53BP2-IP complexes can be diagnosed, or their suspected presence can be screened for, or a predisposition to develop such disorders can be detected, by detecting decreased levels of the one or more 53BP2:53BP2-IP complexes, the mRNA encoding the members of the one or more complexes, or complex functional activity, or by detecting mutations in 53BP2 or the 53BP2-IP (e.g., translocations in nucleic acids, truncations in the gene or protein, changes in nucleotide or amino acid sequence relative to wild-type 53BP2 or the 53BP2-IP) that stabilize or enhance 53BP2:53BP2-IP complex formation.

In another specific embodiment, diseases and disorders involving aberrant expression of 53BP2-IP1, 53BP2-IP2, or 53BP2-IP3 are diagnosed, or their suspected presence can be screened for, or a predisposition to develop such disorders can be detected, by detecting aberrant levels of 53BP2-IP1, 53BP2-IP2, or 53BP2-IP3 protein, RNA, or functional activity, or by detecting mutations in 53BP2-IP1, 53BP2-IP2, or 53BP2-IP3 RNA, DNA or protein (e.g., translocations in nucleic acids, truncations in the gene or protein, changes in nucleotide or amino acid sequence relative to wild-type 53BP2-IP1, 53BP2-IP2, or 53BP2-IP3) that cause aberrant expression or activity of 53BP2-IP1, 53BP2-IP2, or 53BP2-IP3. Such diseases and disorders include but are not limited to those described infra Section 5.5. By way of example, levels of 53BP2-IP1, 53BP2-IP2, or 53BP2-IP3 RNA and protein, 53BP2 binding activity, and the presence of translocations or point mutations, can be determined as described above.

Assays well known in the art (e.g. assays described above such as immunoassays, nucleic acid hybridization assays, activity assays, etc.) can be used to determine whether 53BP2-IP1, 53BP2-IP2, or 53BP2-IP3 is present at either increased or decreased levels or is absent in samples from patients suffering from a particular disease or disorder or having a predisposition to develop such a disease or disorder as compared to the levels in samples from subjects not having such a disease or disorder. In the event that levels of 53BP2-IP1, 53BP2-IP2, or 53BP2-IP3 are determined to be increased in patients suffering from a particular disease or disorder or having a predisposition to develop such a disease or disorder, then the particular disease or disorder or predisposition for a disease or disorder can be diagnosed, prognosed, screened for, or monitored by detecting increased levels of 53BP2-IP1, 53BP2-IP2, or 53BP2-IP3 protein or mRNA, or 53BP2-IP1, 53BP2-IP2, or 53BP2-IP3 functional activity (e.g. binding to 53BP2).

Accordingly, in a specific embodiment of the invention, diseases and disorders involving increased levels of 53BP2-IP1, 53BP2-IP2, or 53BP2-IP3 can be diagnosed, or their suspected presence can be screened for, or a predisposition to develop such disorders can be detected, by detecting increased levels of 53BP2-IP1, 53BP2-IP2, or 53BP2-IP3 proteins or nucleic acids of 53BP2-IP1, 53BP2-IP2, or 53BP2-IP3 functional activity, or by detecting mutations in 53BP2-IP1, 53BP2-IP2, or 53BP2-IP3 (e.g., translocations in nucleic acids, truncations in the gene or protein, changes in nucleotide or amino acid sequence relative to wild-type 53BP2-IP1, 53BP2-IP2, or 53BP2-IP3) that inhibit 53BP2-IP1, 53BP2-IP2, or 53BP2-IP3 functional activity.

In the event that levels of 53BP2-IP1, 53BP2-IP2, or 53BP2-IP3 are determined to be decreased in patients suffering from a particular disease or disorder or having a predisposition to develop such a disease or disorder, then the particular disease or disorder or predisposition for a disease or disorder can be diagnosed, prognosed, screened for, or monitored by detecting decreased levels of the 53BP2-IP1, 53BP2-IP2, or 53BP2-IP3 proteins or nucleic acids, or 53BP2-IP1, 53BP2-IP2, or 53BP2-IP3 functional activity.

Accordingly, in a specific embodiment of the invention, diseases and disorders involving decreased levels of 53BP2-IP1, 53BP2-IP2, or 53BP2-IP3 can be diagnosed, or their suspected presence can be screened for, or a predisposition to develop such disorders can be detected, by detecting decreased levels of 53BP2-IP1, 53BP2-IP2, or 53BP2-IP3, the mRNA encoding 53BP2-IP1, 53BP2-IP2, or 53BP2-IP3 (including detecting the corresponding cDNA of mRNA in cDNA prepared from an mRNA sample), or complex functional activity, or by detecting mutations in 53BP2-IP1, 53BP2-IP2, or 53BP2-IP3 (e.g., translocations in nucleic acids, truncations in the gene or protein, changes in nucleotide or amino acid sequence relative to wild-type 53BP2-IP1, 53BP2-IP2, or 53BP2-IP3) that stabilize or enhance 53BP2:53BP2-IP complex formation.

The use of detection techniques, especially those involving antibodies against the 53BP2:53BP2-IP complexes or 53BP2-IP1, 53BP2-IP2, or 53BP2-IP3 proteins, provides a method of detecting specific cells that express the complex or protein. Using such assays, specific cell types can be defined in which one or more particular 53BP2:53BP2-IP complexes, or 53BP2-IP1, 53BP2-IP2, or 53BP2-IP3 protein are expressed, and the presence of the complex or protein can be correlated with cell viability.

Also embodied are methods to detect a 53BP2:53BP2-IP complex, or 53BP2-IP1, 53BP2-IP2, or 53BP2-IP3 protein, in cell culture models that express particular 53BP2:53BP2-IP complexes or 53BP2-IP1, 53BP2-IP1, or 53BP2-IP3 or derivatives thereof, for the purpose of characterizing or preparing 53BP2:53BP2-IP complexes, or 53BP2-IP1, 53BP2-IP2, or 53BP2-IP3 for harvest. This embodiment includes cell sorting of prokaryotes such as but not restricted to bacteria (Davey and Kell, 1996, Microbiol. Rev. 60: 641–696), primary cultures and tissue specimens from eukaryotes, including mammalian species such as human (Steele et al., 1996, Clin. Obstet. Gynecol 39: 801–813), and continuous cell cultures (Orfao and Ruiz-Arguelles, 1996, Clin. Biochem. 29: 5–9).

Kits for diagnostic use are also provided, that comprise in one or more containers an anti-53BP2:53BP2-IP complex antibody or an anti-53BP2-IP1, anti-53BP2-IP2, or anti-53BP2-IP3 antibody, and, optionally, a labeled binding partner to the antibody. Alternatively, the anti-53BP2:53BP2-IP complex antibody or anti-53BP2-IP1, anti-53BP2-IP2, or anti-53BP2-IP3 antibody can be labeled (with a detectable marker, e.g., a chemiluminescent, enzymatic, fluorescent, or radioactive moiety). A kit is also provided that comprises in one or more containers a nucleic acid probe capable of hybridizing to 53BP2 and/or a 53BP2-IP (e.g., β-tubulin, p62, hnRNP G, 53BP2-IP1, 53BP2-IP2, or 53BP2-IP3) RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, *PCR Protocols*, Academic Press, Inc., San Diego, Calif.), ligase chain reaction (see EP 320,308) use of Qβ replicase, cyclic probe reaction, or other methods known in the art), under appropriate reaction conditions of at least a portion of a 53BP2 and/or a 53BP2-IP or 53BP2-IP1, 53BP2-IP2, or 53BP2-IP3 nucleic acid. A kit can optionally further comprise in a container a predetermined amount of a purified 53BP2:53BP2-IP complex, 53BP2 and/or a 53BP2-IP or 53BP2-IP1, 53BP2-IP2, or 53BP2-IP3 or nucleic acids thereof, e.g., for use as a standard or control.

Therapeutic Uses of 53BP2:53BP2-IP Complexes and 53BP2-IP1, 53BP2-IP2, and 53BP2-IP3

The invention provides for treatment or prevention of various diseases and disorders-by administration of a therapeutic compound (termed herein "Therapeutic"). Such "Therapeutics" include but are not limited to: 53BP2:53BP2-IP complexes (e.g. 53BP2 complexed with β-tubulin, p62, hnRNP G, 53BP2-IP1, 53BP2-IP2, or 53BP2-IP3)., 53BP2 and the individual 53BP2-IPs (e.g., β-tubulin, p62, hnRNP G, 53BP2-IP1, 53BP2-IP2, and 53BP2-IP3) proteins and analogs and derivatives (including fragments) of the foregoing (e.g., as described hereinabove); antibodies thereto (as described hereinabove); nucleic acids encoding the 53BP2 and/or the 53BP2-IP and 53BP2-IP1, 53BP2-IP2, and 53BP2-IP3 and analogs or derivatives, thereof (e.g., as described hereinabove); 53BP2, 53BP2-IP, 53BP2-IP1, 53BP2-IP2, and 53BP2-IP3 antisense nucleic acids, and 53BP2:53BP2-IP complex and 53BP2-IP1, 53BP2-IP2, and 53BP2-IP3 modulators (i.e., inhibitors, agonists and antagonists).

53BP2 and several of its binding partners, as identified herein, (e.g. β-tubulin, p62, and hnRNP G) are implicated significantly in disorders of cell cycle progression, cell differentiation, and transcriptional control, including cancer and tumorigenesis and tumor progression. Disorders of neurodegeneration resulting from altered cellular apoptosis, mRNA destabilization, and ubiquitin-mediated proteolysis, can likewise involve these same proteins. HnRNP G is specifically implicated in autoimmune disorders. A wide range of cell diseases affected by intracellular signal transduction, including c-Src signalling, and translational regulation are treated or prevented by administration of a Therapeutic that modulates (i.e. inhibits, antagonizes or promotes) 53BP2:53BP2-IP complex activity, or 53BP2-IP1, 53BP2-IP2, or 53BP2-IP3 activity.

Diseases and disorders associated with aberrant levels of 53BP2:53BP2-IP complex levels or activity or aberrant levels of 53BP2 and/or a 53BP2-IP, 53BP2-IP1, 53BP2-IP2, or 53BP2-IP3 may be treated or prevented by administration of a Therapeutic that modulates 53BP2:53BP2-IP complex formation or activity or 53BP2-IP1, 53BP2-IP2, or 53BP2-IP3 activity. In a specific embodiment, the activity or levels of 53BP2 is modulated by administration of a 53BP2-IP. In another specific embodiment, the activity or levels of a 53BP2-IP is modulated by administration of 53BP2.

Diseases and disorders characterized by increased (relative to a subject not suffering from the disease or disorder) 53BP2:53BP2-IP levels or activity or increased 53BP2-IP1, 53BP2-IP2, or 53BP2-IP3 levels or activity can be treated with Therapeutics that antagonize (i.e., reduces or inhibits) 53BP2:53BP2-IP complex formation or activity or 53BP2-IP1, 53BP2-IP2, or 53BP2-IP3 levels or activity. Therapeutics that can be used include but are not limited to 53BP2 or a 53BP2-IP or analogs, derivatives or fragments thereof, anti-53BP2:53BP2-IP complex antibodies (e.g. antibodies specific for 53BP2:β-tubulin, 53BP2:p62, 53BP2:hnRNP G, 53BP2:53BP2-IP1, 53BP2:53BP2-IP2, or 53BP2-53BP2-IP3 complexes) and anti-53BP2-IP1, anti-53BP2-IP2, and anti-53BP2-IP3 antibodies (fragments and derivatives thereof containing the binding region thereof), nucleic acids encoding 53BP2 or 53BP2-IP, concurrent administration of 53BP2 and a 53BP2-IP antisense nucleic acid or a 53BP2-IP1, 53BP2-IP2, or 53BP2-IP3 anti-sense nucleic acid, and 53BP2 and/or 53BP2-IP, or 53BP2-IP1, 53BP2-IP2, or 53BP2-IP3 nucleic acids that are dysfunctional (e.g., due to a heterologous (non-53BP2 and/or non-53BP2-IP, or non-53BP2-IP1, non-53BP2-IP2, or non-53BP2-IP3) insertion within the 53BP2, 53BP2-IP, 53BP2-IP1, 53BP2-IP2, or 53BP2-IP3 coding sequences) that are used to "knockout" endogenous 53BP2 and/or 53BP2-IP, or 53BP2-IP1, 53BP2-IP2, or 53BP2-IP3 function by homologous recombination (see, e.g., Capecchi, 1989, Science 244: 1288–1292). In a specific embodiment of the invention, a nucleic acid containing a portion of a 53BP2 and/or a 53BP2-IP or 53BP2-IP1, 53BP2-IP2, or 53BP2-IP3 gene in which the 53BP2, 53BP2-IP, 53BP2-IP1, 53BP2-IP2, or 53BP2-IP3 sequences flank (are both 5' and 3' to) a different gene sequence, is used, as a 53BP2 and/or 53BP2-IP or 53BP2-IP1, 53BP2-IP2, or 53BP2-IP3 antagonist, to promote 53BP2 and/or 53BP2-IP or 53BP2-IP1, 53BP2-IP2, or 53BP2-IP3 inactivation by homologous recombination (see also Koller and Smithies, 1989, Proc. Natl. Acad. Sci. USA 86: 8932–8935; Zijlstra et al., 1989, Nature 342: 435–438). Additionally, mutants or derivatives of a first 53BP2-IP protein that have greater affinity for 53BP2 than the wild type first 53BP2-IP may be administered to compete with a second 53BP2-IP protein for 53BP2 binding, thereby reducing the levels of 53BP2 complexes with the second 53BP2-IP. Other Therapeutics that inhibit 53BP2:53BP2-IP complex or 53BP2-IP1, 53BP2-IP2, or 53BP2-IP3 function can be identified by use of known convenient in vitro assays, e.g., based on their ability to inhibit 53BP2-53BP2-IP binding or as described in Section 5.6 infra.

In specific embodiments, Therapeutics that antagonize 53BP2:53BP2-IP complex formation or activity or 53BP2-IP1, 53BP2-IP2, or 53BP2-IP3 activity are administered therapeutically (including prophylactically): (1) in diseases or disorders involving an increased (relative to normal or desired) level of 53BP2:53BP2-IP complex or 53BP2-IP1, 53BP2-IP2, or 53BP2-IP3 proteins, for example, in patients where 53BP2:53BP2-IP complexes or 53BP2-IP1, 53BP2-IP2, or 53BP2-IP3 is overactive or overexpressed; or (2) in diseases or disorders wherein in vitro (or in vivo) assays (see infra) indicate the utility-of 53BP2:53BP2-IP complex or 53BP2-IP1, 53BP2-IP2, or 53BP2-IP3 antagonist administration. Increased levels of 53BP2:53BP2-IP complexes or 53BP2-IP1, 53BP2-IP2, or 53BP2-IP3 protein can be readily detected, e.g., by quantifying protein and/or RNA (or cDNA generated from RNA), by obtaining a patient tissue sample (e.g., from biopsy tissue) and assaying it in vitro for RNA or protein levels, structure and/or activity of the expressed 53BP2:53BP2-IP complex (or the 53BP2 and 53BP2-IP mRNA) or 53BP2-IP1, 53BP2-IP2, or 53BP2-IP3 protein or mRNA. Many methods standard in the art can be thus employed, including but not limited to, immunoassays to detect 53BP2:53BP2-IP complexes or 53BP2-IP1, 53BP2-IP2, or 53BP2-IP3 and/or visualize 53BP2:53BP2-IP complexes or 53BP2-IP1, 53BP2-IP2, or 53BP2-IP3 protein (e.g., Western blot, immunoprecipitation followed by sodium dodecyl sulfate polyacrylamide gel electrophoresis, immunocytochemistry, etc.) and/or hybridization assays to detect concurrent expression of 53BP2 and a 53BP2-IP, or 53BP2-IP1, 53BP2-IP2, or 53BP2-IP3 mRNA (e.g., Northern assays, dot blots, in situ hybridization, etc.).

A more specific embodiment includes methods of reducing 53BP2:53BP2-IP complex expression (i.e., the expression of the two components of the 53BP2:53BP2-IP complex and/or formation of the complex) or 53BP2-IP1, 53BP2-IP2, or 53BP2-IP3 expression, by targeting mRNAs that express the protein moieties. RNA therapeutics currently fall within three classes, antisense species, ribozymes, or RNA aptamers (Good et al., 1997, Gene Therapy 4: 45–54). Antisense oligonucleotides have been the mode widely used. By way of example, but not for limitation, antisense oligonucleotide methodology to reduce 53BP2 complex formation is presented below in subsection 5.5.7 infra. Ribozyme therapy involves the administration, induced expression, etc. of small RNA molecules with enzymatic ability to cleave, bind, or otherwise inactivate specific RNAs to reduce or eliminate expression of particular proteins (Grassi and Marini, 1996, Annals of Medicine 28: 499–510; Gibson, 1996, Cancer and Metastasis Reviews 15: 287–299). At present, the design of "hairpin" and "hammerhead" RNA ribozymes is necessary to specifically target a particular mRNA such as that for 53BP2. RNA aptamers are specific RNA ligands for proteins, such as for Tat and Rev RNA (Good et al., 1997, Gene Therapy 4: 45–54) that can specifically inhibit their translation. Aptamers specific for 53BP2, a 53BP2-IP, 53BP2-IP1, 53BP2-IP2, or 53BP2-IP3 can be identified by many methods well known in the art, for example but not limited to the protein-protein interaction assay described in Section 5.7.1 infra.

In another embodiment, the activity or levels of 53BP2 is reduced by administration of a 53BP2-IP, or a nucleic acid that encodes the 53BP2-IP, or antibody that immunospecifically binds the 53BP2-IP, or a fragment or derivative of the antibody containing the binding domain thereof. Additionally, the levels or activity of a 53BP2-IP maybe reduced by administration of 53BP2 or a nucleic acid encoding 53BP2, or an antibody that immunospecifically binds 53BP2, or a fragment or derivative of the antibody containing the binding domain thereof.

In another aspect of the invention, diseases or disorders associated with increased levels of 53BP2 or a particular 53BP2-IP (e.g. β-tubulin, p62, hnRNP G, 53BP2-IP1, 53BP2-IP2 or 53BP2-IP3) may be treated or prevented by administration of a Therapeutic that increases 53BP2:53BP2-IP complex formation if the complex formation acts to reduce or inactivate 53BP2 or the particular 53BP2-IP through the 53BP2:53BP2-IP complex formation. Such diseases or disorders can be treated or prevented by administration of one member of the 53BP2:53BP2-IP complex, including mutants of a member of the 53BP2:53BP2-IP that has increased affinity for the other member of the 53BP2:53BP2-IP complex (to cause increased complex formation), administration of antibodies or other molecules that stabilize the 53BP2:53BP2-IP complex, etc.

Diseases and disorders associated with underexpression of a 53BP2:53BP2-IP or 53BP2-IP1, 53BP2-IP2, or 53BP2-IP3 or 53BP2 or a 53BP2-IP are treated or prevented by administration of a Therapeutic that promotes (i.e., increases or supplies) 53BP2:53BP2-IP complex or 53BP2-IP1, 53BP2-IP2, or 53BP2-IP3 function. Examples of such a Therapeutic include but are not limited to 53BP2:53BP2-IP complexes and 53BP2-IP1, 53BP2-IP2, and 53BP2-IP3 proteins and derivatives, analogs and fragments thereof that are functionally active (e.g., active to form 53BP2:53BP2-IP complexes), uncomplexed 53BP2 and 53BP2-IP proteins and derivatives, analogs fragments thereon and nucleic acids encoding the members of a 53BP2:53BP2-IP complex or encoding 53BP2-IP1, 53BP2-IP2, or 53BP2-IP3 or functionally active derivative or fragment thereof (e.g., for use in gene therapy). In a specific embodiment, derivatives, homologs or fragments of 53BP2 and/or a 53BP2-IP that increase and/or stabilize 53BP2:53BP2-IP complex formation. Examples of other agonists can be identified using in vitro assays or animal models, examples of which are described supra.

In specific embodiments, Therapeutics that promote 53BP2:53BP2-IP complex or 53BP2-IP1, 53BP2-IP2, or 53BP2-IP3 function are administered therapeutically (including prophylactically): (1) in diseases or disorders involving an absence or decreased (relative to normal or desired) level of 53BP2:53BP2-IP complex or 53BP2-IP1, 53BP2-IP2, or 53BP2-IP3 proteins, for example, in patients where 53BP2:53BP2-IP complexes (or the individual components necessary to form the complexes) or 53BP2-IP1, 53BP2-IP2, or 53BP2-IP3 is lacking, genetically defective, biologically inactive or underactive, or under-expressed; or (2) in diseases or disorders wherein in vitro (or in vivo) assays (see infra) indicate the utility of 53BP2:53BP2-IP complex or 53BP2-IP1, 53BP2-IP2, 53BP2-IP3 agonist administration. The absence or decreased level in 53BP2:53BP2-IP complex or 53BP2-IP1, 53BP2-IP2, or 53BP2-IP3 protein or function can be readily detected, e.g., by obtaining a patient tissue sample (e.g., from biopsy tissue) and assaying it in vitro for RNA (or cDNA generated from mRNA) or protein levels, structure and/or activity of the expressed 53BP2:53BP2-IP complex (or for the concurrent expression of mRNA encoding the two components of the 53BP2:53BP2-IP complex) or 53BP2-IP1, 53BP2-IP2, or 53BP2-IP3 RNA or protein. Many methods standard in the art can be thus employed, including but not limited to immunoassays to detect and/or visualize 53BP2:53BP2-IP complexes (or the individual components of 53BP2:53BP2-IP complexes) or 53BP2-IP1, 53BP2-IP2, or 53BP2-IP3 (e.g., Western blot, immunoprecipitation followed by sodium dodecyl sulfate polyacrylamide gel electrophoresis, immunocytochemistry, etc.) and/or hybridization assays to detect expression of the mRNA encoding the individual protein components of the 53BP2:53BP2-IP complexes or 53BP2-IP1, 53BP2-IP2, or 53BP2-IP3 by detecting and/or visualizing 53BP2 and a 53BP2-IP concurrently or 53BP2-IP1, 53BP2-IP2, or 53BP2-IP3 mRNA (e.g., Northern assays, dot blots, in situ hybridization, etc.), etc.

In specific embodiment, the activity or levels of 53BP2 are increased by administration of a 53BP2-IP, or derivative or analog thereof, a nucleic acid encoding a 53BP2-IP, or an antibody that immunospecifically binds a 53BP2-IP, or a fragment or derivative of the antibody contains the binding domain thereof. In another specific embodiment, the activity or levels of a 53BP2-IP are increased by administration of 53BP2, or derivative or analog thereof, a nucleic acid encoding 53BP2, or an antibody that immunospecifically binds 53BP2, or a fragment or derivative of the antibody contains the binding domain thereof.

Generally, administration of products of a species origin or species reactivity (in the case of antibodies) that is the same species as that of the patient is preferred. Thus, in a preferred embodiment, a human 53BP2:53BP2-IP complex or 53BP2-IP1, 53BP2-IP2, or 53BP2-IP3 protein, or derivative or analog thereof, nucleic acids encoding the members of the human 53BP2:53BP2-IP complex or human 53BP2-IP1, human 53BP2-IP2 or human 53BP2-IP3 or derivative or analog thereof, an antibody to a human 53BP2:53BP2-IP complex or 53BP2-IP1, 53BP2-IP2, or 53BP2-IP3 or derivative thereof, is therapeutically or prophylactically administered to a human patient.

Preferably, suitable in vitro or in vivo assays, are utilized to determine the effect of a specific Therapeutic and whether its administration is indicated for treatment of the affected tissue.

In various specific embodiments, in vitro assays can be carried out with representative cells of cell types involved in a patient's disorder, to determine if a Therapeutic has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Additional descriptions and sources of Therapeutics that can be used according to the invention are found in Sections 5.1–5.3 and 5.8 herein.

Malignancies

Components of the 53BP2:53BP-IP complexes (i.e., 53BP2, β-tubulin, p62 and hnRNP G) have been implicated in regulation of cell proliferation. Accordingly, Therapeutics of the invention may be useful in treating or preventing diseases or disorders associated with cell overproliferation or loss of control of cell proliferation, particularly cancers, malignancies and tumors. Therapeutics of the invention can be assayed by any method known in the art for efficacy in treating or preventing malignancies and related disorders, such assays include in vitro assays using transformed cells or cells derived from a tumor of a patient or in vivo assays using animal models of cancer or malignancies, or any of the assays described in Section 5.6 infra. Potentially effective Therapeutics, for example but not limited to, inhibit proliferation of tumor or transformed cells in culture or cause regression of tumors in animal models in comparison to controls, e.g., as described in Section 5.6, supra.

Accordingly, once a malignancy or cancer has been shown to be amenable to treatment by modulation (i.e., inhibit, antagonize or agonize) of 53BP2:53BP2-IP complex activity or 53BP2-IP1, 53BP2-IP2, or 53BP2-IP3 activity, that cancer or malignancy can be treated or prevented by administration of a Therapeutic that modulates 53BP:53BP2-IP complex formation (including supplying 53BP2:53BP2-IP complexes and the individual binding partners of a 53BP2:53BP2-IP complex, e.g., 53BP2, β-tubulin, p62, hnRNP G, 53BP2-IP1, 53BP2-IP2, and 53BP2-IP3), or 53BP2-IP1, 53BP2-IP2, or 53BP2-IP3 function. Such cancer and malignancies include but are not limited to those listed in Table 1 (for a review of such disorders, see Fishman et al., 1985, *Medicine*, 2d Ed., J. B. Lippincott Co., Philadelphia).

TABLE 1

MALIGNANCIES AND RELATED DISORDERS

Leukemia acute leukemia
    acute lymphocytic leukemia
    acute myelocytic leukemia
    myeloblastic
    promyelocytic
    myelomonocytic
    monocytic
    erythroleukemia
    chronic leukemia
    chronic myelocytic (granulocytic) leukemia
    chronic lymphocytic leukemia
    Polycythemia vera
Lymphoma
    Hodgkin's disease
    non-Hodgkin's disease
Multiple myeloma
Waldenström's macroglobulinemia
Heavy chain disease
Solid tumors
    sarcomas and carcinomas fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma TABLE 1-continued

MALIGNANCIES AND RELATED DISORDERS pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular tumor
lung carcinoma
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma In specific embodiments, malignancy or dysproliferative changes (such as metaplasias and dysplasias), or hyperproliferative disorders, are treated or prevented in the bladder, breast, colon, lung, melanoma, pancreas, or uterus. In other specific embodiments, sarcoma, or leukemia is treated or prevented.

Premalignant Conditions

The Therapeutics of the invention that are effective in treating cancer or malignancies (e.g. as described above) can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult cell or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention that modulates 53BP2:53BP2-IP complex activity or 53BP2-IP1, 53BP2-IP2, or 53BP2-IP3 activity. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W. B. Saunders Co., Philadelphia, pp. 112–113) etc.)

In another specific embodiment, a Therapeutic of the invention is administered to a human patient to prevent progression to breast, colon, lung, pancreatic, or uterine cancer, or melanoma or sarcoma.

Hyperproliferative and Dysproliferative Disorders

In another embodiment of the invention, a Therapeutic is administered to treat or prevent hyperproliferative or benign dysproliferative disorders. Therapeutics of the invention can be assayed by any method known in the art for efficacy in treating or preventing hyperproliferative diseases or disorders, such assays include in vitro cell proliferation assays, in vitro or in vivo assays using animal models of hyperproliferative diseases or disorders, or any of the assays described in Section 5.6 infra. Potentially effective Therapeutics, for example but not limited to, promote cell proliferation in culture or cause growth or cell proliferation in animal models in comparison to controls.

Accordingly, once a hyperproliferative disorder has been shown to be amenable to treatment by modulation of 53BP2:53BP2-IP complex activity or 53BP2-IP1, 53BP2-IP2, or 53BP2-IP3 activity, that hyperproliferative disease or disorder can be treated or prevented by administration of a Therapeutic that modulates 53BP:53BP2-IP complex formation (including supplying 53BP2:53BP2-IP complexes and the individual binding partners of a 53BP2:53BP2-IP complex, e.g., 53BP2, β-tubulin, p62, hnRNP G, 53BP2-IP1, 53BP2-IP2 and 53BP2-IP3) or 53BP2-IP1, 53BP2-IP2, or 53BP2-IP3 function. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

Neurodegenerative Disorders

53BP2 and certain binding partners of 53BP2 (e.g. β-tubulin and p62) have been implicated in the deregulation of cellular maturation and apoptosis, which are characteristic of neurodegenerative disease. Accordingly, Therapeutics of the invention, particularly those that modulate (or supply) 53BP2:β-tubulin or 53BP2:p62 complexes maybe effective in treating or preventing neurodegenerative disease. Therapeutics of the invention (particularly those that modulate the levels or activity of 53BP2:β-tubulin or 53BP2:p62 complexes) can be assayed by any method known in the art for efficacy in treating or preventing such neurodegenerative diseases and disorders, such assays include in vitro assays for regulated cell maturation or inhibition of apoptosis or in vivo assays using animal models of neurodegenerative diseases or disorders, or any of the assays described in Sections 5.6 infra. Potentially effective Therapeutics, for example but not by way of limitation, promote regulated cell maturation and prevent cell apoptosis in culture or reduce neurodegeneration in animal models in comparison to controls.

Once a neurodegenerative disease or disorder has been shown to be amenable to treatment by modulation of 53BP2:53BP2-IP complex activity or 53BP2-IP1, 53BP2-IP2, or 53BP2-IP3 activity, that neurodegenerative disease or disorder can be treated or prevented by administration of a Therapeutic that modulates 53BP:53BP2-IP complex formation (including supplying 53BP2:53BP2-IP complexes, e.g., 53BP2: β-tubulin and 53BP2:p62 complexes) or 53BP2-IP1, 53BP2-IP2, or 53BP2-IP3 function.

Such diseases include the neurodegenerative disorders involved with aging, especially osteoarthritis and neurodegenerative disorders. Neurodegenerative disorders that can be treated or prevented include but are not limited to those listed in Table 2 (see Isslebacher et al., 1997, in: *Harrison's Principals of Internal Medicine*, 13$^{th}$ Ed., McGraw Hill, New York).

TABLE 2

NEURODEGENERATIVE DISORDERS

Progressive dementia in the absence of other neurological signs

Alzheimer's Disease (or early-onset AD)
Senile dementia of the Alzheimer's type (or late onset AD)
Pick's Disease
Syndromes combining progressive dementia with prominent neurological abnormalities Huntington's disease
Multiple system atrophy (dementia combined with ataxia, Parkinson's disease, etc.)
Progressive supranuclear palsy
Diffuse Lewy body disease
Corticodentatonigral degeneration
Hallervorden-Spatz disease
Progressive familial myoclonic epilepsy
Syndromes of gradually developing abnormalities of posture and movement Parkinson's disease
Striatonigral degeneration
Progressive supranuclear palsy
Torsion dystonia
Spasmodic torticollis and other restricted dyskinesias
Familial tremor
Gilles de la Tourette syndrome
Syndromes of progressive ataxia Cerebellar cortical degeneration
Olivopontocerebellar atrophy
Friedrich's ataxia and related spinocerebellar degenerations
Shy-Drager syndrome
Subacute necrotizing encephalopathy
Motor neuron disease without sensory changes Amyotrophic lateral sclerosis
Infantile spinal muscular atrophy
Juvenile spinal muscular atrophy
Other forms of familial spinal muscular atrophy
Primary lateral sclerosis
Hereditary spastic paraplegia
Motor neuron disease with sensory changes Peroneal muscular atrophy
Hypertrophic interstitial polyneuropathy
Other forms of chronic progressive neuropathy
Syndromes of progressive visual loss
Retinitis pigmentosa Autoimmune Disorders The 53BP2 binding partner hnRNP G has been implicated in autoimmune disorders. Therapeutics of the invention, particularly those that modulate (or supply) 53BP2:hnRNPG complex activity may be effective in treating or preventing autoimmune diseases or disorders. Therapeutics of the invention (particularly Therapeutics that modulate the levels or activity of 53BP2:hnRNP G) can be assayed by any method known in the art for efficacy in treating or preventing such autoimmune diseases and disorders, such assays include in vitro assays for using cell culture models as described in Section 5.6, infra, or in vivo assays using animal models of autoimmune diseases or disorders as described in Section 5.6 infra. Potentially effective Therapeutics, for example but not by way of limitation, reduce autoimmune responses in animal models in comparison to controls.

Accordingly, once an autoimmune disease or disorder has been shown to be amenable to treatment by modulation of 53BP2:53BP2-IP complex activity or 53BP2-IP1, 53BP2-IP2, or 53BP2-IP3 activity, that autoimmune disease or disorder can be treated or prevented by administration of a Therapeutic that modulates 53BP:53BP2-IP complex formation (including supplying 53BP2:53BP2-IP complexes) or 53BP2-IP1, 53BP2-IP2, or 53BP2-IP3 function.

Autoimmune disorders that can be treated or prevented include but are not limited to those listed in Table 3 (Isslebacher et al., 1997, in *Harrison's Principals of Internal Medicine*, 13$^{th}$ Ed., McGraw Hill, New York).

TABLE 3

AUTOIMMUNE DISEASES

Organ Specific
Endocrine thyroid
Hashimoto's thyroiditis
Grave's disease
thyroiditis with hyperthyroidism
type I autoimmune polyglandular syndrome
type II autoimmune polyglandular syndrome
insulin-dependent diabetes mellitus
immune-mediated infertility
autoimmune Addison's disease
Skin pemphigus vulgaris
pemphigus foliaceus
bullus pemphigoid
dermatitis herpetiformis
linear IgA dermatosis
epidermolysis bullous aquisita
autoimmune allopecia
erythema nodosa
contact dermatitis
herpes gestationis
cicatricial pemphigoid
chronic bullous disease of childhood
Hemotologic autoimmune hemolytic anemia
lymphomas
chronic lymphocytic anemia
non-Hodgkin's lymphoma
Hodgkin's disease
drug-induced
alpha methyl dopa
penicillin type
quinidine type
post-viral infections
tumors (rare)
cold agglutinin diseases
acute
mycoplasma infection
infectious mononucleosis
chronic
idiopathic lymphoma
paroxysmal cold hemoglobinuria
autoimmune thrombocytopenic purpura
idiopathic
drug-induced
autoimmune neutropenia
Neuromuscular myasthenia gravis
acute disseminated encephalomyelitis
multiple sclerosis
Guillain-Barre syndrome
Chronic inflammatory demyelinating
polyradiculoneuropathy
Hepatobiliary autoimmune chronic active hepatitis
primary biliary sclerosis
sclerosing cholangitis
Gastrointestinal TABLE 3-continued

AUTOIMMUNE DISEASES gluten-sensitive enteropathy
perniciuos anemia
inflammatory bowel disease
Non-Organ Specific
Connective tissue disease system lupus erythematososis
rheumatoid arthritis
scleroderma
mixed connective tissue disease
psoriasis
polymyositis
dermatomyositis
Sjogren's syndrome
ankylosing spondylitis
reactive arthritis
undifferentiated spondylarthropathy
Behcet's syndrome
Vasculitis syndromes systemic necrotizing vasculitides
classic polyarteritis nodosa
Churg-Strauss disease
Polyangiitis overlap syndrome
hypersensitivity vasculitis
Wegener's granulomatosis
temporal arteritis
Takayasu's arteritis
Kawasaki's disease
isolated vasculitis of the central nervous system
thromboangiitis obliterans
Sarcoidosis
Graft-vs-host disease Gene Therapy In a specific embodiment, nucleic acids comprising a sequence encoding a 53BP2 and a 53BP2-IP, or 53BP2-IP1, 53BP2-IP2, or 53BP2-IP3, or functional derivatives thereof, are administered to modulate 53BP2:53BP2-IP complex or 53BP2-IP1, 53BP2-IP2, or 53BP2-IP3 function, by way of gene therapy. In more specific embodiments, a nucleic acid or nucleic acids encoding both 53BP2 and a 53BP2-IP (e.g., β-tubulin, p62, hnRNP G, 53BP2-IP1, 53BP2-IP2, or 53BP2-IP3) or functional derivatives thereof, are administered by way of gene therapy. Gene therapy refers to therapy performed by the administration of a nucleic acid to a subject. In this embodiment of the invention, the nucleic acid produces its encoded protein(s) that mediates a therapeutic effect by modulating 53BP2:53BP2-IP complex or 53BP2-IP1, 53BP2-IP2, or 53BP2-IP3 function.

Any of the methods for gene therapy available in the art can be used according to the present invention. Exemplary methods are described below.

For general reviews of the methods of gene therapy, see Goldspiel et al., 1993, Clinical Pharmacy 12: 488–505; Wu and Wu, 1991, Biotherapy 3: 87–95; Tolstoshev, 1993, Ann. Rev. Pharmacol. Toxicol. 32: 573–596; Mulligan, 1993, Science 260: 926–932; and Morgan and Anderson, 1993, Ann. Rev. Biochem. 62: 191–217; May, 1993, TIBTECH 11(5): 155–215). Methods commonly known in the art of recombinant DNA technology which can be used are described in Ausubel et al. (eds.), 1993, *Current Protocols in Molecular Biology*, John Wiley & Sons, NY; and Kriegler, 1990, *Gene Transfer and Expression, A Laboratory Manual*, Stockton Press, NY.

In a preferred aspect, the Therapeutic comprises a 53BP2 and a 53BP2-IP nucleic acid or 53BP2-IP1, 53BP2-IP2, or 53BP2-IP3 nucleic acid that is part of an expression vector that expresses the proteins 53BP2 and a 53BP2-IP or expresses 53BP2-IP1, 53BP2-IP2, or 53BP2-IP3 or fragments or chimeric proteins thereof in a suitable host. In particular, such a nucleic acid has a promoter operably linked to the 53BP2 and the 53BP2-IP coding region(s) (or, less preferably two separate promoters linked to the 53BP2 and the 53BP2-IP coding regions separately) or linked to the 53BP2-IP1, 53BP2-IP2, or 53BP2-IP3 coding region, said promoter being inducible or constitutive, and, optionally, tissue-specific. In another particular embodiment, a nucleic acid molecule is used in which the 53BP2 and 53BP2-IP coding sequences or 53BP2-IP1, 53BP2-IP2, or 53BP2-IP3 coding sequences, and any other desired sequences, are flanked by regions that promote homologous recombination at a desired site in the genome, thus providing for intrachromosomal expression of the 53BP2 and the 53BP2-IP nucleic acids or 53BP2-IP1, 53BP2-IP2, or 53BP2-IP3 nucleic acids (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the 53BP2 and/or the 53BP2-IP nucleic acids or 53BP2-IP1, 53BP2-IP2, or 53BP2-IP3 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The 53BP2 and/or 53BP2-IP (preferably both 53BP2 and 53BP2-IP) nucleic acids or 53BP2-IP1, 53BP2-IP2, or 53BP2-IP3 nucleic acids, to be used in gene therapy is/are cloned into the vector, which facilitates delivery of the gene into a patient. More detail about retroviral vectors can be found in Boesen et al., 1994, Biotherapy 6: 291–302, which describes the use of a retroviral vector to deliver the mdr1 gene to hematopoetic stem cells in order to make the stem cells more resistant to chemotherapy. Other references illustrating the use of retroviral vectors in gene therapy are: Clowes et al., 1994, J. Clin. Invest. 93: 644–651; Kiem et al., 1994, Blood 83: 1467–1473; Salmons and Gunzberg, 1993, Human Gene Therapy 4: 129–141; and Grossman and Wilson, 1993, Curr. Opin. in Genetics and Devel. 3: 110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3: 499–503 present a review of adenovirus-based gene therapy. Bout et al., 1994, Human Gene Therapy 5: 3–10 demonstrated the use of adenovirus vectors to transfer genes to the respiratory epithelia of rhesus monkeys. Other instances of the use of adenoviruses in gene therapy can be found in Rosenfeld et al., 1991, Science 252: 431–434; Rosenfeld et al., 1992, Cell 68: 143–155; and Mastrangeli et al., 1993, J. Clin. Invest. 91: 225–234.

Adeno-associated virus (AAV) has also been proposed for use in gene therapy (Walsh et al., 1993, Proc. Soc. Exp. Biol. Med. 204: 289–300.

Another approach to gene therapy involves transferring a gene into cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217: 599–618; Cohen et al., 1993, Meth. Enzymol. 217: 618–644; Cline, 1985, Pharmac. Ther. 29: 69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoetic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoetic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a 53BP2 and/or a 53BP2-IP (preferably both a 53BP2 and a 53BP2-IP) nucleic acid or 53BP2-IP1, 53BP2-IP2, or 53BP2-IP3 nucleic acid is/are introduced into the cells such that the gene.or genes are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoetic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71: 973–985).

Epithelial stem cells (ESCs) or keratinocytes can be obtained from tissues such as the skin and the lining of the gut by known procedures (Rheinwald, 1980, Meth. Cell Bio. 21A: 229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A: 229; Pittelkow and Scott, 1986, Mayo Clinic Proc. 61: 771). If the ESCs are provided by a donor, a method for suppression of host versus graft reactivity (e.g., irradiation, drug or antibody administration to promote moderate immunosuppression) can also be used.

With respect to hematopoetic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allergenic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73: 1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91: 335) or Witlock-Witte culture techniques (Witlock and Witte, 1982, Proc. Natl. Acad. Sci. USA 79: 3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods can be adapted for use to deliver a nucleic acid encoding the 53BP2 and/or 53BP2-IP proteins or 53BP2-IP1, 53BP2-IP2, or 53BP2-IP3 proteins, or functional derivatives thereof, e.g., as described in Sections 5.1 and 5.2 supra.

Use of Antisense Oligonucleotides for Suppression of 53BP2:53BP2-IP Complexes and 53BP2-IP1, 53BP2-IP2, and 53BP2-IP3

In a specific embodiment, 53BP2:53BP2-IP complex function or 53BP2-IP1, 53BP2-IP2, or 53BP2-IP3 protein function is inhibited by use of antisense nucleic acids for 53BP2 and/or a 53BP2-IP (e.g., β-tubulin, p62, hnRNP G, 53BP2-IP1, 53BP2-IP2, and 53BP2-IP3) (preferably both 53BP2 and the 53BP2-IP) or antisense nucleic acids for 53BP2-IP1, 53BP2-IP2, or 53BP2-IP3. The present invention provides the therapeutic or prophylactic use of nucleic acids of at least six nucleotides that are antisense to a gene or cDNA encoding 53BP2 and/or a 53BP2-IP or encoding 53BP2-IP1, 53BP2-IP2, or 53BP2-IP3, or portions thereof. A 53BP2, 53BP2-IP, 53BP2-IP1, 53BP2-IP2, or 53BP2-IP3 "antisense" nucleic acid as used herein refers to a nucleic acid capable of hybridizing to a portion of a 53BP2, 53BP2-IP, 53BP2-IP1, 53BP2-IP2, or 53BP2-IP3 RNA (preferably mRNA) by virtue of some sequence complementarity. The antisense nucleic acid may be complementary to a coding and/or noncoding region of a 53BP2, 53BP2-IP, 53BP2-IP1, 53BP2-IP2, or 53BP2-IP3 mRNA. Such antisense nucleic acids have utility as Therapeutics that inhibit 53BP2:53BP2-IP complex formation or activity or 53BP2-IP1, 53BP2-IP2, or 53BP2-IP3 function or activity, and can be used in the treatment or prevention of disorders as described supra.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In another embodiment, the invention is directed to methods for inhibiting the expression of 53BP2 and a 53BP2-IP nucleic acid sequence or 53BP2-IP1, 53BP2-IP2, or 53BP2-IP3 nucleic acid sequence in a prokaryotic or eukaryotic cell comprising providing the cell with an effective amount of a composition comprising an antisense nucleic acid of 53BP2 and 53BP2-IP, or an antisense nucleic acid of 53BP2-IP1, 53BP2-IP2, or 53BP2-IP3, or derivatives thereof, of the invention.

The 53BP2, 53BP2-IP, 53BP2-IP1, 53BP2-IP2, and 53BP2-IP3 antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, a 53BP2, 53BP2-IP, 53BP2-IP1, 53BP2-IP2, or 53BP2-IP3 antisense oligonucleotide is provided, preferably as single-stranded DNA. The oligonucleotide may be modified at any position on its structure with constituents generally known in the art.

The 53BP2, 53BP2-IP, 53BP2-IP1, 53BP2-IP2, or 53BP2-IP3 antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc.

In a specific embodiment, the 53BP2, 53BP2-IP, 53BP2-IP1, 53BP2-IP2, or 53BP2-IP3 antisense oligonucleotides comprise catalytic RNAs, or ribozymes (see, e.g., PCT International Publication WO 90/11364, published Oct. 4, 1990; Sarver et al., 1990, Science 247: 1222–1225). In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

In an alternative embodiment, the 53BP2, 53BP2-IP, 53BP2-IP1, 53BP2-IP2, or 53BP2-IP3 antisense nucleic acids of the invention are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding 53BP2, 53BP2-IP (preferably, a 53BP2 and a 53BP2-IP anti-sense nucleic acid), 53BP2-IP1, 53BP2-IP2, or 53BP2-IP3 antisense nucleic acids. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the 53BP2, 53BP2-IP, 53BP2-IP1, 53BP2-IP2, or 53BP2-IP3 antisense RNAs can be by any promoter known in the art to act in mammalian, preferably human, cells. Such promoters can be inducible or constitutive. Such promoters include but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

The antisense nucleic acids of the invention comprise a sequence complementary to at least a portion of an RNA transcript of a 53BP2, 53BP2-IP, 53BP2-IP1, 53BP2-IP2, or 53BP2-IP3 gene, preferably a human 53BP2, 53BP2-IP, 53BP2-IP1, 53BP2-IP2, or 53BP2-IP3 gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded 53BP2, 53BP2-IP, 53BP2-IP1, 53BP2-IP2, or 53BP2-IP3 antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a 53BP2, 53BP2-IP, 53BP2-IP1, 53BP2-IP2, or 53BP2-IP3 RNA it may contain and still form a stable duplex (or triplex, as the case may be). One skilled in the art can ascertain a tolerable degree of mismatch by use of standard procedures to determine the melting point of the hybridized complex.

The 53BP2 and 53BP2-IP antisense nucleic acid or 53BP2-IP1, 53BP2-IP2, or 53BP2-IP3 antisense nucleic acids can be used to treat (or prevent) disorders of a cell type that expresses, or preferably overexpresses, the 53BP2:53BP2-IP complex or 53BP2-IP1, 53BP2-IP2, or 53BP2-IP3 protein. In a preferred embodiment, a single-stranded DNA antisense 53BP2 and 53BP2-IP antisense oligonucleotide or single-stranded DNA antisense 53BP2-IP1, 53BP2-IP2, or 53BP2-IP3 oligonucleotide is used.

Cell types that express or overexpress 53BP2 and 53BP2-IP RNA or 53BP2-IP1, 53BP2-IP2, or 53BP2-IP3 RNA can be identified by various methods known in the art. Such methods include, but are not limited to, hybridization with 53BP2- and 53BP2-IP-specific nucleic acids or 53BP2-IP1-, 53B2-IP2- or 53BP2-IP3-specific nucleic acids (e.g. by northern hybridization, dot blot hybridization, in situ hybridization), or by observing the ability of RNA from the cell type to be translated in vitro into 53BP2 and the 53BP2-IP or into 53BP2-IP1, 53BP2-IP2, or 53BP2-IP3 by immunohistochemistry. In a preferred aspect, primary tissue from a patient can be assayed for 53BP2 and 53BP2-IP expression or for 53BP2-IP1, 53BP2-IP2, or 53BP2-IP3 expression prior to treatment, e.g., by immunocytochemistry or in situ hybridization.

Pharmaceutical compositions of the invention (see Section 5.8 infra), comprising an effective amount of a 53BP2 and a 53BP2-IP antisense nucleic acid or a 53BP2-IP1, 53BP2-IP2, or 53BP2-IP3 antisense nucleic acid in a pharmaceutically acceptable carrier, can be administered to a patient having a disease or disorder which is of a type that expresses or overexpresses 53BP2:53BP2-IP complexes or 53BP2-IP1, 53B2-IP2, or 53BP2-IP3 RNA or protein.

The amount of 53BP2 and 53BP2-IP antisense nucleic acids or 53BP2-IP1, 53BP2-IP2, or 53BP2-IP3 antisense nucleic acid that will be effective in the treatment of a particular disorder or condition will depend on the nature of the disorder or condition, and can be determined by standard clinical techniques. Where possible, it is desirable to determine the antisense cytotoxicity in vitro, and then in useful animal model systems prior to testing and use in humans.

In a specific embodiment, pharmaceutical compositions comprising 53BP2 and 53BP2-IP antisense nucleic acids or 53BP2-IP1, 53BP2-IP2, or 53BP2-IP3 antisense nucleic acids are administered via liposomes, microparticles, or microcapsules. In various embodiments of the invention, it may be useful to use such compositions to achieve sustained release of the 53BP2 and 53BP2-IP antisense nucleic acids or 53BP2-IP1, 53BP2-IP2, or 53BP2-IP3 antisense nucleic acids. In a specific embodiment, it may be desirable to utilize liposomes targeted via antibodies to specific identifiable central nervous system cell types (Leonetti et al., 1990, Proc. Natl. Acad. Sci. U.S.A. 87: 2448–2451; Renneisen et al., 1990, J. Biol. Chem. 265: 16337–16342).

Assays of 53BP2:53BP2-IP Complexes, 53BP2-IP1, 53BP2-IP2, and 53BP2-IP3 and Derivatives and Analogs The functional activity of 53BP2:53BP2-IP complexes and 53BP2-IP1, 53BP2-IP2 and 53BP2-IP3 proteins, and derivatives, fragments and analogs thereof can be assayed by various methods. Potential modulators (e.g., inhibitors, agonists and antagonists) of 53BP2:53BP2 complex activity or 53BP2-IP1, 53BP2-IP2, or 53BP2-IP3 activity, e.g., anti-53BP2:53BP2-IP, anti-53BP2-IP1, anti-53BP2-IP2, and anti-53BP2-IP3 antibodies and 53BP2, 53BP2-IP, 53BP2-IP1, 53BP2-IP2, and 53BP2-IP3 antisense nucleic acids can be assayed for the ability to modulate 53BP2:53BP2-IP complex formation and/or activity or 53BP2-IP1, 53BP2-IP2, or 53BP2-IP3 activity.

For example, in one embodiment, where one is assaying for the ability to bind or compete with wild-type 53BP2:53BP2-IP complexes or 53BP2-IP1, 53BP2-IP2, or 53BP2-IP3 for binding to an anti-53BP2:53BP2-IP antibody or anti-53BP2-IP1, anti-53BP2-IP2, or anti-53BP2-IP3 antibodies, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

The expression of the 53BP2, 53BP2-IP, 53BP2-IP1, 53BP2-IP2, and 53BP2-IP3 genes (both endogenous genes and those expressed from cloned DNA containing these genes) can be detected using techniques known in the art, including but not limited to Southern hybridization (Southern, 1975, J. Mol. Biol. 98: 503–517), northern hybridization (e.g. Freeman et al., 1983, Proc. Natl. Acad. Sci. USA 80: 4094–4098), restriction endonuclease mapping (Sambrook et al., 1982, *Molecular Cloning, A Laboratory Manual*, Cold Spring Harbor Press, New York), and DNA sequence analysis. Polymerase chain reaction amplification (PCR; U.S. Pat. Nos. 4,683,202, 4,683,195, and 4,889,818; Gyllenstein et al., 1988, Proc. Natl. Acad. Sci. USA 85: 7652–7657; Ochman et al., 1988, Genetics 120: 621–623; Loh et al., 1989, Science 243: 217–220) followed by Southern hybridization or RNase protection (*Current Protocols in Molecular Biology*, John Wiley and Sons, New York, 1997) with probes specific for 53BP2, the 53BP2-IP, or 53BP2-IP1, 53BP2-IP2, or 53BP2-IP3 genes in various cell types. Methods of amplification other than PCR commonly known in the art can be employed. In one embodiment, Southern hybridization can be used to detect genetic linkage of 53BP2, 53BP2-IP, 53BP2-IP1, 53BP2-IP2, or 53BP2-IP3 gene mutations to physiological or pathological states. Various cell types, at various stages of development, can be characterized for their expression of 53BP2 and a 53BP2-IP (particularly expression of 53BP2 and 53BP2-IP at the same time and in the same cells), or 53BP2-IP1, 53BP2-IP2, or 53BP2-IP3 expression. The stringency of the hybridization conditions for northern or Southern blot analysis can be manipulated to ensure detection of nucleic acids with the desired degree of relatedness to the specific probes used. Modifications to these methods and other methods commonly known in the art can be used.

Derivatives (e.g., fragments) and analogs of 53BP2-IPs, including 53BP2-IP1, 53BP2-IP2, and 53BP2-IP3 (and fragments and other derivatives and analogs of 53BP2-IPs) can be assayed for binding to 53BP2 by any method-known in the art, for example the modified yeast two hybrid assay system described in Section 5.7.1 infra, immunoprecipitation with an antibody that binds to 53BP2 in a complex followed by analysis by size fractionation of the immunoprecipitated proteins (e.g. by denaturing or nondenaturing polyacrylamide gel electrophoresis), Western analysis, non-denaturing gel electrophoresis, etc.

One embodiment of the invention provides a method for screening a derivative or analog of 53BP2 for biological activity comprising contacting said derivative or analog of 53BP2 with a protein selected from the group consisting of β-tubulin, p62, hnRNP G, 53BP2-IP1, 53BP2-IP2, and 53BP2-IP3; and detecting the formation of a complex between said derivative or analog or 53BP2 and said protein; wherein detecting formation of said complex indicates that said derivative or analog of 53BP2 has biological (e.g., binding) activity. Additionally, another embodiment of the invention relates to a method for screening a derivative or analog of a protein selected from the group consisting of β-tubulin, p62, hnRNP G, 53BP2-IP1, 53BP2-IP2, and 53BP2-IP3 for biological activity comprising contacting said derivative or analog of said protein with 53BP2; and detecting the formation of a complex between said derivative or analog of said protein and 53BP2; wherein detecting the formation of said complex indicates that said derivative or analog of said protein has biological activity.

The invention also provides methods of modulating the activity of a protein that can participate in a 53BP2:53BP2-IP complex (e.g. 53BP2, β-tubulin, p62, hnRNP G. 53BP2-IP1, 53BP2-IP2, or 53BP2-IP3) by administration of a binding partner of that protein or derivative or analog thereof. 53BP2, and derivatives and analogs thereof, can be assayed for the ability to modulate the activity or levels of a 53BP2-IP by contacting a cell or administering an animal expressing a 53BP2-IP gene with a 53BP2 protein, or a nucleic acid encoding a 53BP2 protein or an antibody that immunospecifically binds the 53BP2 protein or a fragment or derivative of said antibody containing the binding domain thereof and measuring a change in 53BP2-IP levels or activity, wherein a change in 53BP2-IP levels or activity indicates that 53BP2 can modulate 53BP2-IP levels or activity. Alternatively, a 53BP2-IP can be assayed for the ability to modulate the activity or levels of a 53BP2 protein by contacting a cell or administering an animal expressing a gene encoding said protein with 53BP2, or a nucleic acid encoding 53BP2, or an antibody that immunospecifically binds 53BP2, or a fragment or derivative of said antibody containing the binding domain thereof, wherein a change in 53BP2 levels or activity indicates that the 53BP2-IP can modulate 53BP2 levels or activity.

53BP2, and several of the identified binding partners of 53BP2, e.g. β-tubulin, p62 protein and hnRNP G have roles in the control of cell proliferation and, therefore, cell-transformation and tumorigenesis. Accordingly, methods of the invention are provided for screening 53BP2:53BP2-IP complexes and 53BP2-IP1, 53BP2-IP2, and 53BP2-IP3 proteins, and fragments, derivatives and analogs of the foregoing, for activity in altering cell proliferation, cell transformation and/or tumorigenesis in vitro and in vivo.

The 53BP2:53BP2-IP complexes, 53BP2-IP1, 53BP2-IP2, and 53BP2-IP3 proteins, and derivatives, fragments, and analogs thereof, can be assayed for activity to alter (i.e., increase or decrease) cell proliferation in cultured cells in vitro using methods which are well-known in the art for measuring cell proliferation. Specific examples of cell culture models include, but are not limited to: for lung cancer primary rat lung tumor cells (Swafford et al., 1997, Mol. Cell. Biol., 17:1366–1374) and large-cell undifferentiated cancer cell lines (Mabry et al., 1991, Cancer Cells, 3:53–58); colorectal cell lines for colon cancer (Park and Gazdar, 1996, J. Cell Biochem. Suppl. 24:131–141); multiple established cell lines for breast cancer (Hambly et al., 1997, Breast Cancer Res. Treat. 43:247–258; Gierthy et al., 1997, Chemosphere 34:1495–1505; Prasad and Chiurch, 1997, Biochem. Biophys. Res. Commun. 232:14–19); a number of well-characterized cell models for prostate cancer (Webber et al., 1996, Prostate, Part 1, 29:386–394; Parts 2 and 3, 30:58–64 and 136–142; Boulikas, 1997, Anticancer Res. 17:1471–1505); continuous human bladder cancer cell lines for genitourinary cancers (Ribeiro et al., 1997, Int. J. Radiat. Biol. 72:11–20), organ cultures of transitional cell carcinomas (Booth et al., 1997, Lab Invest. 76:843–857), and rat progression models (Vet et al., 1997, Biochim. Biophys Acta 1360:39–44); established cell lines for leukemias and lymphomas (Drexler, 1994, Leuk. Res. 18:919–927; Tohyama, 1997, Int. J. Hematol. 65:309–317).

For example, but not by way of limitation, cell proliferation can be assayed by measuring $^3$H-thymidine incorporation, by direct cell count, by detecting changes in transcriptional activity of known genes such as proto-oncogenes (e.g., fos, myc) or cell cycle markers, etc. Accordingly, one embodiment of the invention provides a method of screening 53BP2:53BP2-IP complexes, 53BP2-IP1, 53BP2-IP2, and 53BP2-IP3 proteins, and fragments, derivatives, and analogs thereof, for activity in altering (i.e., increasing or decreasing) proliferation of cells in vitro comprising contacting the cells with a 53BP2:53BP2-IP complex or 53BP2-IP1, 53BP2-IP2, or 53BP2-IP3 protein, or derivative, analog, or fragment thereof, measuring the proliferation of cells that have been so contacted, and comparing the proliferation of the cells so contacted with a complex or protein of the invention with the proliferation of cells not so contacted with the complex or protein of the invention, wherein in a change in the level of proliferation in said contacted cells indicates that the complex or protein of the invention has activity to alter cell proliferation.

The 53BP2:53BP2-IP complexes and 53BP2-IP1, 53BP2-IP2, and 53BP2-IP3 proteins, and derivatives, fragments and analogs, thereof, can also be screened for activity in inducing or inhibiting cell transformation (or progression to malignant phenotype) in vitro. The complexes and proteins of the invention can be screened by contacting either cells with a normal phenotype (for assaying for cell transformation) or a transformed cell phenotype (for assaying for inhibition of cell transformation) with the complex or protein of the invention and examining the cells for acquisition or loss of characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York, pp. 436–446).

The 53BP2:53BP2-IP complexes and 53BP2-IP1, 53BP2-IP2, and 53BP2-IP3 proteins, and derivatives, fragments, and analogs thereof can also be screened for activity to promote or inhibit tumor formation in vivo in non-human test animal. A vast number of animal models of hyperproliferative disorders, including tumorigenesis and metastatic spread, are known in the art (see Table 317–1, Chapter 317, "Principals of Neoplasia," in Harrison's Principals of Internal Medicine, 13th Edition, Isselbacher et al., eds., McGraw-Hill, New York, p.1814; Lovejoy et al., 1997, J. Pathol. 181:130–135). Specific examples include: transplantation of tumor modules into rats for lung cancer (Wang et al., 1997, Ann. Thorac. Surg. 64:216–219) or establishment of lung cancer metastases in SCID mice depleted of NK cells (Yono and Sone, 1997, Gan To Kagaku Ryoho, 24:489–494); colon cancer transplantation of human colon cancer cells into nude mice (Gutman and Fidler, 1995, World J. Surg., 19:226–234), the cotton top tamarin model of human ulcerative colitis (Warren, 1996, Aliment. Pharmacol. Ther., 10 Suppl2:45–47) and mouse models with mutations of the adenomatous polyposis coli tumor suppressor (Polakis, 1997, Biochim. Biophys. Acta 1332:F127–F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–4–0); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); for hematopoietic cancers, transplanted allogeneic marrow in animals (Appelbaum, 1997, Leukemia 11 Suppl 4:S15–S17). Further, general animal models applicable to many types of cancer have been described, including but not restricted to the p53-deficient mouse model (Donehower, 1996, Semin. Cancer Biol. 7:269–278), the Min mouse (Shoemaker et al., 1997, Biochem. Biophys. Acta, 1332:F25–F48), and immune response to tumors in the rat (Frey, 1997, Methods, 12:173–188).

For example, the complexes and proteins of the invention can be administered to a non-human test animal (preferably a test animal predisposed to develop a type of tumor) and the non-human test animals subsequently examined for an increased incidence of tumor formation in comparison with controls not administered the complex or protein of the invention. Alternatively, the complexes and proteins of the invention can be administered to non-human test animals having tumors (e.g., animals in which tumors have been induced by introduction of malignant, neoplastic, or transformed cells or by administration of a carcinogen) and subsequently examining the tumors in the test animals for tumor regression in comparison to controls.

The 53BP2:53BP2-IP complexes and 53BP2-IP1, 53BP2-IP2, and 53BP2-IP3 proteins, and derivatives, analogs, and fragments thereof, can also be screened for activity in modulating the activity of 53BP2 and the 53BP2 binding partners (i.e., the 53BP2-IPs, particularly β-tubulin, p62, hnRNP G, 53BP2-IP1, 53BP2-IP2, and 53BP2-IP3) involved in particular 53BP2:53BP2-IP complexes. For example, 53BP2 has been shown to bind a specific domain of the p53 protein and, by virtue of 53BP2-binding, enhance the tumor suppressor activity of p53. Accordingly, the complexes and proteins of the invention can be screened for the ability to modulate (i.e. increase or decrease) 53BP2 binding to p53 or the 53BP2-binding domain of p53, e.g., as described by Naumovski and Cleary (1996, Mol. Cell. Biol. 16:3884–3892); or for the ability to modulate the tumor suppressive activity of p53, e.g. by any protein binding assay known in the art, as described by Iwabuchi et al. (1994, Proc. Natl. Acad. Sci. USA 91: 6098–6102). 53BP2 has also been demonstrated to affect the phosphorylation and dephosphorylation of p53 by 53BP2's binding to protein phosphatase 1 (PP1). Thus, the complexes and proteins of the invention can be screened by assaying for changes in the level of p53 phosphorylation (e.g., as described in Milne et al., 1994, J. Biol. Chem. 269:9253–9260) or the level of 53BP2 binding to PP1 (e.g., by methods described supra).

β-tubulin has been shown to be upregulated in adenocarcinoma cells and, possibly, to bind proteins with Src homology 2 (SH2 domains), such as the PDGF receptor (Shaffhausen, 1995, Biochem. Biophys. Acta 1242:61–75). Thus, the complexes and proteins of the invention can be screened by assaying for changes in β-tubulin levels (e.g., by immunoassays with anti-β-tubulin antibodies) or for changes in β-tubulin binding to proteins with SH2 domains.

The protein p62 associates with the $p21^{waf}$ GTPase-activating protein (GAP), Src family tyrosine kinase SH3 domains in signalling proteins, binds RNA, interacts with ubiquitin, and also interacts with the cytosolic protein tyrosine kinase that negatively regulates the Src family protein kinases. Further, p62 may also play a role in docking certain proteins to the cytoskeleton or membrane upon c-Src activation. Thus, the complexes and proteins of the invention can also be screened by measuring changes in p62 binding to GAP, e.g., as described in Wang et al. (1992, Cell 69:551–558), p62 binding to proteins with SH3 domains, p62 binding to RNA, e.g. as described in Wang et al. (1995, J. Biol. Chem. 270:2010–2013), interaction with ubiquitin, e.g. as described by Vadlamudi et al. (1996, J. Biol. Chem 271:20235–20237), or interaction with CSK (see Neet and Hunter, 1995, Mol. Cell. Biol. 15:4908–4920). Finally, the human hnRNP G protein binds RNA; thus, the complexes and proteins of the invention can be screened by measuring their affect on the levels of hnRNP G protein binding to RNA.

The 53BP2 binding partners β-tubulin and p62 have been implicated in cellular apoptosis, mRNA destabilization and ubiquitin-mediated proteolysis associated with neurodegenerative disease. The 53BP2:53B2-IP complexes (particularly the 53BP2:β-tubulin and 53BP2:p62 complexes) and derivatives, analogs and fragments thereof, nucleic acids encoding the 53BP2 and 53BP2-IP genes, anti-53BP2:53BP2-IP antibodies, and other modulators of 53BP2:53BP2-IP complex activity can be tested for activity in treating or preventing neurodegenerative disease in in vitro and in vivo assays.

In one embodiment, a Therapeutic of the invention can be assayed for activity in treating or preventing neurodegenerative disease by contacting cultured cells that exhibit an indicator of a neurodegenerative disease, for example but not limited to, hypersecretion of B-A4 peptide (Nakajima et al., 1985, Proc. Natl. Acad. Sci. USA 82:6325–6329) in vitro with the Therapeutic; and comparing the level of said indicator in the cells contacted with the Therapeutic, with said level of said indicator in cells not so contacted, wherein a lower level in said contacted cells indicates that the Therapeutic has activity in treating or preventing neurodegenerative disease. Specific examples of such cultured models for neurodegenerative disease include, but are not limited to: cultured rat endothelial cells from affected and nonaffected individuals (Maneiro et al., 1997, Methods Find. Exp. Clin. Pharmacol., 19:5–12); P19 murine embryonal carcinoma cells (Hung et al., 1992, Proc Natl Acad Sci USA 1992, 89:9439–9443); and dissociated cell cultures of cholinergic neurons from nucleus basalis of Meynert (Nakajima et al., 1985, Proc Natl Acad Sci USA, 82:6325–6329).

In another embodiment, a Therapeutic of the invention can be assayed for activity in treating or preventing neurodegenerative disease by administering the Therapeutic to a test animal that exhibits symptom of a neurodegenerative disease, such as, but not limited to, cognitivie dysfunction in behavior maze test, or that is predisposed to develop symptoms or a neurodegenerative disease; and measuring the change in said symptoms of the neurodegenerative disease after administration of said Therapeutic, wherein a reduction in the severity of the symptoms of the neurodegenerative or prevention of the symptoms of the neurodegenerative disease indicates that the Therapeutic has activity in treating or preventing neurodegenerative disease. Such a test animal can be any one of a number of animal models known in the art for neurodegenerative disease. These models, including those for Alzheimer's Disease and mental retardation of trisomy 21 accurately mimic natural human autoimmune diseases (Farine, 1997, Toxicol. 119:29–35). Examples of specific models include but are not limited to: the partial trisomy 16 mouse (Holtzman et al., 1996, Proc. Natl. Acad. Sci. USA 93:13333–13338); bilateral nucleus basalis magnocellularis-lesioned rats (Popovic et al., 1996, Int. J. Neurosci. 86:281–299); the aged rat (Muir, 1997, Pharmacol. Biochem. Behav. 56:687–696); the PDAPP transgenic mouse model of Alzheimer disease (Johnson-Wood et al., 1997, Proc. Natl. Acad. Sci. USA 94:1550–1555); and experimental autoimmune dementia (Oron et al., 1997, J. Neural Transm. Suppl. 49:77–84).

The 53BP2 binding partner hnRNPG has been implicated in autoimmune disease. Accordingly, 53BP2:53BP2-IP complexes, particularly 53BP2:hnRNP G complexes, and derivatives, analogs, and fragments thereof, nucleic acids encoding the 53BP2 and 53BP2-IP genes, anti-53BP2:53BP2-IP antibodies, and other modulators of the 53BP2:53BP2-IP complex activity can be tested for activity in treating or preventing neurodegenerative disease in in vitro and in vivo assays.

In one embodiment, a Therapeutic of the invention can be assayed for activity in treating or preventing autoimmune disease by contacting cultured cells that exhibit an indicator of an autoimmune reaction in vitro, such as but not limited to, secretion of chemokines (Kunkel et al., 1996, J. Leukoc. Biol. 59:6–12) with the Therapeutic, and comparing the level of said indicator in the cells contacted with the Therapeutic with said level of said indicator in cells not so contacted, wherein a lower level in said contacted cells indicates that the Therapeutic has activity in treating or preventing autoimmune disease. Cell models that can be used for such assays include, but are not limited to: leukocyte and other synovial cells that secrete chemokines mediating inflammation (Kunkel et al., 1996, J. Leukoc. Biol. 59:6–12); cerebrospinal fluid cells from animal models of multiple sclerosis (Norga et al., 1995, Inflamm. Res. 44:529–534); macrophages in experimental autoimmunoneuritis (model of Guillain-Barre Disease (Bai et al., 1997, J. Neuroimmunol. 76:177–184); CD40/CD40L assays in monocytes (Laman et al., 1996, Crit. Rev. Immunol. 16:59–108); lymphocyte cultures for lpr mice (Nagata, 1996, Prog. Mol. Subcell. Biol. 16:87–103); and cultured thyrocytes in spontaneous murine autoimmune thyroiditis (Green et al., 1996, Endocrinology 137:2823–2832).

In another embodiment, a Therapeutic of the invention can be assayed for activity in treating or preventing autoimmune disease by administering said Therapeutic to a test animal exhibiting an autoimmune reaction or which test animal does not exhibit an autoimmune reaction and is subsequently challenged with an agent that elicits an autoimmune reaction; and measuring the change in the autoimmune reaction after the administration of said Therapeutic, wherein a reduction in said autoimmune reaction or a prevention of said autoimmune reaction indicates that the Therapeutic has activity in treating or preventing an autoimmune disease.

A number of animal models of autoimmune disease are known in the art. These models, including those for arthritis, systemic lupus erythematosus, diabetes, thyroiditis, encephalitis etc., accurately mimic natural human autoimmune diseases (Farine, 1997, Toxicol. 119:29–35). Examples of specific models include but are not limited to: experimental allergic encephalomyelitis for multiple sclerosis (Brabb et al., 1997, J. Immunol. 159:497–507); thyroglobulin-induced experimental thyroiditis (Bhatia et al., 1996 et al., 1996 213:294–300); multiple organ-localized autoimmune disease, e.g., thyroiditis and gastritis in BALB/c nu/nu mice receiving rat thymus grafts under their renal capsules (Taguchi and Takahashi, 1996, Immunology 89:13–19); virus-induced autoimmune diseases such as insulin-dependent diabetes mellitus (Oldstone and von Herath, 1996), experimental autoimmune encephalomyelitis (Encinas et al., 1996, J. Neurosci. Res. 45:655–669); experimental autoimmune labyrinthitis; Freund's-adjuvant induced rheumatoid arthritis and inbred mouse strains that develop systemic lupus erythematosus, rheumatoid arthritis, graft-vs-host disease, and diabetes (Humphryes-Beher, 1996, Adv. Dent. Res. 10:73–75); autoimmune hepatitis (Meyer zum Buschenfelde and Dienes, 1996, Virchows Arch. 429:1–12).

Screening for Antagonists and Agonists of 53BP2:53BP2-IP Complex and 53BP2-IP1, 53BP2-IP2, and 53BP2-IP3

53BP2:53BP2-IP complexes, 53BP2-IP1, 53BP2-IP2, 53BP2-IP3 and derivatives, fragments and analogs thereof, as well as nucleic acids encoding 53BP2 and 53BP2-IPs and 53BP2-IP1, 53BP2-IP2, and 53BP2-IP3 as well as derivatives, fragments and analogs thereof, can be used to screen for compounds that bind to 53BP2:53BP2-IP and 53BP2-IP1, 53BP2-IP2, and 53BP2-IP3 nucleic acids, proteins, or derivatives and thus have potential use as agonists or antagonists of 53BP2:53BP2-IP complex or 53BP2-IP1, 53BP2-IP2, or 53BP2-IP3 protein function. The invention thus provides assays to detect molecules that specifically bind to 53BP2 and 53BP2-IP, and 53BP2-IP1, 53BP2-IP2, and 53BP2-IP3 nucleic acids, proteins or derivatives. For example, recombinant cells expressing both 53BP2 and 53BP2-IP nucleic acids or 53BP2-IP1, 53BP2-IP2, or 53BP2-IP3 nucleic acids can be used to recombinantly produce the complexes or proteins in these assays, to screen for molecules that bind or interfere with 53BP2:53BP2-IP complexes or 53BP2-IP1, 53BP2-IP2, or 53BP2-IP3 function. In preferred embodiments, polypeptide analogs that have superior stabilities (but retain the ability to form 53BP2:53BP2-IP complexes), e.g. 53BP2 and 53BP2-IPs modified to be resistant to proteolytic degradation in the binding assay buffers, or to be resistant to oxidative degradation are used to screen for modulators (e.g. molecules generated by substitution of amino acids at proteolytic cleavage sites, the use of chemically derivatized amino acids at proteolytic susceptible sites, and replacement of amino acid residues subject to oxidation, i.e. methionine and cysteine).

Molecules (e.g. putative binding partners of a 53BP2:53BP2-IP complex or of 53BP2-IP1, 53BP2-IP2, or 53BP2-IP3) are contacted with the 53BP2:53BP2-IP complex or 53BP2-IP1, 53BP2-IP2, or 53BP2-IP3 proteins (or fragment thereof) under conditions conducive to binding, and then molecules that specifically bind to 53BP2:53BP2-IP complexes or 53BP2-IP1, 53BP2-IP2, or 53BP2-IP3 proteins are identified. Similar methods can be used to screen for molecules that bind to 53BP2:53BP2-IP or 53BP2-IP1, 53BP2-IP2, or 53BP2-IP3 nucleic acids or derivatives.

A particular aspect of the invention relates to identifying molecules that inhibit or promote formation or degradation of a 53BP2:53BP2-IP complex, e.g. using the method described for screening inhibitors using the modified yeast two hybrid assay described in Section 5.7.1., infra and in U.S. patent application Ser. No. 08/663,824, filed Jun. 14, 1996, and Ser. No. 08/874,825, filed Jun. 13, 1997, both entitled "Identification and Comparison of Protein—Protein Interactions that Occur in Populations and Identification of Inhibitors of These Interactions", and both by Nandabalan et al., which are incorporated by reference herein in their entireties.

In one embodiment of the invention, a molecule that modulates activity of 53BP2 or a protein selected from the group consisting of β-tubulin, p62, hnRNP G, 53BP2-IP1, 53BP2-IP2, and 53BP2-IP3 or a complex of 53BP2 and said protein is identified by contacting one or more candidate molecules with 53BP2 in the presence of said protein; and measuring the amount of complex that forms between 53BP2 and said protein; wherein an increase or decrease in the amount of complex that forms relative to the amount that forms in the absence of the candidate molecules indicates that the molecules modulate the activity of 53BP2 or said protein or said complex of 53BP2 and said protein. In preferred embodiments, the modulators are identified by administering the candidate molecules to a transgenic non-human animal expressing both 53BP2 and a 53BP2-IP from promoters that are not the native 53BP2 or the native 53BP2-IP promoters, more preferably where the candidate molecules are also recombinantly expressed in the transgenic non-human animal. Alternatively, the method for identifying such modulators can be carried out in vitro, preferably with purified 53BP2, purified 53BP2-IP, and purified candidate molecules.

Methods that can be used to carry out the foregoing are commonly known in the art. Agents to be screened can be provided as mixtures of a limited number of specified compounds, or as compound libraries, peptide libraries and the like. Agents to be screened may also include all forms of antisera, antisense nucleic acids, etc. that can modulate 53BP2:53BP2-IP complex activity or 53BP2-IP1, 53BP2-IP2, or 53BP2-IP3 activity.

By way of example, diversity libraries, such as random or combinatorial peptide or nonpeptide libraries can be screened for molecules that specifically bind to a 53BP2:53BP2-IP complex or 53BP2-IP1, 53BP2-IP2, or 53BP2-IP3 protein. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and PCT Publication No. WO 94/18318.

In a specific embodiment, screening can be carried out by contacting the library members with a 53BP2:53BP2-IP complex or a 53BP2-IP1, 53BP2-IP2, or 53BP2-IP3 protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another specific embodiment, fragments and/or analogs of 53BP2 or a 53BP2-IP, especially peptidomimetics, are screened for activity as competitive or non-competitive inhibitors of 53BP2:53BP2-IP complex formation, and thereby inhibit 53BP2-IP complex activity.

In a preferred embodiment, molecules that bind to 53BP2:53BP2-IP complexes and 53BP2-IP1, 53BP2-IP2, and 53BP2-IP3 proteins can be screened for using the modified yeast two hybrid system described in Section 5.7.1 and exemplified in Section 6.1, infra.

In one embodiment, agents that modulate (i.e. inhibit, antagonize, or agonize) 53BP2:53BP2-IP complex activity can be screened using a binding inhibition assay, wherein agents are screened for their ability to inhibit formation of a 53BP2:53BP2-IP complex under aqueous, or physiological, binding conditions in which 53BP2:53BP2-IP complex formation occurs in the absence of the agent to be tested. Agents that interfere with the formation of 53BP2:53BP2-IP complexes are identified as antagonists of complex formation.

Methods for screening may involve labeling the complex proteins with radioligands (e.g. $^{125}I$ or 3H), magnetic ligands (e.g. paramagnetic beads covalently attached to photobiotin acetate), and florescent ligands (e.g. fluorescein or rhodamine) or enzyme ligands (e.g. luciferase or beta-galactosidase). The reactants that bind in solution can then be isolated by one of many techniques known in the art, including but not restricted to, co-immunoprecipitation of the labeled moiety using antisera against the unlabeled binding partner (or labeled binding partner with a distinguishable marker from that used on the labeled moiety) protein, immunoaffinity chromatography, size exclusion chromatography, and gradient density centrifugation. In a preferred embodiment, one binding partner is a small fragment or peptidomimetic that is not retained by a commercially available filter. Upon binding, the labeled species is then unable to pass through the filter, providing for a simple assay of complex formation.

Methods commonly known in the art are used to label at least one of the members of the 53BP2:53BP2-IP complex. Suitable labeling includes, but is not limited to, radiolabeling by incorporation of radiolabeled amino acids, e.g. $^3H$-leucine of $^{35}S$-methionine, radiolabeling by post-translational iodination with $^{125}I$ or $^{131}I$ using the chloramine T method, Bolton-Hunter reagents, etc., or labeling with $^{32}P$ using phosphorylase and inorganic radiolabeled phosphorous, biotin labeling with photobiotin-acetate and sunlamp exposure, etc. In cases where one of the members of the 53BP2:53BP2-IP complex is immobilized, e.g. as described infra, the free species is labeled. Where neither of the interacting species is immobilized, each can be labelled with a distinguishable marker such that isolation of both moieties can be followed to provide for more accurate quantitation, and to distinguish the formation of homomeric from heteromeric complexes. Methods that utilize accessory proteins that bind to one of the modified interactants to improve the sensitivity of detection, increase the stability of the complex, etc. are provided.

Typical binding conditions are, for example, but not by way of limitation, in an aqueous salt solution of 10–250 mM NaCl, 5–50 mM Tris-HCl, pH 5–8, 0.5% Triton X-100 or other detergent that improves specificity of interaction. Metal chelators and/or divalent cations may be added to improve binding and/or reduce proteolysis. Reaction temperatures may include 4, 10, 15, 22, 25, 35, or 42 degrees Celsius, and time of incubation is typically at least 15 seconds, but longer times are preferred to allow binding equilibrium to occur. Particular 53BP2:53BP2-IP complexes can be assayed using routine protein binding assays to determine optimal binding conditions for reproducible binding.

The physical parameters of complex formation can be analyzed by quantitation of complex formation using assay methods specific for the label used, e.g. liquid scintillation counting for radioactivity detection, enzyme activity measurements for enzyme label, etc. The reaction results are then analyzed utilizing Scatchard analysis, Hill analysis, and other methods commonly known in the arts (see, e.g., *Proteins, Structures, and Molecular Principles*, (1984) Creighton, ed., W. H. Freeman and Company, New York).

In a second common approach to binding assays, one of the binding species is immobilized on a filter, in a microtiter plate well, in a test tube, to a chromatography matrix, etc., either covalently or non-covalently. Proteins can be covalently immobilized using any method well known in the art, for example, but not limited to the method of Kadonaga and Tjian (1986, Proc. Natl. Acad. Sci. USA 83: 5889–5893, 1986), i.e., linkage to a cyanogen-bromide derivatized substrate such as CNBr-Sepahrose 4B. Where needed, the use of spacers can reduce steric hindrance from the substrate. Non-covalent attachment of proteins to a substrate include, but are not limited to, attachment of a protein to a charged surface, binding with specific antibodies, binding to a third unrelated IP, etc.

In one embodiment, immobilized 53BP2 is used to assay for binding with a radioactively-labeled 53BP2-IP in the presence and absence of a compound to be tested for its ability to modulate 53BP2:53BP2-IP complex formation. The binding partners are allowed to bind under aqueous, or physiological, conditions (e.g. the conditions under which the original interaction was detected). Conversely, in another embodiment, the 53BP2-IP is immobilized and contacted with the labeled 53BP2 protein or derivative thereof under binding conditions.

Assays of agents (including cell extracts or library pool) for competition for binding of one member of a 53BP2:53BP2-IP complex (or derivatives thereof) with the other member of the 53BP2:53BP2-IP complex (labeled by any means, e.g. those means described supra), are provided to screen for competitors of 53BP2:53BP2-IP complex formation.

In specific embodiments, blocking agents to inhibit non-specific binding of reagents to other protein components, or absorptive losses of reagents to plastics, immobilization matrices, etc., are included in the assay mixture. Blocking agents include, but are not restricted to bovine serum albumin, beta-casein, nonfat dried milk, Denhardt's reagent, Ficoll, polyvinylpyrolidine, nonionic detergents(NP40, Triton X-100, Tween 20, Tween 80, etc.), ionic detergents (e.g. SDS, LDS, etc.), polyethyleneglycol, etc. Appropriate blocking agent concentrations allow 53BP2:53BP2-IP complex formation.

After binding is performed, unbound, labelled protein is removed in the supernatant, and the immobilized protein with any bound, labelled protein is washed extensively. The amount of label bound is then quantitated using standard methods in the art to detect the label as described supra.

Assays for Proteins-Protein Interactions

One aspect of the present invention provides methods for assaying and screening fragments, derivatives and analogs of derivatives, analogs and fragments of 53BP2-interacting proteins (for binding to 53BP2 peptides). Derivatives, analogs and fragments of 53BP2-IPs that interact with 53BP2 can be identified by means of a yeast two hybrid assay system (Fields and Song, 1989, Nature 340: 245–246; U.S. Pat. No. 5,283,173 by Fields and Song) or, more preferably, an improvement thereof as described in U.S. patent application Ser. No. 08/663,824, filed Jun. 14, 1996, and Ser. No. 08/874,825, filed Jun. 13, 1997, both entitled "Identification and Comparison of Protein-Protein Interactions that Occur in Populations and Identification of Inhibitors of These Interactions", and both by Nandabalan et al., which are incorporated by reference herein in their entireties. Because the interactions are screened for in yeast, the intermolecular protein interactions detected in this system generally occur under physiological conditions that mimic the conditions in mammalian cells (Chien et al., 1991, Proc. Natl. Acad. Sci. USA 88: 9578–9581.)

Identification of interacting proteins by the improved yeast two hybrid system is based upon the detection of the expression of a reporter gene ("Reporter Gene"), the transcription of which is dependent upon the reconstitution of a transcriptional regulator by the interaction of two proteins, each fused to one half of the transcriptional regulator. The bait (53BP2 or derivative or analog) and prey (proteins to be tested for ability to interact with the bait) proteins are expressed as fusion proteins to a DNA binding domain, and to a transcriptional regulatory domain, respectively, or vice versa. In various specific embodiments, the prey has a complexity of at least 50, 100, 500, 1,000, 5,000, 10,000, or 50,000; or has a complexity in the range of 25 to 100,000, 100 to 100,000, 50,000 to 100,000, or 10,000 to 500,000. For example, the prey population can be one or more nucleic acids encoding mutants of a 53BP2-IP (e.g., as generated by site-directed mutagenisis or another method of making mutations in a nucleotide sequence). Preferably, the prey populations are proteins encoded by DNA, e.g., cDNA or genomic DNA or synthetically generated DNA. For example, the populations can be expressed from chimeric genes comprising cDNA sequences from an un-characterized sample of a population of cDNA from mammalian RNA. Preferably, the prey population are proteins encoded by DNA, e.g., cDNA or genomic DNA or synthetically generated DNA.

In a specific embodiment, recombinant biological libraries expressing random peptides can be used as the source of prey nucleic acids.

In another embodiment, the invention provides methods for screening for inhibitors of the interacting proteins identified herein. Briefly, the protein-protein interaction assay can be carried out as described herein, except that it is done in the presence of one or more candidate molecules. An increase or decrease in Reporter Gene activity relative to that present when the one or more candidate molecules are absent indicates that the candidate molecule has an effect on the interacting pair. In a preferred method, inhibition of the interaction is selected for (i.e. inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101:167–180). The identification of inhibitors of such interactions can also be accomplished, for example, but not by way of limitation, using competitive inhibitor assays, as described supra.

In general, proteins of the bait and prey populations are provided as fusion (chimeric) proteins (preferably by recombinant expression of a chimeric coding sequence) containing each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the method of the invention, binding of a 53BP2 fusion protein to a prey fusion protein leads to reconstitution of a transcriptional activator (or inhibitor) which activates (or inhibits) expression of the Reporter Gene. The activation of transcription of the Reporter Gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native. Thus, for example, one or more tandem copies (e.g., 4 or 5 copies) of the appropriate DNA binding site can be introduced upstream of the TATA box in the desired promoter (e.g., in the area of position –100 to –400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1-10 promoter is operably fused to the desired nucleotide sequence; the GAL1-10 promoter already contains 5 binding sites for GAL4. Alternatively, the transcriptional activation binding site of the desired gene(s) can be deleted and replaced with GAL4 binding sites (Bartel et al., 1993, BioTechniques 14(6):920–924; Chasman et al., 1989, Mol. Cell. Biol. 9:4746–4749). The Reporter Gene preferably contains the sequence encoding a detectable or selectable marker the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator). In one embodiment, more than one Reporter Gene is used to detect transcriptional activation, e.g., one Reporter Gene encoding a detectable marker and one or more Reporter Genes encoding different selectable markers. The detectable marker can be any molecule that can give rise to a detectable signal, e.g., a fluorescent protein or a protein that can be readily visualized or that is recognizable by a specific antibody. The selectable marker can be any protein molecule that confers ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The Reporter Gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of S. cerevisiae, the GCN4 protein of S. cerevisiae (Hope and Struhl, 1986, Cell 46:885–894), the ARD1 protein of S. cerevisiae (Thukral et al., 1989, Mol. Cell. Biol. 9:2360–2369), and the human estrogen receptor (Kumar et al., 1987, Cell 51:941–951) have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) is the activation domain.

In a preferred embodiment, the yeast transcription factor GAL4 is reconstituted by the protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The Reporter Gene can also be a CUP1-lacZ fusion that expresses the enzyme β-galactosidase (detectable by routine chromogenic assay) upon binding of a reconstituted Ace1N transcriptional activator (see Chaudhuri et al., 1995, FEBS Letters 357:221–226). In another specific embodiment, the DNA binding domain of the human estrogen receptor is used, with a Reporter Gene driven by one or three estrogen receptor response elements (Le Douarin et al., 1995, Nucl. Acids. Res. 23:876–878).

The DNA binding domain and the transcription activator/inhibitor domain each preferably has a nuclear localization signal (see Ylikomi et al., 1992, EMBO J. 11:3681–3694; Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells (see Allen et al., 1995, TIBS 20:511–516).

The host cell in which the interaction assay occurs can be any cell, prokaryotic or eukaryotic, in which transcription of the Reporter Gene can occur and be detected, including but not limited to mammalian (e.g., monkey, chicken, mouse, rat, human, bovine), bacteria, and insect cells, and is preferably a yeast cell. Expression constructs encoding and capable of expressing the binding domain fusion proteins, the transcriptional activation domain fusion proteins, and the Reporter Gene product(s) are provided within the host cell, by mating of cells containing the expression constructs, or by cell fusion, transformation, electroporation, microinjection, etc. In a specific embodiment in which the assay is carried out in mammalian cells (e.g., hamster cells), the DNA binding domain is the GAL4 DNA binding domain, the activation domain is the herpes simplex virus VP16 transcriptional activation domain, and the Reporter Gene contains the desired coding sequence operably linked to a minimal promoter element from the adenovirus E1B gene driven by several GAL4 DNA binding sites (see Fearon et al., 1992, Proc. Natl. Acad. Sci. USA 89:7958–7962). The host cell used should not express an endogenous transcription factor that binds to the same DNA site as that recognized by the DNA binding domain fusion population. Also, preferably, the host cell is mutant or otherwise lacking in an endogenous, functional form of the Reporter Gene(s) used in the assay.

Various vectors and host strains for expression of the two fusion protein populations in yeast are known and can be used (see, e.g., Fields et al., U.S. Pat. No. 5,1468,614 dated Nov. 21, 1995; Bartel et al., 1993, "Using the two-hybrid system to detect protein-protein interactions," in *Cellular Interactions in Development*, Hartley, D. A. (ed.), Practical Approach Series xviii, IRL Press at Oxford University Press, New York, N.Y., pp. 153–179; Fields and Sternglanz, 1994, TIG 10:286–292). By way of example but not limitation, yeast strains or derivative strains made therefrom, which can be used are N105, N106, N1051, N1061, and YULH, as described in Section 6.3, infra. Exemplary strains that can be used in the assay of the invention also include, but are not limited to, the following: Y190: MATa, ura3-52, his3-200, lys2-801, ade2-101, trp1-901, leu2-3,112, gal4Δ, gal80Δ, cyh$^r$2, LYS2::GAL1$_{UAS}$-HIS3$_{TATA}$HIS3, URA3::GAL1$_{UAS}$-GAL1$_{TATA}$-lacZ (available from Clontech, Palo Alto, Calif.; Harper et al., 1993, Cell 75:805–816). Y190 contains HIS3 and lacZ Reporter Genes driven by GAL4 binding sites. CG-1945: MATa, ura3-52, his3-200, lys2-801, ade2-101, trp1-901, leu2-3,112, gal4-542, gal80-538, cyhr$^r$2, LYS2::GAL1$_{UAS}$-HIS3$_{TATA}$HIS3, URA3::GAL1$_{UAS17mers(\times 3)}$-CYC1$_{TATA}$-laCZ (available from Clontech). CG-1945 contains HIS3 and lacZ Reporter Genes driven by GAL4 binding sites. Y187: MAT-α, ura3-52, his3-200, ade2-101, trp1-901, leu2-3,112, gal4Δ, gal80Δ, URA3:: GAL1$_{UAS}$-GAL1$_{TATA}$-lacZ (available from Clontech). Y187 contains a lacZ Reporter Gene driven by GAL4 binding sites. SFY526: MATa, ura3-52, his3-200, lys2-801, ade2-101, trp1-901, leu2-3,112, gal4-542, gal80-538, can$^r$,URA3::GAL1-lacZ (available from Clontech). SFY526 contains HIS3 and lacZ Reporter Genes driven by GAL4 binding sites. HF7c: MATa, ura3-52, his3-200, lys2-801, ade2-101, trp1-901, leu2-3,112, gal4-542, gal80-538, LYS2::GAL1-HIS3. URA3::GAL1$_{UAS\ 17\ MERS\ (\times 3)}$-CYC1-lacZ (available from Clontech). HF7c contains HIS3 and lacZ Reporter Genes driven by GAL4 binding sites. YRG-2: MATa, ura3-52, his3-200, lys2-801, ade2-101, trp1-901, leu2-3,112, gal4-542, gal80-538 LYS2::GAL1$_{UAS}$-GAL1$_{TATA}$-HIS3, URA3::GAL1$_{UAS\ 17mers\ (\times 3)}$-CYC1-lacZ (available from Stratagene). YRG-2 contains HIS3 and lacZ Reporter Genes driven by GAL4 binding sites.

Many other strains commonly known and available in the art can be used.

If not already lacking in endogenous Reporter Gene activity, cells mutant in the Reporter Gene may be selected by known methods, or the cells can be made mutant in the target Reporter Gene by known gene-disruption methods prior to introducing the Reporter Gene (Rothstein, 1983, Meth. Enzymol. 101:202–211).

In a specific embodiment, plasmids encoding the different fusion protein populations can be both introduced into a single host cell (e.g., a haploid yeast cell) containing one or more Reporter Genes, by co-transformation, to conduct the assay for protein-protein interactions. Or, preferably, the two fusion protein populations are introduced into a single cell either by mating (e.g. for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, delivers both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed, using two different types of host cells, strain-types a and alpha, of the yeast *Saccharomyces cerevisiae*. The host cell preferably contains at least two Reporter Genes, each with one or more binding sites for the DNA-binding domain (e.g., of a transcriptional activator).

The activator domain and DNA binding domain are each parts of chimeric proteins formed from the two respective populations of proteins. One set of host cells, for example the a strain cells, contains fusions of the library of nucleotide sequences with the DNA-binding domain of a transcriptional activator, such as GAL4. The hybrid proteins expressed in this set of host cells are capable of recognizing the DNA-binding site on the Reporter Gene. The second set of yeast host cells, for example alpha strain cells, contains nucleotide sequences encoding fusions of a library of DNA sequences fused to the activation domain of a transcriptional activator. In a preferred embodiment, the fusion protein constructs are introduced into the host cell as a set of plasmids. These plasmids are preferably capable of autonomous replication in a host yeast cell and preferably can also be propagated in E. coli. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70:303–312). In another embodiment, the fusion constructs are introduced directly into the yeast chromosome via homologous recombination. The homologous recombination for these purposes is mediated through yeast sequences that are not essential for vegetative growth of yeast, e.g., MER2, MER1, ZIP1, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the invention provides a method of detecting one or more protein-protein interactions comprising (a) recombinantly expressing 53BP2 or a derivative or analog thereof in a first population of yeast cells being of a first mating type and comprising a first fusion protein containing the 53BP2 sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a 53BP2-IP and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

In a preferred embodiment, the bait 53BP2 sequence and the prey library of chimeric genes are combined by mating the two yeast strains on solid media for a period of approximately 6–8 hours. In a less preferred embodiment, the mating is performed in liquid media. The resulting diploids contain both kinds of chimeric genes, i.e., the DNA-binding domain fusion and the activation domain fusion.

Preferred reporter genes include URA3, HIS3 and/or the lacZ genes (see, e.g., Rose and Botstein, 1983, Meth. Enzymol. 101:167–180) operably linked to GAL4 DNA-binding domain recognition elements. Other reporter genes comprise the functional coding sequences for, but not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 or chloramphenicol acetyl transferase (CAT). Expression of LEU2, LYS2, ADE2 and TRP1 are detected by growth in a specific defined media; GUS and CAT can be monitored by well known enzyme assays; and CAN1 and CYH2 are detected by selection in the presence of canavanine and cycloheximide. With respect to GFP, the natural fluorescence of the protein is detected.

In a specific embodiment, transcription of the Reporter Gene is detected by a linked replication assay. For example, as described by Vasavada et al. (1991, Proc. Natl. Acad. Sci. USA 88:10686–10690), expression of SV40 large T antigen is under the control of the ElB promoter responsive to GAL4 binding sites. The replication of a plasmid containing the SV40 origin of replication, indicates the reconstruction of the GAL4 protein and a protein-protein interaction. Alternatively, a polyoma virus replicon can be employed (Vasavada et al., 1991, Proc. Natl. Acad. Sci. USA 88:10686–0690).

In another embodiment, the expression of Reporter Genes that encode proteins can be detected by immunoassay, i.e., by detecting the immunospecific binding of an antibody to such protein, which antibody can be labeled, or alternatively, which antibody can be incubated with a labeled binding partner to the antibody, so as to yield a detectable signal. Alam and Cook (1990, Anal. Biochem. 188:245–254) disclose non-limiting examples of detectable marker genes that can be operably linked to a transcriptional regulatory region responsive to a reconstituted transcriptional activator, and thus used as Reporter Genes.

The activation of Reporter Genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine, respectively (referred to as –URA (minus URA) and –HIS (minus HIS) medium, respectively). The –HIS medium preferably contains 3-amino-1,2,4-triazole (3-AT), which is a competitive inhibitor of the HIS3 gene product and thus requires higher levels of transcription in the selection (see Durfee et al., 1993, Genes Dev. 7:555–569). Similarly, 6-azauracil, which is an inhibitor of the URA3 gene product, can be included in –URA medium (Le Douarin et al., 1995, Nucl. Acids Res. 23:876–878). URA3 gene activity can also be detected and/or measured by determining the activity of its gene product, orotidine-5 1-monophosphate decarboxylase (Pierrat et al., 1992, Gene 119:237–245; Wolcott et al., 1966, Biochem. Biophys. Acta 122:532–534). In other embodiments of the invention, the activities of the reporter genes like lacZ or GFP are monitored by measuring a detectable signal (e.g., fluorescent or chromogenic) that results from the activation of these Reporter Genes. For example, lacZ transcription can be monitored by incubation in the presence of a chromogenic substrate, such as X-gal (5-bromo-4-chloro-3-indolyl-α-D-galactoside), for its encoded enzyme, β-galactosidase. The pool of all interacting proteins isolated by this manner from mating the 53BP2 sequence product and the library identifies the "53BP2 interactive population".

In a preferred embodiment of the invention, false positives arising from transcriptional activation by the DNA binding domain fusion proteins in the absence of a transcriptional activator domain fusion protein are prevented or reduced by negative selection for such activation within a host cell containing the DNA binding fusion population, prior to exposure to the activation domain fusion population. By way of example, if such cell contains URA3 as a Reporter Gene, negative selection is carried out by incubating the cell in the presence of 5-fluoroorotic acid (5-FOA, which kills URA+ cells (Rothstein, 1983, Meth. Enzymol. 101:167–180). Hence, if the DNA-binding domain fusions by themselves activate transcription, the metabolism of 5-FOA will lead to cell death and the removal of self-activating DNA-binding domain hybrids.

Negative selection involving the use of a selectable marker as a Reporter Gene and the presence in the cell medium of an agent toxic or growth inhibitory to the host cells in the absence of Reporter Gene transcription is preferred, since it allows a higher rate of processing than other methods. As will be apparent, negative selection can also be carried out on the activation domain fusion population prior to interaction with the DNA binding domain fusion population, by similar methods, either alone or in addition to negative selection of the DNA binding fusion population.

Negative selection can also be carried out on the recovered 53BP2:53BP2-IP pairs by known methods (see, e.g., Bartel et al., 1993, BioTechniques 14:920–924) although pre-negative selection (prior to the interaction assay), as described above, is preferred. For example, each plasmid encoding a protein (peptide or polypeptide) fused to the activation domain (one-half of a detected interacting pair) can be transformed back into the original screening strain, either alone or with a plasmid encoding only the DNA-binding domain, the DNA-binding domain fused to the detected interacting protein, or the DNA-binding domain fused to a protein that does not affect transcription or participate in the protein-protein interaction; a positive interaction detected with any plasmid other than that encoding the DNA-binding domain fusion to the detected interacting protein is deemed a false positive and eliminated from the screen.

In a preferred embodiment, the 53BP2 plasmid population is transformed in a yeast strain of a first mating type (a or alpha), and the second plasmid population (containing the library of DNA sequences) is transformed in a yeast strain of different mating type. Both strains are preferably mutant for URA3 and HIS3, and contain HIS3, and optionally lacZ, as a Reporter Genes. The first set of yeast cells are positively selected for the 53BP2 plasmids and are negatively selected for false positives by incubation in medium lacking the selectable marker (e.g., tryptophan) and containing 5-FOA. Yeast cells of the second mating type are transformed with the second plasmid population, and are positively selected for the presence of the plasmids containing the library of fusion proteins. Selected cells are pooled. Both groups of pooled cells are mixed together and mating is allowed to occur on a solid phase. The resulting diploid cells are then transferred to selective media that selects for the presence of each plasmid and for activation of Reporter Genes.

In a preferred embodiment of the invention, after an interactive population is obtained, the DNA sequences encoding the pairs of interactive proteins are isolated by a method wherein either the DNA-binding domain hybrids or the activation domain hybrids are amplified, in separate respective reactions. Preferably, the amplification is carried out by polymerase chain reaction (PCR) (U.S. Pat. Nos. 4,683,202. 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220; Innis et al., 1990, *PCR Protocols*, Academic Press, Inc., San Diego, Calif.), using pairs of oligonucleotide primers specific for either the DNA-binding domain hybrids or the activation domain hybrids. This PCR reaction can also be performed on pooled cells expressing interacting protein pairs, preferably pooled arrays of interactants. Other amplification methods known in the art can be used, including but not limited to ligase chain reaction (see EP 320,308) use of Qβ replicase, or methods listed in Kricka et al., 1995, *Molecular Probing, Blotting, and Sequencing*, Chap. 1 and Table IX, Academic Press, New York.

The plasmids encoding the DNA-binding domain hybrid and the activation domain hybrid proteins can also be isolated and cloned by any of the methods well known in the art. For example, but not by way of limitation, if a shuttle (yeast to *E. coli*) vector is used to express the fusion proteins, the genes can be recovered by transforming the yeast DNA into *E. coli* and recovering the plasmids from *E. coli* (see, e.g., Hoffman et al., 1987, Gene 57:267–272). Alternatively, the yeast vector can be isolated, and the insert encoding the fusion protein subcloned into a bacterial expression vector, for growth of the plasmid in *E. coli*.

Pharmaceutical Compositions and Therapeutic/prophylactic Administration

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.5.6 and 5.5.7 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Animal Models

The invention also provides animal models. In one embodiment, animal models for diseases and disorders involving 53BP2:53BP2-IP complexes and 53BP2-IP1, 53BP2-IP2, and 53BP2-IP3 are provided. These include but are not limited to: cell proliferative disorders including cancer, degenerative disorders involving cellular apoptosis, and benign hypertrophy. Such animals can be initially produced by promoting homologous recombination or insertional mutagenisis between an 53BP2 and a 53BP2-IP genes or between 53BP2-IP1, 53BP2-IP2, or 53BP2-IP3 gene in the chromosome and exogenous 53BP2 and 53BP2-IP genes or 53BP2-IP1, 53BP2-IP2, or 53BP2-IP3 genes that have been rendered biologically inactive or deleted (preferably by insertion of a heterologous sequence, e.g., an antibiotic resistance gene). In a preferred aspect, this homologous recombination is carried out by transforming embryo-derived stem (ES) cells with a vector containing the insertionally inactivated 53BP2 and 53BP2-IP gene or 53BP2-IP1, 53BP2-IP2, or 53BP2-IP3 gene, such that homologous recombination occurs, followed by injecting the ES cells into a blastocyst, and implanting the blastocyst into a foster mother, followed by the birth of the chimeric animal ("knockout animal") in which a 53BP2 and a 53BP2-IP gene or 53B2-IP1, 53BP2-IP2, or 53BP2-IP3 gene has been inactivated or deleted (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving, but not restricted to, cell proliferative disorders including cancer and benign hypertrophy, various disorders involving cellular apoptosis and cellular differentiation, autoimmune diseases, etc., and thus can have use as animal models of such diseases and disorders, e.g., to screen for or test molecules (e.g., potential Therapeutics) for the ability to inhibit cell proliferative, autoimmune, and other diseases.

In a different embodiment of the invention, transgenic animals that have incorporated and express (or overexpress or misexpress) a functional 53BP2 and 53BP2-IP gene or a functional 53BP2-IP1, 53BP2-IP2, 53BP2-IP3 gene, e.g. by introducing the 53BP2 and 53BP2-IP genes or the 53BP2-IP1, 53BP2-IP2, or 53BP2-IP3 genes under the control of a heterologous promoter (i.e. a promoter that is not the native 53BP2 or 53BP2-IP promoter) that either overexpresses the protein or proteins or expresses them in tissues not normally expressing the complexes or proteins can have use as animal models of diseases and disorders characterized by elevated levels of 53BP2:53BP2-IP complexes or 53BP2-IP1, 53BP2-IP2, or 53BP2-IP3 proteins. Such animals can be used to screen for or test molecules for the ability to treat or prevent the diseases and disorders cited supra.

In one embodiment, the invention provides a recombinant non-human animal in which both an endogenous 53BP2 gene and an endogenous 53BP2-IP gene selected from the group consisting of β-tubulin, p62, hnRNP G, 53BP2-IP1, 53BP2-IP2, and 53BP2-IP3 have been deleted or inactivated by homologous recombination or insertional mutagenesis of said animal or an ancestor thereof. In another embodiment, the invention provides a recombinant non-human animal containing both a 53BP2 gene and a 53BP2-IP gene selected from the group consisting of β-tubulin, p62, hnRNP G, 53BP2-IP1, 53BP2-IP2, and 53BP2-IP3, in which the 53BP2 gene is under the control of a promoter that is not the native 53BP2 gene promoter and the 53BP2-IP gene is under the control of a promoter that is not the native 53BP2-IP gene promoter. In a specific embodiment, the invention provides a recombinant non-human animal containing a transgene comprising a nucleic acid sequence encoding a chimeric protein comprising a fragment of 53BP2 of at least 6 amino acids fused via a covalent bond to a fragment of a 53BP2-IP protein of at least 6 amino acids.

The invention also provides a recombinant non-human animal in which an endogenous 53BP2-IP gene selected from the group consisting of a 53BP2-IP1 gene, a 53BP2-IP2 gene, and a 53BP2-IP3 gene has been deleted or inactivated by homologous recombination or insertional mutagenesis of said animal or an ancestor thereof.

EXAMPLES

Identification of 53BP2:53BP2-IP Complexes

A modified, improved yeast two hybrid system was used to identify protein interactions. Yeast is a eukaryote, and therefore any intermolecular protein interactions detected in this type of system demonstrate protein interactions that occur under physiological conditions (Chien et al., 1991, Proc. Natl. Acad. Sci. USA 88: 9578–9581.) Expression vectors were constructed to encode two hybrid proteins. For a "forward" screen, one hybrid consisted of the DNA binding domain of the yeast transcriptional activator Gal4 fused to a portion of 53BP2. The other hybrid consisted of the Gal4 activator domain fused to "prey" protein sequences encoded by a mammalian cDNA library. In a "reverse" screen, the portion of 53BP2 was fused to the Gal4 activator domain, and the prey protein sequences of the mammalian cDNA library were fused to the DNA binding domain, but the assay was otherwise identically performed. Each of the vectors was then inserted into complementary (a and alpha) mating types of yeast using methods known in the art (Chien et al.,1991, supra). Mating was carried out to express both vector constructs within the same yeast cells, thus allowing interaction to occur. Interaction between the bait and prey-domains led to transcriptional activation of reporter genes containing cis-binding elements for Gal4. The reporter genes encoding the indicator protein beta-galactosidase, and metabolic markers for uracil and histidine auxotrophy, were included in specific fashion in one or the other of the yeast strains used in the mating. In this way, yeast were selected for successful mating, expression of both fusion construct, and expression of 53BP2-IPs. Yeast clones that contained interacting regions were picked and grown in individual wells of microtiter plates. The plasmids containing the 53BP2-IPs were then isolated and characterized.

The prey cDNAs were obtained from a fetal brain cDNA library of $1.5\times10^6$ independent isolates. The library was synthesized from Xho 1-dT$_{15}$ primed fetal brain mRNA (from five male/female 19–22 week fetuses) that was directionally cloned into pBD-Gal4, a yeast Gal4 DNA binding domain cloning vector including the TRYP gene for selection in yeast deficient in tryptophan biosynthesis.

A reverse screen was used to test the interaction of prey cDNA products against an array of 22 bait proteins, one of which was encoded by the 53BP2 nucleotide sequence of nucleotides 2866–3771 as depicted in FIG. 1 (SEQ ID NO:1), including amino acids 704–1005 of the 53BP2 amino acid sequence at the C-terminus of 53BP2, as depicted in FIG. 1 (SEQ ID NO:2). The bait fragment was amplified from a Clontech λgt11 library by polymerase chain reaction (PCR) using the forward primer 5'GGACTAGGCCGAG-GTGGCCTCTCCAGGCCTTGATTATGAGCCTG3' (SEQ ID NO:14) and the reverse primer 5'GGACTAGGCCTC-CTCGGCCCTACCTCTGCACTATGTCACTGATTTC3' (SEQ ID NO:15) by standard techniques. The fragment was cloned into the Sfi I site of the vector pACT-Sfi I, constructed by introducing an Sfi I-containing polylinker into the vector pACT2 (Clontech). This vector is a yeast activation domain cloning vector that contains the LEU2 gene for selection in yeast strains deficient in leucine biosynthesis. The bait was sequenced to confirm that PCR amplification reproduced an accurate copy of the 53BP2 sequence (FIG. 1). This test determined that, as predicted, the bait sequence encoded an interacting domain identical to the human 53BP2 beginning at amino acid 704 (FIG. 1).

The bait was transformed by lithium acetate/polyethylene glycol transformation (Ito et al., 1983, J. Bacteriol. 153:163–168) into the yeast strain N106$^r$ (mating type a, ura3, his3, ade2, trp1, leu2, gal4, gal80, cyh$^r$, Lys2::GAL1$_{UAS}$-HIS3$_{TATA}$-HIS3, ura 3::GAL1$_{UAS}$-GAL$_{TATA}$-lacZ), while the prey sequences were transformed into the yeast strain YULH (mating type alpha, ura3, his3, lys2, Ade2, trp1, leu2, gal4, gal80, GAL1-lacZ, GAL1-URA3). The two transformed populations were then mated using standard methods in the art (Sherman et al., eds., 1991, Getting Started with Yeast, Vol. 194, Academic Press, New York). Briefly, cells were grown until mid-to-late log phase on media that selected for the presence of the appropriate plasmids. The two mating strains, alpha and a, were then, diluted in YAPD media (Sherman et al., eds., 1991, *Getting Started with Yeast*, Vol. 194, Academic Press, New York), filtered onto nitrocellulose membranes, and incubated at 30 degrees Celsius for 6–8 hours. The cells were then transferred to media selective for the desired diploids, i.e., yeast harboring reporter genes for beta-galactosidase, uracil auxotrophy, and histidine auxotrophy, and expression of the vectors encoding the bait and prey. The mating products were plated on SC (synthetic complete) (Kaiser et al. eds., 1994, *Methods in Genetics*, 1994 ed., Cold Spring Harbor Press, New York, p. 209) media lacking adenine and lysine (to select for successful mating), leucine and tryptophan (to select for expression of genes encoded by both the bait and prey plasmids), and uracil and histidine (to select for protein interactions). This medium is herein referred to as SCS medium, for SC Selective medium.

Selected clones were tested for expression of β-galactosidase to confirm the formation of a 53BP2:53BP2-IP interaction. Filter-lift β-galactosidase assays were performed as modified from the protocol of Breeden and Nasmyth (1985, Cold Spring Harbor Quant. Biol. 50:643–650). Colonies were patched onto SCS plates, grown overnight, and replica plated onto Whatman No. 1 filters. The filters were then assayed for β-galactosidase activity. Colonies that were positive turned a visible blue.

Cells in colonies positive for protein interaction contained admixture of DNA-binding and activation-domain plasmids. These cells were individually plated, and regrown as single isolates in individual wells of 96-well plates. Ten microliters of each isolate was lysed, the inserts within the pACT2 and pASSPiI plasmids were amplified by polymerase chain reaction using primers specific for the flanking sequences of each vector, and approximately 200 amino-terminal bases of each insert was determined using an ABI 377 sequenator. Comparison to known sequences was made using the "Blast" program publicly available through the National Center for Biotechnology Information. Two of the inserts were identified as β-tubulin, the others identified as p62, hnRNP G, and the insert encoding 53BP2-IP1, 53BP2-IP2, or 53BP2-IP3. Specifically, the inserts contained nucleotides 830–1398 and 895–1398 of the coding sequence for β-tubulin as depicted in FIG. 2 (SEQ ID NO:3), nucleotides 929–1435 of the nucleotide sequence of p62 as depicted in FIG. 3 (SEQ ID NO:5), nucleotides 273–1322 of hnRNP G as depicted in FIG. 4 (SEQ ID NO:7), and the sequence depicted in FIG. 5 (encoding in part 53BP2-IP1, 53BP2-IP2, and 53BP2-IP3). The determined nucleic acid sequences and corresponding amino acid sequences of β-tubulin, p62, hnRNP G, and 53BP2-IP1, 53BP2-IP2, and 53BP2-IP3 are shown in FIGS. 2–4, and 9–13, respectively. A summary of the 53BP2 and 53BP2-IP interacting domains is shown in FIG. 6.

Verification of the Specificity of the 53BP2:Beta-tubulin, P62, hnRNP G, and 53BP2-IP1/2/3 Interactions To test for the specificity of bait:prey interaction, two general tests were first performed. In the first instance, N106$^r$ cells were created that express the individual plasmids encoding 53BP2, β-tubulin, p62, hnRNP G, and the sequences encoding 53BP2-IP1, 53BP2-IP2, and 53BP2-IP3. These yeast cells were plated on SCS plates, grown overnight, and examined for growth. No growth was found for all five proteins, confirming that they were not "self-activating" proteins, that is, these proteins require interaction with a second protein domain for a functional activation complex.

In the second instance, plasmids containing β-tubulin, p62, hnRNP G, and 53BP2-IP1, 53BP2-IP2, or 53BP2-IP3 inserts were transformed into strain YULH (mating type alpha and mated with yeast strain N106$^r$ (mating type a) expressing proteins other than 53BP2. Promiscuous binders, that is, inserts able to bind with many other proteins in a non-specific fashion, would interact non-specifically with non-53BP2 domains, and would be discarded as non-specific interactants. 53BP2 failed to interact with pRb (GenBank Acc. No. M28419, Lee et al., 1987, Nature 329: 642–645), the trk oncogene (GenBank Acc. No. X03541, Martin-Zanca, et al., 1986, Nature 319: 743–748), EST M62042 (Adams et al., 1991, Science 252: 1651–1656), Ral GDS (GenBank Acc. No. U14417, Hofer, et al., 1994, Proc. Natl. Acad. Sci. U.S.A. 91: 11089–11093) or E2F (GenBank Acc. No. X86096, direct submission). β-tubulin, p62, hnRNP G, and the sequences encoding 53BP2-IP1, 53BP2-IP2, or 53BP2-IP3 did not interact with MDM2 (GenBank Acc. No. M92424, Oliner et al., 1994, direct submission), CAS (GenBank Acc. No. U33286, Brinkmann et al., 1995, Proc. Natl. Acad. Sci. U.S.A. 92: 10427–10431), and PA9 (GenBank Acc. No. S82076, Yang et al., 1996, Carcinogenesis 17:563–567) Specifically, lack of growth for p62 and β-tubulin interactions with MDM2 is depicted in FIG. 7.

To recapitulate the detected interactions, and further demonstrate their specificity, the isolated bait plasmid for 53BP2, along with bait plasmids for MDM2 and human bait protein 1 (B1) were used to transform yeast strain N106$^r$ (mating type a). The interacting domains from p62 and β-tubulin were transformed into strain YULH (mating type alpha). The transformants were reamplified, and a mating performed to recapitulate the identified 53BP2:53BP2-IP interactions. 53BP2 complexed specifically with β-tubulin and p62, but not with two human proteins, H1 and H2. As illustrated in FIG. 7, the intersection of the 53BP2 row (bottom) with the β-tubulin and p62 columns indicates growth (i.e. a positive interaction), but the intersection of the 53BP2 row with the columns for H1 and H2 indicates no growth, i.e., no protein interaction. The known interaction between 53BP2 and PP1-alpha (Helps et al., 1995, FEBS Letts. 377: 295–300) was confirmed, as shown in FIG. 7, (intersection of column 3, row 3). As described above, β-tubulin and p62 failed to interact with MDM2 and B1. Mating of PP1-alpha and B1 confirmed an interaction previously found in our studies (FIG. 7; Nandabalan et al., 1997, unpublished).

Assembly of the Sequence Encoding 53BP2-IP1, 53BP2-IP2, and 53BP2-IP3

One identified prey sequence was identical to EST R72810 (GenBank data base "dbest"). The database contained other EST sequences that overlapped the EST R72810 sequence. Thus, it was possible to find contiguous sequences to extend the nucleotide sequence both 3' and 5' termini of the EST R72810. The general procedure utilized is illustrated in FIG. 8. The National Center for Biotechnology Information (N.C.B.I.) "Blast" Program was used to compare the EST R72810, and compared to all sequences in the non-redundant nucleotide data bases "NRDB," a compilation of GenBank+EMBL+DDBJ+PDB sequences (but no EST, STS, GSS, or HTGS sequences), as defined in the NCBI Blast program, "month," which includes all new or revised GenBank+EMBL+DDBJ+PDB sequences released in the last 30 days, and "dbest," a non-redundant database of GenBank+EMBL+DDBJ EST divisions. Sequences that aligned with 95% or greater identity at the nucleic acid level over their termini of at least 30 bases were utilized if the alignment resulted in 5' extension or 3' extension of the EST R72810 sequence. Once this first assembly was complete, the extended sequence was again subject to the Blast comparison to detect new homologies to the added extensions. The sequence was extended in both directions until new related sequences that allowed extension of the assembled sequence were no longer detected.

The extended EST R72810 sequence is illustrated in FIG. 9. The nucleic acid sequence of the original EST R72810 sequence is shown in bold lettering. For 5' extension, a long overlap was found with EST C17385, the nucleotide sequence of which is denoted by bold underline (Fujiwara et al., GenBank direct submission, Sep. 9, 1996). For 3' extension, overlap with EST AA464793 (Hillier et al., 1997, WashU-Merck EST Project), shown in boxed lettering, was detected. Additional overlap between EST AA464793 and EST AA479761 (Hillier et al., 1997, WashU-NCI Human EST Project), shown in bold, italic lettering, was used for further 3' extension, to complete the EST assembly process. The complete assembled sequence of 915 bases is shown in FIG. 9.

The assembled EST sequence was subjected to a further searches of the NRDB and "month" nucleic acid data bases to detect homologies to known protein sequences that were not detected over the shorter span of the original EST sequence. This was necessary where significant homology was not detected during the EST assembly process to proteins in the NRDB and "month" data bases, as was the case with the assembled EST R72810. No significant homologies to known proteins were detected for the extended EST R72810 utilizing this analysis.

Further, the sequence was analyzed by the NCBI program "ORF Finder" that performed translations in all three forward reading frames of the assembled DNA sequence (FIGS. 10A–F). EST R72810 (Hillier et al., 1995, GenBank Direct Submission Jun. 2, 1995) was obtained from the directionally-cloned Soares breast library 2NbHBst, and thus the direction of translation of the extended EST is known as 5' to 3'. Within the three translations, three possible open reading frames ("ORFs") were identified. Open reading frames greater than 60 amino acids following an initiator codon or an ORF with no initiator methionine encoded at the 5' end were determined to be possible protein products, and were submitted for Blast searching against the protein data base NRDB, a non-redundant compilation of GenBank CDS translations+PDB+SwissProt+PIR SwissProt sequences, and "month," which includes all new or revised GenBank CDS translation+PDB+SwissProt+PIR sequences released in the last 30 days.

Three possible protein candidates were identified by the hypothetical translation. The first candidate, encoded in Translation Frame #3 (FIG. 10F), encompasses an open reading frame from amino acid 1 (arg) to amino acid 286 (gln) that precedes an opal translational stop codon. This translational frame has no initiator methionine codon (ATG) and so must extend further 5' than the assembled sequence. The second protein candidate, encoded in Translation Frame #2 (FIG. 10D), extends from the initiator codon ATG in position 147 (met) to a gln residue, 69 amino acids downstream, that precedes an amber translational stop codon. The third protein candidate, encoded in Translation Frame #1 (FIG. 10B), extends from a glycine residue at position 1 (no initiation methionine codon was found in this reading frame) to a glycine at position 33, that precedes a TAA stop codon. None of these proteins displayed significant homology to any known protein at the nucleic acid or amino acid levels.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

SEQUENCE LISTING

<160> NUMBER OF SEQ ID NOS: 15

<210> SEQ ID NO 1
<211> LENGTH: 4534
<212> TYPE: DNA
<213> ORGANISM: Homo sapiens
<220> FEATURE:
<221> NAME/KEY: CDS
<222> LOCATION: (757)..(3771)

<400> SEQUENCE: 1

| | |
|---|---|
| gtcacgagcg tcgaagagac aaagccgcgt caggggggccc ggccggggcg ggggagcccg | 60 |
| gggcttgttg gtgccccagc ccgcgcggag ggcccttcgg acccgcgcgc cgccgctgcc | 120 |
| gccgccgccg cctcgcaaca ggtccgggcg gcctcgctct ccgctcccct ccccgcatc | 180 |
| cgcgaccctc cggggcacct cagctcggcc ggggccgcag tctggccacc cgcttccatg | 240 |
| cggttcgggt ccaagatgat gccgatgttt cttaccgtgt atctcagtaa caatgagcag | 300 |
| cacttcacag aagttccagt tactccagaa acaatatgca gagacgtggt ggatctgtgc | 360 |
| aaagaacccg gcgagagtga ttgccatttg gctgaagtgt ggtgtggctc tgtagagata | 420 |
| gagtttcatc atgttggcca ggatggtctc gatctcctga ccttgtgatc cgcctgcctc | 480 |
| ggcctcccaa agtgctggat tacaggtgtg agccaccacg atcagcctct agtgtttaaa | 540 |
| aaagaacgtc cagttgcgga taatgagcga atgtttgatg ttcttcaacg atttggaagt | 600 |
| cagaggaacg aagttcgctt cttccttcgt catgaacgcc ccctggcag ggacattgtg | 660 |
| agtggaccaa gatctcagga tccaagttta aaagaaatg gtgtaaaagt tcctggtgaa | 720 |
| tatcgaagaa aggagaacgg tgttaatagt cctagg atg gat ctg act ctt gct | 774 |
|                                                                        Met Asp Leu Thr Leu Ala<br>                                                                        1            5 | |
| gaa ctt cag gaa atg gca tct cgc cag cag caa cag att gaa gcc cag<br>Glu Leu Gln Glu Met Ala Ser Arg Gln Gln Gln Gln Ile Glu Ala Gln<br>          10                      15                      20 | 822 |
| caa caa ttg ctg gca act aag gaa cag cgc tta aag ttt ttg aaa caa<br>Gln Gln Leu Leu Ala Thr Lys Glu Gln Arg Leu Lys Phe Leu Lys Gln<br>       25                      30                      35 | 870 |
| caa gat cag cga caa cag caa caa gtt gct gag cag gag aaa ctt aaa<br>Gln Asp Gln Arg Gln Gln Gln Gln Val Ala Glu Gln Glu Lys Leu Lys<br> 40                      45                      50 | 918 |
| agg cta aaa gaa ata gct gag aat cag gaa gct aag cta aaa aaa gtg<br>Arg Leu Lys Glu Ile Ala Glu Asn Gln Glu Ala Lys Leu Lys Lys Val<br>55                    60                      65                      70 | 966 |
| aga gca ctt aaa ggc cac gtg gaa cag aag aga cta agc aat ggg aaa<br>Arg Ala Leu Lys Gly His Val Glu Gln Lys Arg Leu Ser Asn Gly Lys<br>                75                      80                      85 | 1014 |
| ctt gtg gag gaa att gaa cag atg aat aat ttg ttc cag caa aaa cag<br>Leu Val Glu Glu Ile Glu Gln Met Asn Asn Leu Phe Gln Gln Lys Gln<br>          90                      95                     100 | 1062 |
| agg gag ctc gtc ctg gct gtg tca aaa gta gaa gaa ctg acc agg cag<br>Arg Glu Leu Val Leu Ala Val Ser Lys Val Glu Glu Leu Thr Arg Gln<br>      105                   110                    115 | 1110 |
| cta gag atg ctc aag aac ggc agg atc gac agc cac cat gac aat cag<br>Leu Glu Met Leu Lys Asn Gly Arg Ile Asp Ser His His Asp Asn Gln<br> 120                      125                     130 | 1158 |
| tct gca gtg gct gag ctt gat cgc ctc tat aag gag ctg cag cta aga<br>Ser Ala Val Ala Glu Leu Asp Arg Leu Tyr Lys Glu Leu Gln Leu Arg<br>135                   140                      145                      150 | 1206 |

```
aac aaa ttg aat caa gag cag aat gcc aag cta caa caa cag agg gag    1254
Asn Lys Leu Asn Gln Glu Gln Asn Ala Lys Leu Gln Gln Gln Arg Glu
            155                 160                 165 tgt ttg aat aag cgt aat tca gaa gtg gca gtc atg gat aag cgt gtt    1302
Cys Leu Asn Lys Arg Asn Ser Glu Val Ala Val Met Asp Lys Arg Val
        170                 175                 180 aat gag ctg agg gac cgg ctg tgg aag aag aag gca gct cta cag caa    1350
Asn Glu Leu Arg Asp Arg Leu Trp Lys Lys Lys Ala Ala Leu Gln Gln
    185                 190                 195 aaa gaa aat cta cca gtt tca tct gat gga aat ctt ccc cag caa gcc    1398
Lys Glu Asn Leu Pro Val Ser Ser Asp Gly Asn Leu Pro Gln Gln Ala
200                 205                 210 gcg tca gcc cca agc cgt gtg gct gca gta ggt ccc tat atc cag tca    1446
Ala Ser Ala Pro Ser Arg Val Ala Ala Val Gly Pro Tyr Ile Gln Ser
215                 220                 225                 230 tct act atg cct cgg atg ccc tca agg cct gaa ttg ctg gtg aag cca    1494
Ser Thr Met Pro Arg Met Pro Ser Arg Pro Glu Leu Leu Val Lys Pro
                235                 240                 245 gcc ctg ccg gat ggt tcc ttg gtc att cag gct tca gag ggg ccg atg    1542
Ala Leu Pro Asp Gly Ser Leu Val Ile Gln Ala Ser Glu Gly Pro Met
            250                 255                 260 aaa ata cag aca ctg ccc aac atg aga tct ggg gct gct tca caa act    1590
Lys Ile Gln Thr Leu Pro Asn Met Arg Ser Gly Ala Ala Ser Gln Thr
        265                 270                 275 aaa ggc tct aaa atc cat cca gtt ggc cct gat tgg agt cct tca aat    1638
Lys Gly Ser Lys Ile His Pro Val Gly Pro Asp Trp Ser Pro Ser Asn
    280                 285                 290 gca gat ctt ttc cca agc caa ggc tct gct tct gta cct caa agc act    1686
Ala Asp Leu Phe Pro Ser Gln Gly Ser Ala Ser Val Pro Gln Ser Thr
295                 300                 305                 310 ggg aat gct ctg gat caa gtt gat gat gga gag gtt ccg ctg agg gag    1734
Gly Asn Ala Leu Asp Gln Val Asp Asp Gly Glu Val Pro Leu Arg Glu
                315                 320                 325 aaa gag aag aaa gtg cgt ccg ttc tca atg ttt gat gca gta gac cag    1782
Lys Glu Lys Lys Val Arg Pro Phe Ser Met Phe Asp Ala Val Asp Gln
            330                 335                 340 tcc aat gcc cca cct tcc ttt ggt act ctg agg aag aac cag agc agt    1830
Ser Asn Ala Pro Pro Ser Phe Gly Thr Leu Arg Lys Asn Gln Ser Ser
        345                 350                 355 gaa gat atc ttg cgg gat gct cag gtt gca aat aaa aat gtg gct aaa    1878
Glu Asp Ile Leu Arg Asp Ala Gln Val Ala Asn Lys Asn Val Ala Lys
    360                 365                 370 gta cca cct cct gtt cct aca aaa cca aaa cag att aat ttg cct tat    1926
Val Pro Pro Pro Val Pro Thr Lys Pro Lys Gln Ile Asn Leu Pro Tyr
375                 380                 385                 390 ttt gga caa act aat cag cca cct tca gac att aag cca gac gga agt    1974
Phe Gly Gln Thr Asn Gln Pro Pro Ser Asp Ile Lys Pro Asp Gly Ser
                395                 400                 405 tct cag cag ttg tca aca gtt gtt ccg tcc atg gga act aaa cca aaa    2022
Ser Gln Gln Leu Ser Thr Val Val Pro Ser Met Gly Thr Lys Pro Lys
            410                 415                 420 cca gca ggg cag cag ccg aga gtg ctg cta tct ccc agc ata cct tcg    2070
Pro Ala Gly Gln Gln Pro Arg Val Leu Leu Ser Pro Ser Ile Pro Ser
        425                 430                 435 gtt ggc caa gac cag acc ctt tct cca ggt tct aag caa gaa agt cca    2118
Val Gly Gln Asp Gln Thr Leu Ser Pro Gly Ser Lys Gln Glu Ser Pro
    440                 445                 450 cct gct gct gcc gtc cgg ccc ttt act ccc cag cct tcc aaa gac acc    2166
Pro Ala Ala Ala Val Arg Pro Phe Thr Pro Gln Pro Ser Lys Asp Thr
455                 460                 465                 470
```

```
tta ctt cca ccc ttc aga aaa ccc cag acc gtg gca gca agt tca ata    2214
Leu Leu Pro Pro Phe Arg Lys Pro Gln Thr Val Ala Ala Ser Ser Ile
            475                 480                 485 tat tcc atg tat acg caa cag cag gcg cca gga aaa aac ttc cag cag    2262
Tyr Ser Met Tyr Thr Gln Gln Gln Ala Pro Gly Lys Asn Phe Gln Gln
            490                 495                 500 gct gtg cag agc gcg ttg acc aag act cat acc aga ggg cca cac ttt    2310
Ala Val Gln Ser Ala Leu Thr Lys Thr His Thr Arg Gly Pro His Phe
            505                 510                 515 tca agt gta tat ggt aag cct gta att gct gct gcc cag aat caa cag    2358
Ser Ser Val Tyr Gly Lys Pro Val Ile Ala Ala Ala Gln Asn Gln Gln
            520                 525                 530 cag cac cca gag aac att tat tcc aat agc cag ggc aag cct ggc agt    2406
Gln His Pro Glu Asn Ile Tyr Ser Asn Ser Gln Gly Lys Pro Gly Ser
535                 540                 545                 550 cca gaa cct gaa aca gag cct gtt tct tca gtt cag gag aac cat gaa    2454
Pro Glu Pro Glu Thr Glu Pro Val Ser Ser Val Gln Glu Asn His Glu
            555                 560                 565 aac gaa aga att cct cgg cca ctc agc cca act aaa tta ctg cct ttc    2502
Asn Glu Arg Ile Pro Arg Pro Leu Ser Pro Thr Lys Leu Leu Pro Phe
            570                 575                 580 tta tct aat cct tac cga aac cag agt gat gct gac cta gaa gcc tta    2550
Leu Ser Asn Pro Tyr Arg Asn Gln Ser Asp Ala Asp Leu Glu Ala Leu
            585                 590                 595 cga aag aaa ctg tct aac gca cca agg cct cta aag aaa cgt agt tct    2598
Arg Lys Lys Leu Ser Asn Ala Pro Arg Pro Leu Lys Lys Arg Ser Ser
            600                 605                 610 att aca gag cca gag ggt cct aat ggg cca aat att cag aag ctt tta    2646
Ile Thr Glu Pro Glu Gly Pro Asn Gly Pro Asn Ile Gln Lys Leu Leu
615                 620                 625                 630 tat cag agg acc acc ata gcg gcc atg gag acc atc tct gtc cca tca    2694
Tyr Gln Arg Thr Thr Ile Ala Ala Met Glu Thr Ile Ser Val Pro Ser
            635                 640                 645 tac cca tcc aag tca gct tct gtg act gcc agc tca gaa agc cca gta    2742
Tyr Pro Ser Lys Ser Ala Ser Val Thr Ala Ser Ser Glu Ser Pro Val
            650                 655                 660 gaa atc cag aat cca tat tta cat gtg gag ccc gaa aag gag gtg gtc    2790
Glu Ile Gln Asn Pro Tyr Leu His Val Glu Pro Glu Lys Glu Val Val
            665                 670                 675 tct ctg gtt cct gaa tca ttg tcc cca gag gat gtg ggg aat gcc agt    2838
Ser Leu Val Pro Glu Ser Leu Ser Pro Glu Asp Val Gly Asn Ala Ser
            680                 685                 690 aca gag aac agt gac atg cca gct cct tct cca ggc ttt gat tat gag    2886
Thr Glu Asn Ser Asp Met Pro Ala Pro Ser Pro Gly Leu Asp Tyr Glu
695                 700                 705                 710 cct gag gga gtc cca gac aac agc cca aat ctc cag aat aac cca gaa    2934
Pro Glu Gly Val Pro Asp Asn Ser Pro Asn Leu Gln Asn Asn Pro Glu
            715                 720                 725 gaa cca aat cca gag gct cca cat gtg ctt gat gtg tac ctg gag gag    2982
Glu Pro Asn Pro Glu Ala Pro His Val Leu Asp Val Tyr Leu Glu Glu
            730                 735                 740 tac cct cca tac cca ccc cca cca tac cca tct ggg gag cct gaa ggg    3030
Tyr Pro Pro Tyr Pro Pro Pro Pro Tyr Pro Ser Gly Glu Pro Glu Gly
            745                 750                 755 ccc gga gaa gac tcg gtg agc atg cgc ccg cct gaa atc acc ggg cag    3078
Pro Gly Glu Asp Ser Val Ser Met Arg Pro Pro Glu Ile Thr Gly Gln
            760                 765                 770 gtc tct ctg cct cct ggt aaa agg aca aac ttg cgt aaa act ggc tca    3126
Val Ser Leu Pro Pro Gly Lys Arg Thr Asn Leu Arg Lys Thr Gly Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 775 |     |     |     |     | 780 |     |     |     |     | 785 |     |     |     |      |
|     |     |     |     |     |     |     |     |     |     |     |     | 790 |     |     |     |      |
| gag | cgt | atc | gct | cat | gga | atg | agg | gtg | aaa | ttc | aac | ccc | ctt | gct | tta | 3174 |
| Glu | Arg | Ile | Ala | His | Gly | Met | Arg | Val | Lys | Phe | Asn | Pro | Leu | Ala | Leu |      |
|     |     |     |     |     | 795 |     |     |     |     | 800 |     |     |     |     | 805 |      |
| ctg | cta | gat | tcg | tct | ttg | gag | gga | gaa | ttt | gac | ctt | gta | cag | aga | att | 3222 |
| Leu | Leu | Asp | Ser | Ser | Leu | Glu | Gly | Glu | Phe | Asp | Leu | Val | Gln | Arg | Ile |      |
|     |     |     |     | 810 |     |     |     |     | 815 |     |     |     |     | 820 |     |      |
| att | tat | gag | gtt | gat | gac | cca | agc | ctg | ccc | aat | gat | gaa | ggc | atc | acg | 3270 |
| Ile | Tyr | Glu | Val | Asp | Asp | Pro | Ser | Leu | Pro | Asn | Asp | Glu | Gly | Ile | Thr |      |
|     |     |     | 825 |     |     |     |     | 830 |     |     |     |     | 835 |     |     |      |
| gct | ctt | cac | aat | gct | gtg | tgt | gca | ggc | cac | aca | gaa | atc | gtt | aag | ttc | 3318 |
| Ala | Leu | His | Asn | Ala | Val | Cys | Ala | Gly | His | Thr | Glu | Ile | Val | Lys | Phe |      |
|     |     | 840 |     |     |     |     | 845 |     |     |     |     | 850 |     |     |     |      |
| ctg | gta | cag | ttt | ggt | gta | aat | gta | aat | gct | gct | gat | agt | gat | gga | tgg | 3366 |
| Leu | Val | Gln | Phe | Gly | Val | Asn | Val | Asn | Ala | Ala | Asp | Ser | Asp | Gly | Trp |      |
| 855 |     |     |     |     | 860 |     |     |     |     | 865 |     |     |     |     | 870 |      |
| act | cca | tta | cat | tgt | gct | gcc | tca | tgt | aac | aac | gtc | caa | gtg | tgt | aag | 3414 |
| Thr | Pro | Leu | His | Cys | Ala | Ala | Ser | Cys | Asn | Asn | Val | Gln | Val | Cys | Lys |      |
|     |     |     |     | 875 |     |     |     |     | 880 |     |     |     |     | 885 |     |      |
| ttt | ttg | gtg | gag | tca | gga | gcc | gct | gtg | ttt | gcc | atg | acc | tac | agt | gac | 3462 |
| Phe | Leu | Val | Glu | Ser | Gly | Ala | Ala | Val | Phe | Ala | Met | Thr | Tyr | Ser | Asp |      |
|     |     |     | 890 |     |     |     |     | 895 |     |     |     |     | 900 |     |     |      |
| atg | cag | act | gct | gca | gat | aag | tgc | gag | gaa | atg | gag | gaa | ggc | tac | act | 3510 |
| Met | Gln | Thr | Ala | Ala | Asp | Lys | Cys | Glu | Glu | Met | Glu | Glu | Gly | Tyr | Thr |      |
|     |     | 905 |     |     |     |     | 910 |     |     |     |     | 915 |     |     |     |      |
| cag | tgc | tcc | caa | ttt | ctt | tat | gga | gtt | cag | gag | aag | atg | ggc | ata | atg | 3558 |
| Gln | Cys | Ser | Gln | Phe | Leu | Tyr | Gly | Val | Gln | Glu | Lys | Met | Gly | Ile | Met |      |
|     | 920 |     |     |     |     | 925 |     |     |     |     | 930 |     |     |     |     |      |
| aat | aaa | gga | gtc | att | tat | gcg | ctt | tgg | gat | tat | gaa | cct | cag | aat | gat | 3606 |
| Asn | Lys | Gly | Val | Ile | Tyr | Ala | Leu | Trp | Asp | Tyr | Glu | Pro | Gln | Asn | Asp |      |
| 935 |     |     |     |     | 940 |     |     |     |     | 945 |     |     |     |     | 950 |      |
| gat | gag | ctg | ccc | atg | aaa | gaa | gga | gac | tgc | atg | aca | atc | atc | cac | agg | 3654 |
| Asp | Glu | Leu | Pro | Met | Lys | Glu | Gly | Asp | Cys | Met | Thr | Ile | Ile | His | Arg |      |
|     |     |     |     | 955 |     |     |     |     | 960 |     |     |     |     | 965 |     |      |
| gaa | gac | gaa | gat | gaa | atc | gaa | tgg | tgg | tgg | gcg | cgc | ctt | aat | gat | aag | 3702 |
| Glu | Asp | Glu | Asp | Glu | Ile | Glu | Trp | Trp | Trp | Ala | Arg | Leu | Asn | Asp | Lys |      |
|     |     |     | 970 |     |     |     |     | 975 |     |     |     |     | 980 |     |     |      |
| gag | gga | tat | gtt | cca | cgt | aac | ttg | ctg | gga | ctg | tac | cca | aga | att | aaa | 3750 |
| Glu | Gly | Tyr | Val | Pro | Arg | Asn | Leu | Leu | Gly | Leu | Tyr | Pro | Arg | Ile | Lys |      |
|     |     | 985 |     |     |     |     | 990 |     |     |     |     | 995 |     |     |     |      |
| cca | aga | caa | agg | agc | ttg | gcc | tgaaacttcc acacagaatt ttagtcaatg           |     |     |     |     |     |     |     | 3801 |
| Pro | Arg | Gln | Arg | Ser | Leu | Ala |                                            |     |     |     |     |     |     |     |     |      |
|     | 1000|     |     |     |     | 1005|                                            |     |     |     |     |     |     |     |     |      |

```
aagaattaat ctctgttaag aagaagtaat acgattattt ttggcaaaaa tttcacaaga   3861 cttatttta  tgacaatgta gcttgaaagc gatgaagaat gtctctagaa gagaatgaag   3921
gattgaagaa ttcaccatta gaggacattt agcgtgatga aataaagcat ctacgtcagc   3981
aggccatact gtgttggggc aaaggtgtcc cgtgtagcac tcagataagt atacagcgac   4041
aatcctgttt tctacaagaa tcctgtctag taaataggat catttattgg gcagttggga   4101
aatcagctct ctgtcctgtt gagtgttttc agcagctgct cctaaaccag tcctcctgcc   4161
agaaaggacc agtgccgtca catcgctgtc tctgattgtc cccggcacca gcaggccttg   4221
gggctcactg aaggctcgaa ggcactgcac accttgtata ttgtcagtga agaacgttag   4281
ttggttgtca gtgaacaata actttattat atgagttttt gtagcatctt aagaattata   4341
catatgtttg aaatattgaa actaagctac agtaccagta attagatgta gaatcttgtt   4401
tgtaggctga atttttaatct gtatttattg tcttttgtat ctcagaaatt agaaacttgc   4461
```

-continued

```
tacagactta cccgtaatat ttgtcaagat catagctgac tttaaaaaca gttgtaataa    4521 acttttttgat gct                                                      4534
```

<210> SEQ ID NO 2
<211> LENGTH: 1005
<212> TYPE: PRT
<213> ORGANISM: Homo sapiens

<400> SEQUENCE: 2

```
Met Asp Leu Thr Leu Ala Glu Leu Gln Glu Met Ala Ser Arg Gln Gln
 1               5                  10                  15

Gln Gln Ile Glu Ala Gln Gln Gln Leu Leu Ala Thr Lys Glu Gln Arg
            20                  25                  30

Leu Lys Phe Leu Lys Gln Gln Asp Gln Arg Gln Gln Gln Gln Val Ala
        35                  40                  45

Glu Gln Glu Lys Leu Lys Arg Leu Lys Glu Ile Ala Glu Asn Gln Glu
    50                  55                  60

Ala Lys Leu Lys Lys Val Arg Ala Leu Lys Gly His Val Glu Gln Lys
65                  70                  75                  80

Arg Leu Ser Asn Gly Lys Leu Val Glu Ile Glu Gln Met Asn Asn
            85                  90                  95

Leu Phe Gln Gln Lys Gln Arg Glu Leu Val Leu Ala Val Ser Lys Val
           100                 105                 110

Glu Glu Leu Thr Arg Gln Leu Glu Met Leu Lys Asn Gly Arg Ile Asp
       115                 120                 125

Ser His His Asp Asn Gln Ser Ala Val Ala Glu Leu Asp Arg Leu Tyr
   130                 135                 140

Lys Glu Leu Gln Leu Arg Asn Lys Leu Asn Gln Glu Gln Asn Ala Lys
145                 150                 155                 160

Leu Gln Gln Gln Arg Glu Cys Leu Asn Lys Arg Asn Ser Glu Val Ala
               165                 170                 175

Val Met Asp Lys Arg Val Asn Glu Leu Arg Asp Arg Leu Trp Lys Lys
           180                 185                 190

Lys Ala Ala Leu Gln Gln Lys Glu Asn Leu Pro Val Ser Ser Asp Gly
       195                 200                 205

Asn Leu Pro Gln Gln Ala Ala Ser Ala Pro Ser Arg Val Ala Ala Val
   210                 215                 220

Gly Pro Tyr Ile Gln Ser Ser Thr Met Pro Arg Met Pro Ser Arg Pro
225                 230                 235                 240

Glu Leu Leu Val Lys Pro Ala Leu Pro Asp Gly Ser Leu Val Ile Gln
               245                 250                 255

Ala Ser Glu Gly Pro Met Lys Ile Gln Thr Leu Pro Asn Met Arg Ser
           260                 265                 270

Gly Ala Ala Ser Gln Thr Lys Gly Ser Lys Ile His Pro Val Gly Pro
       275                 280                 285

Asp Trp Ser Pro Ser Asn Ala Asp Leu Phe Pro Ser Gln Gly Ser Ala
   290                 295                 300

Ser Val Pro Gln Ser Thr Gly Asn Ala Leu Asp Gln Val Asp Gly
305                 310                 315                 320

Glu Val Pro Leu Arg Glu Lys Glu Lys Lys Val Arg Pro Phe Ser Met
               325                 330                 335

Phe Asp Ala Val Asp Gln Ser Asn Ala Pro Pro Ser Phe Gly Thr Leu
           340                 345                 350
```

-continued

```
Arg Lys Asn Gln Ser Ser Glu Asp Ile Leu Arg Asp Ala Gln Val Ala
        355                 360                 365

Asn Lys Asn Val Ala Lys Val Pro Pro Val Pro Thr Lys Pro Lys
370                 375                 380

Gln Ile Asn Leu Pro Tyr Phe Gly Gln Thr Asn Gln Pro Pro Ser Asp
385                 390                 395                 400

Ile Lys Pro Asp Gly Ser Ser Gln Leu Ser Thr Val Val Pro Ser
                405                 410                 415

Met Gly Thr Lys Pro Lys Pro Ala Gly Gln Gln Pro Arg Val Leu Leu
                420                 425                 430

Ser Pro Ser Ile Pro Ser Val Gly Gln Asp Gln Thr Leu Ser Pro Gly
                435                 440                 445

Ser Lys Gln Glu Ser Pro Pro Ala Ala Val Arg Pro Phe Thr Pro
    450                 455                 460

Gln Pro Ser Lys Asp Thr Leu Leu Pro Pro Phe Arg Lys Pro Gln Thr
465                 470                 475                 480

Val Ala Ala Ser Ser Ile Tyr Ser Met Tyr Thr Gln Gln Ala Pro
                485                 490                 495

Gly Lys Asn Phe Gln Gln Ala Val Gln Ser Ala Leu Thr Lys Thr His
                500                 505                 510

Thr Arg Gly Pro His Phe Ser Ser Val Tyr Gly Lys Pro Val Ile Ala
        515                 520                 525

Ala Ala Gln Asn Gln Gln His Pro Glu Asn Ile Tyr Ser Asn Ser
    530                 535                 540

Gln Gly Lys Pro Gly Ser Pro Glu Pro Glu Thr Glu Pro Val Ser Ser
545                 550                 555                 560

Val Gln Glu Asn His Glu Asn Glu Arg Ile Pro Arg Pro Leu Ser Pro
                565                 570                 575

Thr Lys Leu Leu Pro Phe Leu Ser Asn Pro Tyr Arg Asn Gln Ser Asp
                580                 585                 590

Ala Asp Leu Glu Ala Leu Arg Lys Lys Leu Ser Asn Ala Pro Arg Pro
        595                 600                 605

Leu Lys Lys Arg Ser Ser Ile Thr Glu Pro Glu Gly Pro Asn Gly Pro
    610                 615                 620

Asn Ile Gln Lys Leu Leu Tyr Gln Arg Thr Thr Ile Ala Ala Met Glu
625                 630                 635                 640

Thr Ile Ser Val Pro Ser Tyr Pro Ser Lys Ser Ala Ser Val Thr Ala
                645                 650                 655

Ser Ser Glu Ser Pro Val Glu Ile Gln Asn Pro Tyr Leu His Val Glu
                660                 665                 670

Pro Glu Lys Glu Val Val Ser Leu Val Pro Glu Ser Leu Ser Pro Glu
        675                 680                 685

Asp Val Gly Asn Ala Ser Thr Glu Asn Ser Asp Met Pro Ala Pro Ser
    690                 695                 700

Pro Gly Leu Asp Tyr Glu Pro Glu Gly Val Pro Asp Asn Ser Pro Asn
705                 710                 715                 720

Leu Gln Asn Asn Pro Glu Glu Pro Asn Pro Glu Ala Pro His Val Leu
                725                 730                 735

Asp Val Tyr Leu Glu Glu Tyr Pro Pro Tyr Pro Pro Pro Pro Tyr Pro
                740                 745                 750

Ser Gly Glu Pro Glu Gly Pro Gly Glu Asp Ser Val Ser Met Arg Pro
        755                 760                 765

Pro Glu Ile Thr Gly Gln Val Ser Leu Pro Pro Gly Lys Arg Thr Asn
```

```
                  770                 775                 780
Leu Arg Lys Thr Gly Ser Glu Arg Ile Ala His Gly Met Arg Val Lys
785                 790                 795                 800

Phe Asn Pro Leu Ala Leu Leu Leu Asp Ser Ser Leu Glu Gly Glu Phe
                805                 810                 815

Asp Leu Val Gln Arg Ile Ile Tyr Glu Val Asp Pro Ser Leu Pro
                820                 825                 830

Asn Asp Glu Gly Ile Thr Ala Leu His Asn Ala Val Cys Ala Gly His
                835                 840                 845

Thr Glu Ile Val Lys Phe Leu Val Gln Phe Gly Val Asn Val Asn Ala
                850                 855                 860

Ala Asp Ser Asp Gly Trp Thr Pro Leu His Cys Ala Ala Ser Cys Asn
865                 870                 875                 880

Asn Val Gln Val Cys Lys Phe Leu Val Glu Ser Gly Ala Ala Val Phe
                885                 890                 895

Ala Met Thr Tyr Ser Asp Met Gln Thr Ala Ala Asp Lys Cys Glu Glu
                900                 905                 910

Met Glu Glu Gly Tyr Thr Gln Cys Ser Gln Phe Leu Tyr Gly Val Gln
                915                 920                 925

Glu Lys Met Gly Ile Met Asn Lys Gly Val Ile Tyr Ala Leu Trp Asp
930                 935                 940

Tyr Glu Pro Gln Asn Asp Asp Glu Leu Pro Met Lys Glu Gly Asp Cys
945                 950                 955                 960

Met Thr Ile Ile His Arg Glu Asp Glu Asp Glu Ile Glu Trp Trp Trp
                965                 970                 975

Ala Arg Leu Asn Asp Lys Glu Gly Tyr Val Pro Arg Asn Leu Leu Gly
                980                 985                 990

Leu Tyr Pro Arg Ile Lys Pro Arg Gln Arg Ser Leu Ala
        995                 1000                1005

<210> SEQ ID NO 3
<211> LENGTH: 1594
<212> TYPE: DNA
<213> ORGANISM: Homo sapiens
<220> FEATURE:
<221> NAME/KEY: CDS
<222> LOCATION: (64)..(1398)

<400> SEQUENCE: 3
gcccgccggt ccacgccgcg caccgctccg agggccagcg ccacccgctc cgcagccggc    60 acc atg cgc gag atc gtg cac atc cag gcg ggc cag tgc ggc aac cag    108
    Met Arg Glu Ile Val His Ile Gln Ala Gly Gln Cys Gly Asn Gln
    1               5                  10                  15 atc ggc gcc aag ttt tgg gag gtc atc agc gat gag cat ggg atc gac    156
Ile Gly Ala Lys Phe Trp Glu Val Ile Ser Asp Glu His Gly Ile Asp
                20                  25                  30 ccc aca ggc agt tac cat gga gac agt gac ttg cag ctg gag aga atc    204
Pro Thr Gly Ser Tyr His Gly Asp Ser Asp Leu Gln Leu Glu Arg Ile
            35                  40                  45 aac gtg tac tac aat gag gct gct ggt aac aaa tat gta cct cgg gcc    252
Asn Val Tyr Tyr Asn Glu Ala Ala Gly Asn Lys Tyr Val Pro Arg Ala
        50                  55                  60 atc ctg gtg gat ctg gag cct ggc acc atg gac tct gtc agg tct gga    300
Ile Leu Val Asp Leu Glu Pro Gly Thr Met Asp Ser Val Arg Ser Gly
    65                  70                  75 ccc ttc ggc cag atc ttc aga cca gac aac ttc gtg ttc ggc cag agt    348
Pro Phe Gly Gln Ile Phe Arg Pro Asp Asn Phe Val Phe Gly Gln Ser
```

```
              80                  85                  90                  95
gga gcc ggg aat aac tgg gcc aag ggc cac tac aca gag gga gcc gag           396
Gly Ala Gly Asn Asn Trp Ala Lys Gly His Tyr Thr Glu Gly Ala Glu
                        100                 105                 110 ctg gtc gac tcg gtc ctg gat gtg gtg agg aag gag tca gag agc tgt           444
Leu Val Asp Ser Val Leu Asp Val Val Arg Lys Glu Ser Glu Ser Cys
                115                 120                 125 gac tgt ctc cag ggc ttc cag ctg acc cac tct ctg ggg ggc ggc acg           492
Asp Cys Leu Gln Gly Phe Gln Leu Thr His Ser Leu Gly Gly Gly Thr
        130                 135                 140 ggg tcc ggg atg ggc acc ctg ctc atc agc aag atc cgg gaa gag tac           540
Gly Ser Gly Met Gly Thr Leu Leu Ile Ser Lys Ile Arg Glu Glu Tyr
145                 150                 155 cca gac cgc atc atg aac acc ttc agc gtc atg ccc tca ccc aag gtg           588
Pro Asp Arg Ile Met Asn Thr Phe Ser Val Met Pro Ser Pro Lys Val
160                 165                 170                 175 tca gac acg gtg gtg gag ccc tac aac gcc acc ctc tcg gtc cac cag           636
Ser Asp Thr Val Val Glu Pro Tyr Asn Ala Thr Leu Ser Val His Gln
                180                 185                 190 ctg gtg gaa aac aca gat gaa acc tac tcc att gat aac gag gcc ctg           684
Leu Val Glu Asn Thr Asp Glu Thr Tyr Ser Ile Asp Asn Glu Ala Leu
                195                 200                 205 tat gac atc tgc ttc cgc acc ctg aag ctg acc acc ccc acc tac ggg           732
Tyr Asp Ile Cys Phe Arg Thr Leu Lys Leu Thr Thr Pro Thr Tyr Gly
        210                 215                 220 gac ctc aac cac ctg gtg tcg gcc acc atg agc ggg gtc acc acc tgc           780
Asp Leu Asn His Leu Val Ser Ala Thr Met Ser Gly Val Thr Thr Cys
    225                 230                 235 ctg cgc ttc ccg ggc cag ctg aac gca gac ctg cgc aag ctg gcg gtg           828
Leu Arg Phe Pro Gly Gln Leu Asn Ala Asp Leu Arg Lys Leu Ala Val
240                 245                 250                 255 aac atg gtg ccc ttc cct cgc ctg cac ttc ttc atg ccc ggc ttc gcg           876
Asn Met Val Pro Phe Pro Arg Leu His Phe Phe Met Pro Gly Phe Ala
                260                 265                 270 ccc ctg acc agc cgg ggc agc cag cag tac cgg gcg ctc acg gtg ccc           924
Pro Leu Thr Ser Arg Gly Ser Gln Gln Tyr Arg Ala Leu Thr Val Pro
                275                 280                 285 gag ctc acc cag cag atg ttc gac tcc aag aac atg atg gcc gcc tgc           972
Glu Leu Thr Gln Gln Met Phe Asp Ser Lys Asn Met Met Ala Ala Cys
        290                 295                 300 gac ccg cgc cac ggc cgc tac ctg acg gtg gct gcc atc ttc cgg ggc          1020
Asp Pro Arg His Gly Arg Tyr Leu Thr Val Ala Ala Ile Phe Arg Gly
    305                 310                 315 cgc atg tcc atg aag gag gtg gac gag cag atg ctc aac gtg cag aac          1068
Arg Met Ser Met Lys Glu Val Asp Glu Gln Met Leu Asn Val Gln Asn
320                 325                 330                 335 aag aac agc agc tac ttc gtg gag tgg atc ccc aac aac gtg aag acg          1116
Lys Asn Ser Ser Tyr Phe Val Glu Trp Ile Pro Asn Asn Val Lys Thr
                340                 345                 350 gcc gtg tgc gac atc ccg ccc cgc ggc ctg aag atg tcg gcc acc ttc          1164
Ala Val Cys Asp Ile Pro Pro Arg Gly Leu Lys Met Ser Ala Thr Phe
                355                 360                 365 atc ggc aac agc acg gcc atc cag gag ctg ttc aag cgc atc tcc gag          1212
Ile Gly Asn Ser Thr Ala Ile Gln Glu Leu Phe Lys Arg Ile Ser Glu
        370                 375                 380 cag ttc acg gcc atg ttc cgg cgc aag gcc ttc ctg cac tgg tac acg          1260
Gln Phe Thr Ala Met Phe Arg Arg Lys Ala Phe Leu His Trp Tyr Thr
385                 390                 395 ggc gag ggc atg gac gag atg gag ttc acc gag gcc gag agc aac atg          1308
```

```
                                                      -continued

Gly Glu Gly Met Asp Glu Met Glu Phe Thr Glu Ala Glu Ser Asn Met
400                 405                 410                 415 aac gac ctg gtg tcc gag tac cag cag tac cag gac gcc acg gcc gac      1356
Asn Asp Leu Val Ser Glu Tyr Gln Gln Tyr Gln Asp Ala Thr Ala Asp
                420                 425                 430 gaa caa ggg gag ttc gag gag gag gag ggc gag gac gag gct              1398
Glu Gln Gly Glu Phe Glu Glu Glu Glu Gly Glu Asp Glu Ala
            435                 440                 445 taaaaacttc tcagatcaat cgtgcatcct tagtgaactt ctgttgtcct caagcatggt    1458 cttttctactt gtaaactatg gtgctcagtt ttgcctctgt tagaaattca cactgttgat  1518
gtaatgatgt ggaactcctc taaaaattac agtattgtct gtgaaggtat ctatactaat   1578
aaaaaagcat gtgtag                                                   1594

<210> SEQ ID NO 4
<211> LENGTH: 445
<212> TYPE: PRT
<213> ORGANISM: Homo sapiens

<400> SEQUENCE: 4

Met Arg Glu Ile Val His Ile Gln Ala Gly Gln Cys Gly Asn Gln Ile
 1               5                  10                  15

Gly Ala Lys Phe Trp Glu Val Ile Ser Asp Glu His Gly Ile Asp Pro
             20                  25                  30

Thr Gly Ser Tyr His Gly Asp Ser Asp Leu Gln Leu Glu Arg Ile Asn
         35                  40                  45

Val Tyr Tyr Asn Glu Ala Ala Gly Asn Lys Tyr Val Pro Arg Ala Ile
     50                  55                  60

Leu Val Asp Leu Glu Pro Gly Thr Met Asp Ser Val Arg Ser Gly Pro
 65                  70                  75                  80

Phe Gly Gln Ile Phe Arg Pro Asp Asn Phe Val Phe Gly Gln Ser Gly
                 85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ser Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Ser Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
```

```
                    275                 280                 285
Leu Thr Gln Gln Met Phe Asp Ser Lys Asn Met Met Ala Ala Cys Asp
    290                 295                 300

Pro Arg His Gly Arg Tyr Leu Thr Val Ala Ala Ile Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
        355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Asp Glu
            420                 425                 430

Gln Gly Glu Phe Glu Glu Glu Gly Glu Asp Glu Ala
        435                 440                 445

<210> SEQ ID NO 5
<211> LENGTH: 2685
<212> TYPE: DNA
<213> ORGANISM: Homo sapiens
<220> FEATURE:
<221> NAME/KEY: CDS
<222> LOCATION: (107)..(1435)

<400> SEQUENCE: 5
ggcttcggtc gctaccgctc ccgctctgcc accccgcca accgccgctc gggcctccgt      60
cgctgccgcg tcgctttctc gctccttgga tcgcacatcc tcccag atg cag cgc      115
                                                   Met Gln Arg
                                                     1 cgg gac gac ccc gcc gcg cgc atg agc cgg tct tcg ggc cgt agc ggc      163
Arg Asp Asp Pro Ala Ala Arg Met Ser Arg Ser Ser Gly Arg Ser Gly
      5                  10                  15 tcc atg gac ccc tcc ggt gcc cac ccc tcg gtg cgt cag acg ccg tct      211
Ser Met Asp Pro Ser Gly Ala His Pro Ser Val Arg Gln Thr Pro Ser
 20                  25                  30                  35 cgg cag ccg ccg ctg cct cac cgg tcc cgg gga ggc gga ggg gga tcc      259
Arg Gln Pro Pro Leu Pro His Arg Ser Arg Gly Gly Gly Gly Gly Ser
              40                  45                  50 cgc ggg ggc gcc cgg gcc tcg ccc gcc acg cag ccg cca ccg ctg ctg      307
Arg Gly Gly Ala Arg Ala Ser Pro Ala Thr Gln Pro Pro Pro Leu Leu
         55                  60                  65 ccg ccc tcg gcc acg ggt ccc gac gcg aca gtg ggc ggg cca gcg ccg      355
Pro Pro Ser Ala Thr Gly Pro Asp Ala Thr Val Gly Gly Pro Ala Pro
     70                  75                  80 acc ccg ctg ctg ccc ccc tcg gcc aca gcc tcg gtc aag atg gag cca      403
Thr Pro Leu Leu Pro Pro Ser Ala Thr Ala Ser Val Lys Met Glu Pro
 85                  90                  95 gag aac aag tac ctg ccc gaa ctc atg gcc gag aag gac tcg ctc gac      451
Glu Asn Lys Tyr Leu Pro Glu Leu Met Ala Glu Lys Asp Ser Leu Asp
100                 105                 110                 115 ccg tcc ttc act cac gcc atg cag ctg ctg acg gca gaa att gag aag      499
Pro Ser Phe Thr His Ala Met Gln Leu Leu Thr Ala Glu Ile Glu Lys
```

-continued

```
                    120                 125                 130
att cag aaa gga gac tca aaa aag gat gat gag gag aat tac ttg gat         547
Ile Gln Lys Gly Asp Ser Lys Lys Asp Asp Glu Glu Asn Tyr Leu Asp
                    135                 140                 145 tta ttt tct cat aag aac atg aaa ctg aaa gag cga gtg ctg ata cct         595
Leu Phe Ser His Lys Asn Met Lys Leu Lys Glu Arg Val Leu Ile Pro
            150                 155                 160 gtc aag cag tat ccc aag ttc aat ttt gtg ggg aag att ctt gga cca         643
Val Lys Gln Tyr Pro Lys Phe Asn Phe Val Gly Lys Ile Leu Gly Pro
        165                 170                 175 caa ggg aat aca atc aaa aga ctg cag gaa gag act ggt gca aag atc         691
Gln Gly Asn Thr Ile Lys Arg Leu Gln Glu Glu Thr Gly Ala Lys Ile
180                 185                 190                 195 tct gta ttg gga aag ggc tca atg aga gac aaa gcc aag gag gaa gag         739
Ser Val Leu Gly Lys Gly Ser Met Arg Asp Lys Ala Lys Glu Glu Glu
                    200                 205                 210 ctg cgc aaa ggt gga gac ccc aaa tat gcc cac ttg aat atg gat ctg         787
Leu Arg Lys Gly Gly Asp Pro Lys Tyr Ala His Leu Asn Met Asp Leu
            215                 220                 225 cat gtc ttc att gaa gtc ttt gga ccc cca tgt gag gct tat gct ctt         835
His Val Phe Ile Glu Val Phe Gly Pro Pro Cys Glu Ala Tyr Ala Leu
        230                 235                 240 atg gcc cat gcc atg gag gaa gtc aag aaa ttt cta gta ccg gat atg         883
Met Ala His Ala Met Glu Glu Val Lys Lys Phe Leu Val Pro Asp Met
245                 250                 255 atg gat gat atc tgt cag gag caa ttt cta gag ctg tcc tac ttg aat         931
Met Asp Asp Ile Cys Gln Glu Gln Phe Leu Glu Leu Ser Tyr Leu Asn
260                 265                 270                 275 gga gta cct gaa ccc tct cgt gga cgt ggg gtg cca gtg aga ggc cgg         979
Gly Val Pro Glu Pro Ser Arg Gly Arg Gly Val Pro Val Arg Gly Arg
                    280                 285                 290 gga gct gca cct cct cca cca cct gtt ccc agg ggc cgt ggt gtt gga        1027
Gly Ala Ala Pro Pro Pro Pro Pro Val Pro Arg Gly Arg Gly Val Gly
            295                 300                 305 cca cct cgg ggg gct ttg gta cgt ggt aca cca gta agg gga gcc atc        1075
Pro Pro Arg Gly Ala Leu Val Arg Gly Thr Pro Val Arg Gly Ala Ile
        310                 315                 320 acc aga ggt gcc act gtg act cga ggc gtg cca ccc cca cct act gtg        1123
Thr Arg Gly Ala Thr Val Thr Arg Gly Val Pro Pro Pro Pro Thr Val
325                 330                 335 agg ggt gct cca gca cca aga gca cgg aca gcg ggc atc cag agg ata        1171
Arg Gly Ala Pro Ala Pro Arg Ala Arg Thr Ala Gly Ile Gln Arg Ile
340                 345                 350                 355 cct ttg cct cca cct cct gca cca gaa aca tat gaa gaa tat gga tat        1219
Pro Leu Pro Pro Pro Pro Ala Pro Glu Thr Tyr Glu Glu Tyr Gly Tyr
                    360                 365                 370 gat gat aca tac gca gaa caa agt tac gaa ggc tac gaa ggc tat tac        1267
Asp Asp Thr Tyr Ala Glu Gln Ser Tyr Glu Gly Tyr Glu Gly Tyr Tyr
            375                 380                 385 agc cag agt caa ggg gac tca gaa tat tat gac tat gga cat ggg gag        1315
Ser Gln Ser Gln Gly Asp Ser Glu Tyr Tyr Asp Tyr Gly His Gly Glu
        390                 395                 400 gtt caa gat tct tat gaa gct tat ggc cag gac gac tgg aat ggg acc        1363
Val Gln Asp Ser Tyr Glu Ala Tyr Gly Gln Asp Asp Trp Asn Gly Thr
405                 410                 415 agg ccg tcg ctg aag gcc cct cct gct agg cca gtg aag gga gca tac        1411
Arg Pro Ser Leu Lys Ala Pro Pro Ala Arg Pro Val Lys Gly Ala Tyr
420                 425                 430                 435 aga gag cac cca tat gga cgt tat taaaaacaaa catgagggga aaatatcagt      1465
Arg Glu His Pro Tyr Gly Arg Tyr
```

```
Arg Glu His Pro Tyr Gly Arg Tyr
            440 tatgagcaaa gttgttactg atttcttgta tctcccagga ttcctgttgc tttacccaca      1525 acagacaagt aattgtctaa gtgtttttct tcgtggtccc cttcttctcc ccaccttatt      1585 ccattcttaa ctctgcattc tggcttctgt atgtagtatt ttaaaatgag ttaaaataga      1645 tttaggaata ttgaattaat ttttttaagtg tgtagatgct ttttctttg ttgtttaaat      1705 ataaacagaa gtgtaccttt tataataaaa aaaagaagtt gagtaaaaaa aaaaaacaca      1765 caaacctgtt agtttcaaaa atgacattgc ttgcttaaag gttctgaagt aaaggcttgt      1825 taagtttctc ttagtttga tttgaggcat cccgtaaagt tgtagttgca gaatcccaaa       1885 ctaggctaca tttcaaaatt cagggctgtt taagatttaa aatcacaaac attaacggca      1945 gtaggcacca ccatgtaaaa gtgagctcag acgtctctaa aaaatgtttc ctttataaaa      2005 gcacatggcg gttgaatctt aaggttaaat tttaatatga aagatcctca tgaattaaat      2065 agttgatgca attttttaacg ttaattgata taaaaaaaaa aacaacaaaa ttaggcttgt     2125 aaaactgact ttttcattac gtgggttttg aaatctagcc ccagacatac tgtgttgaga      2185 gatacttaga gggagggagt aggttttgaa gaggttgatg gtggtgggga gggaaggcct      2245 cctgaattga gtttgatgca gagcttttta gccatgaaga atctttcagt catagtacta      2305 ataattaaat tttcagtatt taaaaagaca aagtattttg tccatttgag attctgcact      2365 ccatgaaaag ttcacttgga cgctggggcc aaaagctgtt gattttctta agttgacggt      2425 tgtcaatata tcgaactgtt cccaagttag tcaagtatgt ctcaacacta gcatgatata      2485 aaaagggaca ctgcagctga atgaaaaagg aatcaaaatc cactttgtac ataagttaaa      2545 gtcctaattg gatttgtacc gtcctcccat tttgttctcg gaagattaaa tgctacatgt      2605 gtaagtctgc ctaaataggt agcttaaact tatgtcaaaa tgtctgcagc agtttgtcaa      2665 taaagtttag tccttttta                                                  2685

<210> SEQ ID NO 6
<211> LENGTH: 443
<212> TYPE: PRT
<213> ORGANISM: Homo sapiens

<400> SEQUENCE: 6

Met Gln Arg Arg Asp Asp Pro Ala Ala Arg Met Ser Arg Ser Ser Gly
 1               5                  10                  15

Arg Ser Gly Ser Met Asp Pro Ser Gly Ala His Pro Ser Val Arg Gln
            20                  25                  30

Thr Pro Ser Arg Gln Pro Pro Leu Pro His Arg Ser Arg Gly Gly Gly
        35                  40                  45

Gly Gly Ser Arg Gly Gly Ala Arg Ala Ser Pro Ala Thr Gln Pro Pro
    50                  55                  60

Pro Leu Leu Pro Pro Ser Ala Thr Gly Pro Asp Ala Thr Val Gly Gly
65                  70                  75                  80

Pro Ala Pro Thr Pro Leu Leu Pro Pro Ser Ala Thr Ala Ser Val Lys
                85                  90                  95

Met Glu Pro Glu Asn Lys Tyr Leu Pro Glu Leu Met Ala Glu Lys Asp
            100                 105                 110

Ser Leu Asp Pro Ser Phe Thr His Ala Met Gln Leu Leu Thr Ala Glu
        115                 120                 125

Ile Glu Lys Ile Gln Lys Gly Asp Ser Lys Lys Asp Asp Glu Glu Asn
    130                 135                 140
```

-continued

```
Tyr Leu Asp Leu Phe Ser His Lys Asn Met Lys Leu Lys Glu Arg Val
145                 150                 155                 160

Leu Ile Pro Val Lys Gln Tyr Pro Lys Phe Asn Phe Val Gly Lys Ile
            165                 170                 175

Leu Gly Pro Gln Gly Asn Thr Ile Lys Arg Leu Gln Glu Thr Gly
            180                 185                 190

Ala Lys Ile Ser Val Leu Gly Lys Gly Ser Met Arg Asp Lys Ala Lys
            195                 200                 205

Glu Glu Glu Leu Arg Lys Gly Gly Asp Pro Lys Tyr Ala His Leu Asn
210                 215                 220

Met Asp Leu His Val Phe Ile Glu Val Phe Gly Pro Cys Glu Ala
225                 230                 235                 240

Tyr Ala Leu Met Ala His Ala Met Glu Glu Val Lys Lys Phe Leu Val
            245                 250                 255

Pro Asp Met Met Asp Asp Ile Cys Gln Glu Gln Phe Leu Glu Leu Ser
            260                 265                 270

Tyr Leu Asn Gly Val Pro Glu Pro Ser Arg Gly Arg Gly Val Pro Val
            275                 280                 285

Arg Gly Arg Gly Ala Ala Pro Pro Pro Pro Val Pro Arg Gly Arg
290                 295                 300

Gly Val Gly Pro Pro Arg Gly Ala Leu Val Arg Gly Thr Pro Val Arg
305                 310                 315                 320

Gly Ala Ile Thr Arg Gly Ala Thr Val Thr Arg Gly Val Pro Pro Pro
            325                 330                 335

Pro Thr Val Arg Gly Ala Pro Ala Pro Arg Ala Arg Thr Ala Gly Ile
            340                 345                 350

Gln Arg Ile Pro Leu Pro Pro Pro Ala Pro Glu Thr Tyr Glu Glu
            355                 360                 365

Tyr Gly Tyr Asp Asp Thr Tyr Ala Glu Gln Ser Tyr Glu Gly Tyr Glu
            370                 375                 380

Gly Tyr Tyr Ser Gln Ser Gln Gly Asp Ser Glu Tyr Tyr Asp Tyr Gly
385                 390                 395                 400

His Gly Glu Val Gln Asp Ser Tyr Glu Ala Tyr Gly Gln Asp Asp Trp
            405                 410                 415

Asn Gly Thr Arg Pro Ser Leu Lys Ala Pro Ala Arg Pro Val Lys
            420                 425                 430

Gly Ala Tyr Arg Glu His Pro Tyr Gly Arg Tyr
            435                 440

<210> SEQ ID NO 7
<211> LENGTH: 1894
<212> TYPE: DNA
<213> ORGANISM: Homo sapiens
<220> FEATURE:
<221> NAME/KEY: CDS
<222> LOCATION: (12)..(1322)

<400> SEQUENCE: 7
cggaaaaaaa a atg gtt gaa gca gat cgc cca gga aag ctc ttc att ggt      50
            Met Val Glu Ala Asp Arg Pro Gly Lys Leu Phe Ile Gly
            1               5                   10 ggg ctt aat acg gaa aca aat gag aaa gct ctt gaa gca gta ttt ggc      98
Gly Leu Asn Thr Glu Thr Asn Glu Lys Ala Leu Glu Ala Val Phe Gly
    15                  20                  25 aaa tat gga cga ata gtg gaa gta ctc ttg atg aaa gac cgt gaa acc     146
Lys Tyr Gly Arg Ile Val Glu Val Leu Leu Met Lys Asp Arg Glu Thr
```

```
              30                  35                  40                  45 aac aaa tca aga gga ttt gct ttt gtc acc ttt gaa agc cca gca gac    194
Asn Lys Ser Arg Gly Phe Ala Phe Val Thr Phe Glu Ser Pro Ala Asp
                50                  55                  60 gct aag gat gca gcc aga gac atg aat gga aag tca tta gat gga aaa    242
Ala Lys Asp Ala Ala Arg Asp Met Asn Gly Lys Ser Leu Asp Gly Lys
                65                  70                  75 gcc atc aag gtg gaa caa gcc acc aaa cca tca ttt gaa agt ggt aga    290
Ala Ile Lys Val Glu Gln Ala Thr Lys Pro Ser Phe Glu Ser Gly Arg
        80                  85                  90 cgt gga ccg cct cca cct cca aga agt aga ggc cct cca aga ggt ctt    338
Arg Gly Pro Pro Pro Pro Pro Arg Ser Arg Gly Pro Pro Arg Gly Leu
        95                  100                 105 aga ggt gga aga gga gga agt gga gga acc agg gga cct ccc tca cgg    386
Arg Gly Gly Arg Gly Gly Ser Gly Gly Thr Arg Gly Pro Pro Ser Arg
110                 115                 120                 125 gga gga cac atg gat gac ggt gga tat tcc atg aat ttt aac atg agt    434
Gly Gly His Met Asp Asp Gly Gly Tyr Ser Met Asn Phe Asn Met Ser
                130                 135                 140 tct tcc agg gga cca ctc cca gta aaa aga gga cca cca cca aga agt    482
Ser Ser Arg Gly Pro Leu Pro Val Lys Arg Gly Pro Pro Pro Arg Ser
                145                 150                 155 ggg ggt cct cct cct aag aga tct gca cct tca gga cca gtt cgc agt    530
Gly Gly Pro Pro Pro Lys Arg Ser Ala Pro Ser Gly Pro Val Arg Ser
                160                 165                 170 agc agt gga atg gga gga aga gct cct gta tca cgt gga aga gat agt    578
Ser Ser Gly Met Gly Gly Arg Ala Pro Val Ser Arg Gly Arg Asp Ser
        175                 180                 185 tat gga ggt cca cct cga agg gaa ccg ctg ccc tct cgt aga gat gtt    626
Tyr Gly Gly Pro Pro Arg Arg Glu Pro Leu Pro Ser Arg Arg Asp Val
190                 195                 200                 205 tat ttg tct cca aga gat gat ggg tat tct act aaa gac agc tat tca    674
Tyr Leu Ser Pro Arg Asp Asp Gly Tyr Ser Thr Lys Asp Ser Tyr Ser
                210                 215                 220 agc aga gat tac cca agt tct cgt gat act aga gat tat gca cca cca    722
Ser Arg Asp Tyr Pro Ser Ser Arg Asp Thr Arg Asp Tyr Ala Pro Pro
                225                 230                 235 cca cga gat tat act tac cgt gat tat ggt cat tcc agt tca cgt gat    770
Pro Arg Asp Tyr Thr Tyr Arg Asp Tyr Gly His Ser Ser Ser Arg Asp
                240                 245                 250 gac tat cca tca aga gaa tat agc gat aga gat gga tat ggt cgt gat    818
Asp Tyr Pro Ser Arg Glu Tyr Ser Asp Arg Asp Gly Tyr Gly Arg Asp
        255                 260                 265 cgt gac tat tca gat cat cca agt gga ggt tcc tac aga gat tca tat    866
Arg Asp Tyr Ser Asp His Pro Ser Gly Gly Ser Tyr Arg Asp Ser Tyr
270                 275                 280                 285 gag agt tat ggt aac tca cgt agt gct cca cct aca cga ggg ccc ccg    914
Glu Ser Tyr Gly Asn Ser Arg Ser Ala Pro Pro Thr Arg Gly Pro Pro
                290                 295                 300 cca tct tat ggt gga agc agt cgc tat gat gat tac agc agc tca cgt    962
Pro Ser Tyr Gly Gly Ser Ser Arg Tyr Asp Asp Tyr Ser Ser Ser Arg
        305                 310                 315 gac gga tat ggt gga agt cga gac agt tac tca agc agc cga agt gat   1010
Asp Gly Tyr Gly Gly Ser Arg Asp Ser Tyr Ser Ser Ser Arg Ser Asp
        320                 325                 330 ctc tac tca agt ggt cgt gat cgg gtt ggc aga caa gaa aga ggg ctt   1058
Leu Tyr Ser Ser Gly Arg Asp Arg Val Gly Arg Gln Glu Arg Gly Leu
        335                 340                 345 ccc cct tct atg gaa agg ggg tac ctc ctc cac gtg att cct aca gca   1106
```

```
Pro Pro Ser Met Glu Arg Gly Tyr Leu Leu His Val Ile Pro Thr Ala
350                 355                 360                 365 gtt caa gcc gcg gac gac caa gag gtg gtg gcc gtg gag gaa gcc gat    1154
Val Gln Ala Ala Asp Asp Gln Glu Val Val Ala Val Glu Glu Ala Asp
                370                 375                 380 ctg ata gag ggg gag gca gaa gca gat act aga aac aaa caa aac ttt    1202
Leu Ile Glu Gly Glu Ala Glu Ala Asp Thr Arg Asn Lys Gln Asn Phe
            385                 390                 395 gga cca aaa tcc cag ttc aaa gaa aca aaa agt gga aac tat tct atc    1250
Gly Pro Lys Ser Gln Phe Lys Glu Thr Lys Ser Gly Asn Tyr Ser Ile
        400                 405                 410 ata act acc caa gga cta cta aaa gga aaa att gtg tta ctt ttt tta    1298
Ile Thr Thr Gln Gly Leu Leu Lys Gly Lys Ile Val Leu Leu Phe Leu
    415                 420                 425 aat tcc ctg tta agt tcc cct cca taatttttat gttcttgtga ggaaaaaagt   1352
Asn Ser Leu Leu Ser Ser Pro Pro
430                 435 aaaacatgtt taattttatt tgacttctgc attgcttttc aacaagcaaa tgttaaatgt   1412
gttaagactt gtactagtgt tgtaactttc caagtaaaag tatcccctaa aggccacttc   1472
ctatctgatt tttcccagca aatgaggcag gcaattctag tcttccacaa aacatctagc   1532
catctaaaat ggagagatga atcattctac ctatacaaac aagctagcta ttagagggtg   1592
gttggggtat gctactcata agatttcagg gtgtcttcca actgaaatct caatgttctc   1652
agtacgaaaa acctgaaatc acatgcctat gtaaggaaag tgctattcac ccagtaaacc   1712
caaaaaagca aatggataat gctggccatt ttgcctttct gacatttcct tgggaatctg   1772
caagaacctc ccctttccct tcccccaata agaccattta agtgtgtgtt aaacaactac   1832
agaatactaa gtaaaaagtt tggccaaaac caaaaaaaaa aaaaaaaaaa aaaaaaaaa    1892 aa    1894

<210> SEQ ID NO 8
<211> LENGTH: 437
<212> TYPE: PRT
<213> ORGANISM: Homo sapiens

<400> SEQUENCE: 8

Met Val Glu Ala Asp Arg Pro Gly Lys Leu Phe Ile Gly Gly Leu Asn
 1               5                  10                  15

Thr Glu Thr Asn Glu Lys Ala Leu Glu Ala Val Phe Gly Lys Tyr Gly
                20                  25                  30

Arg Ile Val Glu Val Leu Leu Met Lys Asp Arg Glu Thr Asn Lys Ser
            35                  40                  45

Arg Gly Phe Ala Phe Val Thr Phe Glu Ser Pro Ala Asp Ala Lys Asp
        50                  55                  60

Ala Ala Arg Asp Met Asn Gly Lys Ser Leu Asp Gly Lys Ala Ile Lys
65                  70                  75                  80

Val Glu Gln Ala Thr Lys Pro Ser Phe Glu Ser Gly Arg Arg Gly Pro
                85                  90                  95

Pro Pro Pro Pro Arg Ser Arg Gly Pro Pro Arg Gly Leu Arg Gly Gly
                100                 105                 110

Arg Gly Gly Ser Gly Gly Thr Arg Gly Pro Pro Ser Arg Gly Gly His
            115                 120                 125

Met Asp Asp Gly Gly Tyr Ser Met Asn Phe Asn Met Ser Ser Ser Arg
        130                 135                 140

Gly Pro Leu Pro Val Lys Arg Gly Pro Pro Pro Arg Ser Gly Gly Pro
```

|       |       |       |       | 145   |       |       |       |       | 150   |       |       |       |       | 155   |       |       |       |       | 160   |
|-------|-------|-------|-------|-------|-------|-------|-------|-------|-------|-------|-------|-------|-------|-------|-------|-------|-------|-------|-------|

Pro Pro Lys Arg Ser Ala Pro Ser Gly Pro Val Arg Ser Ser Ser Gly
                165                      170                    175

Met Gly Gly Arg Ala Pro Val Ser Arg Gly Arg Asp Ser Tyr Gly Gly
                180                      185                    190

Pro Pro Arg Arg Glu Pro Leu Pro Ser Arg Arg Asp Val Tyr Leu Ser
                195                      200                    205

Pro Arg Asp Asp Gly Tyr Ser Thr Lys Asp Ser Tyr Ser Ser Arg Asp
    210                      215                    220

Tyr Pro Ser Ser Arg Asp Thr Arg Asp Tyr Ala Pro Pro Arg Asp
225                  230                    235              240

Tyr Thr Tyr Arg Asp Tyr Gly His Ser Ser Arg Asp Asp Tyr Pro
                245                      250                    255

Ser Arg Glu Tyr Ser Asp Arg Asp Gly Tyr Gly Arg Asp Arg Asp Tyr
                260                      265                    270

Ser Asp His Pro Ser Gly Gly Ser Tyr Arg Asp Ser Tyr Glu Ser Tyr
        275                      280                    285

Gly Asn Ser Arg Ser Ala Pro Pro Thr Arg Gly Pro Pro Ser Tyr
    290                      295                    300

Gly Gly Ser Ser Arg Tyr Asp Asp Tyr Ser Ser Arg Asp Gly Tyr
305                  310                    315              320

Gly Gly Ser Arg Asp Ser Tyr Ser Ser Arg Ser Asp Leu Tyr Ser
                325                      330                    335

Ser Gly Arg Asp Arg Val Gly Arg Gln Glu Arg Gly Leu Pro Pro Ser
                340                      345                    350

Met Glu Arg Gly Tyr Leu Leu His Val Ile Pro Thr Ala Val Gln Ala
        355                      360                    365

Ala Asp Asp Gln Glu Val Val Ala Val Glu Glu Ala Asp Leu Ile Glu
    370                      375                    380

Gly Glu Ala Glu Ala Asp Thr Arg Asn Lys Gln Asn Phe Gly Pro Lys
385                  390                    395              400

Ser Gln Phe Lys Glu Thr Lys Ser Gly Asn Tyr Ser Ile Ile Thr Thr
                405                      410                    415

Gln Gly Leu Leu Lys Gly Lys Ile Val Leu Leu Phe Leu Asn Ser Leu
                420                      425                    430

Leu Ser Ser Pro Pro
        435

<210> SEQ ID NO 9
<211> LENGTH: 323
<212> TYPE: DNA
<213> ORGANISM: Homo sapiens

<400> SEQUENCE: 9

```
gctatagcag aaccgctggg gtaacaacaa ccgggataac aacaactcca acaacagagg      60
cagctacaac cgggctcccc agcaacagcc gccaccacag cagcctccgc caccacagcc     120
accacccag cagccaccgc caccacccag ctacagccct gctcggaacc ccccaggggc     180
cagcacctac aataagaaca gcaacatccc tggctcaagc gccaatacca gcaccccac     240
cgtcagcagc tacagcccttc cacagccga gttacagcca gccaccctac anccagggga   300
ggttacagcc agggttacac agg                                             323
```

<210> SEQ ID NO 10
<211> LENGTH: 914

```
<212> TYPE: DNA
<213> ORGANISM: Homo sapiens

<400> SEQUENCE: 10
ggcggcttcc agaaaaaagg ggaggcagcg gtggaggagg caactaccga ggaggtttca      60
accgcagcgg aggtggtggc tatagcagaa ccgctggggt aacaacaacc gggataacaa     120
caactccaac aacagaggca gctacaaccg gctccccag caacagccgc caccacagca     180
gcctccgcca ccacagccac caccccagca gccaccgcca ccacccagct acagccctgc     240
tcggaacccc ccaggggcca gcacctacaa taagaacagc aacatccctg gctcaagcgc     300
caataccagc accccaccg tcagcagcta cagcccttcc acagccgagt tacagccagc     360
caccctacaa ccagggagg ttacagccag ggttacacag gccaccgcc tccacctcca     420 ccaccacctg cctacaacta tgggagctac ggcggttaca accggcccc ctataccca     480 ccgccacccc ccaccgcaca gacctaccct cagcccaact ataaccagta tcagcagtat     540
gccagcagtg gaaccagtac tatcagaacc agggccagtg gcgccatact acgggaacta     600
cgactacggg agctactccg ggaacacaca gggtggcaca agtacacagt agccagtgtg     660
acccagaggc tcccggaggc ccctgccggc ttcctccacc agcgcctgcc tcggcccctc     720
ctctgccccc gccagatccc gtggtgctgg ggatggggtc atcccagggc tgcctccctc     780
cagcccactg cctcccctct gagggcttc cttcccctcc atagggccag gcattttttt     840
ctggattcaa acaggcaaca atgaccttt attttctgtt tgtccccacc tccccagcct     900
tccacctcct gttc                                                       914

<210> SEQ ID NO 11
<211> LENGTH: 45
<212> TYPE: PRT
<213> ORGANISM: Homo sapiens

<400> SEQUENCE: 11

Arg Leu Pro Glu Lys Arg Gly Gly Ser Gly Gly Gly Asn Tyr Arg
 1               5                  10                  15

Gly Gly Phe Asn Arg Ser Gly Gly Gly Gly Tyr Ser Arg Thr Ala Gly
                20                  25                  30

Val Thr Thr Thr Gly Ile Thr Thr Thr Pro Thr Glu
            35                  40                  45

<210> SEQ ID NO 12
<211> LENGTH: 70
<212> TYPE: PRT
<213> ORGANISM: Homo sapiens

<400> SEQUENCE: 12

Met Gly Ala Thr Ala Val Thr Thr Arg Pro Pro Ile Pro His Arg His
 1               5                  10                  15

Pro Pro Pro His Arg Pro Thr Leu Ser Pro Thr Ile Thr Ser Ile Ser
                20                  25                  30

Ser Met Pro Ala Val Glu Pro Val Leu Ser Glu Pro Gly Pro Val Ala
            35                  40                  45

Pro Tyr Tyr Gly Asn Tyr Asp Tyr Gly Ser Tyr Ser Gly Asn Thr Gln
        50                  55                  60

Gly Gly Thr Ser Thr Gln
65                  70

<210> SEQ ID NO 13
```

-continued

```
<211> LENGTH: 33
<212> TYPE: PRT
<213> ORGANISM: Homo sapiens

<400> SEQUENCE: 13

Gly Gly Phe Gln Lys Lys Gly Glu Ala Ala Val Glu Ala Thr Thr
 1               5                  10                  15

Glu Glu Val Ser Thr Ala Ala Glu Val Val Ala Ile Ala Glu Pro Leu
            20                  25                  30

Gly

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence:forward
      primer

<400> SEQUENCE: 14
ggactaggcc gaggtggcct ctccaggcct tgattatgag cctg            44

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence:reverse
      primer

<400> SEQUENCE: 15
ggactaggcc tcctcggccc tacctctgca ctatgtcact gatttc          46
```

What is claimed is:

1. A method for identifying a molecule that modulates the formation of a complex comprising 53BP2 and a protein selected from the group consisting of β-tubulin, p62, hnRNP G, the 53BP2-IP1 polypeptide comprising SEQ ID NO: 11, the 53BP2-IP2 polypeptide comprising SEQ ID NO:12, and the 53BP2-IP3 polypeptide comprising SEQ ID NO:13; said method comprising contacting one or more candidate molecules with 53BP2 in the presence of said selected protein; and measuring the amount of complex that forms between 53BP2 and said selected protein; wherein an increase or decrease in the amount of complex that forms relative to the amount that forms in the absence of the candidate molecules indicates that the candidate molecules modulate the formation of said complex comprising 53BP2 and said selected protein.

2. The method of claim 1, wherein said contacting is carried out by contacting the candidate molecule with an isolated recombinant cell comprising a 53BP2 gene and a 53BP2-IP gene selected from the group consisting of β-tubulin, p62, hnRNP G, 53BP2-IP1, 53BP2-IP2, and 53BP2-IP3, wherein the 53BP2 gene is under the control of a promoter that is not the native 53BP2 gene promoter and the 53BP2-IP gene is under the control of a promoter that is not the native 53BP2-IP gene promoter.

3. The method of claim 2, wherein said isolated recombinant cell is an animal cell.

4. The method of claim 2, wherein said isolated recombinant cell is a mammalian cell.

5. The method of claim 1 wherein the candidate molecule is recombinantly expressed in an isolated recombinant cell comprising a 53BP2 gene and a 53BP2-IP gene selected from the group consisting of β-tubulin, p62, hnRNP G, 53BP2-IP1, 53BP2-IP2, and 53BP2-IP3, wherein the 53BP2 gene is under the control of a promoter that is not the native 53BP2 gene promoter and the 53BP2-IP gene is under the control of a promoter that is not the native 53BP2-IP gene promoter.

6. The method of claim 5, wherein said isolated recombinant cell is an animal cell.

7. The method of claim 5, wherein said isolated recombinant cell is a mammalian cell.

8. The method of claim 1 wherein said contacting is carried out in vitro.

9. A method for identifying a molecule that modulates the transcriptional regulatory activity of a complex comprising 53BP2 and a protein selected from the group consisting of β-tubulin, p62, hnRNP G, the 53BP2-IP1 polypeptide comprising SEQ ID NO: 11, the 53BP2-IP2 polypeptide comprising SEQ ID NO:12, and the 53BP2-IP3 polypeptide comprising SEQ ID NO:13; said method comprising contacting one or more candidate molecules with said complex; and measuring the transcriptional regulatory activity of said complex; wherein an increase or decrease in the transcriptional regulatory activity of said complex compared to the transcriptional regulatory activity of said complex in the absence of the candidate molecule indicates that the candidate molecule modulates the transcriptional regulatory activity of said complex.

10. The method of claim 9, wherein said contacting is carried out by contacting the candidate molecule with an isolated recombinant cell comprising a 53BP2-gene and a 53BP2-IP gene selected from the group consisting of β-tubulin, p62, hnRNP G, 53BP2-IP1, 53BP2-IP2, and 53BP2-IP3, in which the 53BP2 gene is under the control of a promoter is not the native 53BP2 gene promoter and the 53BP2-IP gene is under the control of a promoter that is not the native 53BP2-IP gene promoter.

11. The method of claim 10, wherein said isolated recombinant cell is an animal cell.

12. The method of claim 10, wherein said isolated recombinant cell is a mammalian cell.

13. The method of claim 9 wherein the candidate molecule is recombinantly expressed in an isolated recombinant cell comprising a 53BP2 gene and a 53BP2-IP gene selected from the group consisting of β-tubulin, p62, hnRNP G, 53BP2-IP1, 53BP2-IP2, and 53BP2-IP3, in which the 53BP2 gene is under the control of a promoter that is not the native 53BP2 gene promoter and the 53BP2-IP gene is under the control of a promoter that is not the native 53BP2-IP gene promoter.

14. The method of claim 13, wherein said isolated recombinant cell is an animal cell.

15. The method of claim 13, wherein said isolated recombinant cell is a mammalian cell.

16. The method of claim 9 wherein said contact is carried out in vitro.

* * * * *